(12) United States Patent
Branch et al.

(10) Patent No.: US 7,897,618 B2
(45) Date of Patent: Mar. 1, 2011

(54) N-AROYL CYCLIC AMINE DERIVATIVES AS OREXIN RECEPTOR ANTAGONISTS

(75) Inventors: Clive Leslie Branch, Harlow (GB); Wai Ngor Chan, Harlow (GB); Amanda Johns, Harlow (GB); Christopher Norbert Johnson, Harlow (GB); David John Nash, Harlow (GB); Riccardo Novelli, Harlow (GB); Jean-Pierre Pilleux, Mayenne (FR); Roderick Alan Porter, Harlow (GB); Rachel Elizabeth Anne Stead, Harlow (GB); Geoffrey Stemp, Harlow (GB)

(73) Assignee: SmithKline Beecham Limited, Brentford, Middlesex (GB)

( * ) Notice: Subject to any disclaimer, the term of this patent is extended or adjusted under 35 U.S.C. 154(b) by 419 days.

(21) Appl. No.: 11/926,375

(22) Filed: Oct. 29, 2007

(65) Prior Publication Data

US 2009/0036442 A1 Feb. 5, 2009

Related U.S. Application Data

(63) Continuation of application No. 10/481,133, filed as application No. PCT/EP02/07009 on Jun. 25, 2002, now Pat. No. 7,470,710.

(30) Foreign Application Priority Data

Jun. 28, 2001 (GB) .................................. 0115863.3
Dec. 19, 2001 (GB) .................................. 0130342.9

(51) Int. Cl.
*A61K 31/4545* (2006.01)
*A61K 31/4725* (2006.01)
*C07D 401/14* (2006.01)
*C07D 405/14* (2006.01)

(52) U.S. Cl. ........................ 514/307; 514/309; 514/310; 546/141; 546/143; 546/145; 546/146

(58) Field of Classification Search ................. 546/141, 546/143, 145, 146; 514/307, 309, 310
See application file for complete search history.

(56) References Cited

U.S. PATENT DOCUMENTS

| | | | |
|---|---|---|---|
| 5,547,978 A | 8/1996 | Christensen et al. | 514/422 |
| 6,326,379 B1 | 12/2001 | Macor et al. | 514/303 |
| 6,677,354 B2 | 1/2004 | Branch et al. | 514/318 |
| 6,706,720 B2 | 3/2004 | Atwal et al. | 514/259.3 |
| 2004/0143115 A1 | 7/2004 | Branch et al. | 540/607 |
| 2004/0192673 A1 | 9/2004 | Gaillard et al. | 514/217.04 |
| 2004/0215014 A1 | 10/2004 | Chan et al. | 540/596 |
| 2006/0040937 A1 | 2/2006 | Branch et al. | 514/235.5 |

FOREIGN PATENT DOCUMENTS

| | | |
|---|---|---|
| WO | WO 99/09024 | 2/1999 |
| WO | WO 00/47576 | 8/2000 |
| WO | WO 00/47580 | 8/2000 |
| WO | WO 01/96302 | 12/2001 |

OTHER PUBLICATIONS

Brisbare-Roch et al. *Nature Medicine*, 13(2): 150-155 (2007).
Hagan et al. *Proc. Natl. Acad. Sci. USA.*, 96: 10911-10916 (1999).
Piper et al. *Eur. J. Neurosci.*, 12: 726-730 (2000).
Patani et al. *Chem. Rev.*, 96: 3147-3176 (1996).
Boutrel et al. *PNAS*, 102(52): 19168-19173 (2005).
Borglund et al. *Neuron*, 49: 589-601 (2006).
Harris et al. *Nature*, 437: 556-559 (2005).
Mori et al. *Chem. Pharm. Bull.*, 32(10): 3840-3847 (1984).
Defoin et al. *Helv. Chim. Acta*, 75(1): 109-123 (1992).
Lang et al. *J. Med. Chem.*, 47: 1153-1160 (2004).
Smart et al. *Euro. J. Pharm.*, 440: 199-212 (2002).
Langmead et al. *Br. J. Pharmacol.*, 141: 340-346 (2004).
Porter et al. *Bioorg. & Med. Chem. Lett.*, 11: 1907-1910 (2001).
Duxon et al. *Psychopharmacology*, 153: 203-209 (2001).
White et al. *Peptides*, 26: 2331-2338 (2005).
Ishii et al. *Behav. Brain Res.*, 160: 11-24 (2005).
Ishii et al. *Behav. Brain Res.*, 157: 331-341 (2005).
Ishii et al. *Physiol. & Behav.*, 81: 129-140 (2004).
Smith et al. *Neurosci. Lett.*, 341: 256-258 (2003).
Haynes et al. *Regulatory Peptides*, 104: 153-159 (2002).
Bingham et al. *Pain*, 92: 81-90 (2001).
Rodgers et al. *Eur. J. Neurosci.*, 13: 1444-1452 (2001).
Smart et al. *Br. J. Pharmacol.*, 132: 1179-1182 (2001).
Jones et al. *Psychopharmacology*, 153: 210-218 (2001).
Haynes et al. *Regulatory Peptides*, 96: 45-51 (2000).
Rodgers et al. *Neuropeptides*, 36(5): 303-325 (2002).
Patini et al., *Chem. Rev.*, 96: 3147-3148 (1996).
Kilduff et al. *Trends Neurosci.*, 23: 359-365 (2000).
Taheri et al. *Annu. Rev. Neurosci.*, 25: 283-313 (2002).
Cai et al. *Expert Opin. Ther. Patents*, 16(5): 631-646 (2006).

*Primary Examiner*—Patricia L Morris
(74) *Attorney, Agent, or Firm*—Kathryn L. Sieburth; Lorraine Ling

(57) ABSTRACT

Disclosed are N-aroyl cyclic amine derivatives having the formula:

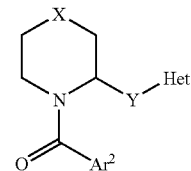

where the variables are as define herein, and their use as pharmaceuticals, specifically as orexin receptor antagonists.

7 Claims, No Drawings

N-AROYL CYCLIC AMINE DERIVATIVES AS OREXIN RECEPTOR ANTAGONISTS

This application is a continuation of application Ser. No. 10/481,133, filed Apr. 26, 2004, now U.S. Pat. No. 7,470,710, which is a 371 of International Application No. PCT/EP02/07009, filed 25 Jun. 2002, which claims the priority of GB 0130342.9, filed 19 Dec. 2001, and GB 0115863.3, filed 28 Jun. 2001, which are incorporated herein in their entireties.

This invention relates to N-aroyl cyclic amine derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; nausea, vomiting; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see *Cell,* 1998, 92, 573-585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

The present invention provides N-aroyl cyclic amine derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders Additionally these compounds are useful in stroke, particularly ischemic or haemorrhagic stroke, and/or blocking the emetic response i.e. the compounds are useful in the treatment of nausea and vomiting.

International Patent Applications WO99/09024, WO99/58533, WO00/47577 and WO00/47580 disclose phenyl urea derivatives and WO00/47576 discloses quinolinyl cinnamide derivatives as orexin receptor antagonists. (2R)-1-[3,5-bis(trifluoromethyl)benzoyl]-2-(1H-indol-3-ylmethyl)piperazine is disclosed in EP899270 as a starting material in the preparation of compounds useful for therapy of functional and inflammatory disorders of the gastrointestinal tract. The compound is also disclosed as Example 6 in EP655442. EP655442 describes piperizine derivatives useful as Tachykinin antagonists. 1-Benzoyl-2-[(1H-indol-3-yl)methyl]piperazine is also disclosed therein.

(2R)-1-(3,5-dichlorobenzoyl)-2-[(1H-indol-3-yl)methyl]piperazine and (2R)-1-[3,5-bis(trifluoromethyl)benzoyl]-2-

[1H-indol-3-yl)methyl]piperazine are used as starting materials/intermediates in WO9857954.

(2R)-2-[1H-indol-3-yl)methyl]-1-[3-methoxy-5-trifluoromethyl)benzoyl]piperazine, is disclosed as a prepared by preparation 42 in WO00/35915.

According to the invention there is provided a compound of formula (I):

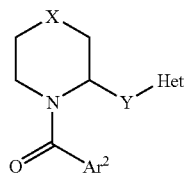

wherein:

X represents a bond, oxygen, $NR^3$ or a group $(CH_2)_n$, wherein n represents 1, 2 or 3;

Y represents $CH_2$, CO, CH(OH), or $CH_2CH(OH)$;

Het is an optionally substituted bicyclic heteroaryl group containing up to 4 heteroatoms selected from N, O and S;

$Ar^2$ represents an optionally substituted phenyl or a 5- or 6-membered heterocyclyl group containing up to 3 heteroatoms selected from N, O and S, wherein the phenyl or heterocyclyl group is substituted by $R^1$ and further optional substituents; or $Ar^2$ represents an optionally substituted bicyclic aromatic or bicyclic heteroaromatic group containing up to 3 heteroatoms selected from N, O and S;

$R^1$ represents hydrogen, optionally substituted $(C_{1-4})$ alkoxy, halo, cyano, optionally substituted $(C_{1-6})$alkyl, optionally substituted phenyl, or an optionally substituted 5- or 6-membered heterocyclyl group containing up to 4 heteroatoms selected from N, O and S;

$R^3$ represents hydrogen or an optionally substituent $(C_{1-4})$ alkyl other than when Het is indolyl where $R^3$ represents hydrogen or $(C_{1-4})$ alkyl;

or a pharmaceutically acceptable salt thereof.

with the proviso that;

when X is NH, Y is $CH_2$ and Het is indolyl, $Ar^2$ is not 3,5-bis(trifluoromethyl)phenyl;

or the compound is not (2R)-1-(3,5-dichlorobenzoyl)-2-[(1H-indol-3-yl)methyl]piperazine;

(2R)-2-[1H-indol-3-yl)methyl]-1-[3-methoxy-5-trifluoromethyl)benzoyl]piperazine; or 1-benzolyl-2-[1H-indol-3-yl)methyl]piperazine.

Preferably where $Ar^2$ represents phenyl or a 5- or 6-membered heterocyclyl group containing up to 3 heteroatoms selected from N, O and S, the $R^1$ group is situated adjacent to the point of attachment to the amide carbonyl.

X is preferably a bond, oxygen or $CH_2$, NH or NMe, more preferably $CH_2$, NH or NMe, most preferably $CH_2$.

Alternatively X is preferably a bond, oxygen or $(CH_2)_n$ wherein n is 1 or 2.

Y is preferably $CH_2$.

Preferably $R^3$ is hydrogen or a $(C_{1-4})$alkyl.

Het may have up to 5, preferably 1, 2 or 3 optional substituents.

Examples of when Het is an optionally substituted bicyclic heteroaryl group are quinoxalinyl, quinazolinyl, pyridopyrazinyl, benzoxazolyl, benzothienyl, benzofuranyl, benzimidazolyl, naphthyridinyl or benzothiazolyl. Additionally Het may be indolyl, triazolopyridinyl, furopyridinyl, pyridopyrimidinyl, isoquinolinyl or quinolinyl. Furthermore Het can be oxazolylpyridinyl or tetrahydrobenzimidazolyl, tetrahydrobenzofuranyl, or tetrahydrotriazolopyridinyl.

Preferably Het is benzofuranyl, benzoxazolyl, benzimidazolyl, furopyridinyl, benzothiazolyl, indolyl, benzothienyl, triazolopyridinyl, quinolinyl and tetrahydrotriazolopyryidinyl, more preferably benzimidazolyl, benzofuranyl, benzoxazolyl, even more preferably benzofuranyl or benzimidazolyl.

When $Ar^2$ is a 5- or 6-membered heteroaryl group containing up to 3 heteroatoms selected from N, O and S, it may be furanyl, thienyl, pyrrolyl, oxazolyl, thiazolyl, imidazolyl, oxadiazolyl, thiadiazolyl, triazolyl, triazinyl, pyridazinyl, pyridinyl, pyrimidinyl, isothiazolyl, isoxazolyl, pyrazinyl or pyrazolyl.

More specifically, examples of $Ar^2$ are thiazolyl, pyrazolyl, triazolyl, pyridazinyl, oxazolyl, pyridinyl, pyrimidinyl, isoxazolyl and thienyl.

When $R^1$ is a 5- or 6-membered heterocyclyl group containing up to 4 heteroatoms selected from N, O and S, it may be furanyl, thienyl, pyrrolyl, oxazolyl, thiazolyl, imidazolyl, oxadiazolyl, thiadiazolyl, pyridinyl, triazolyl, triazinyl, pyridazinyl, pyrimidinyl, isothiazolyl, isoxazolyl, pyrazinyl or pyrazolyl. Additional heterocyclyl groups can be morpholinyl, piperazinyl and thiomorpholinyl. Furthermore it can be tetrazolyl, piperidinyl or pyrrolidinyl.

Preferably when $R^1$ is a 5- or 6-membered heterocyclyl group containing up to 4 heteroatoms selected from N, O and S, it may be oxadiazolyl, pyridinyl, pyrimidinyl, morpholinyl pyrazolyl or pyrrolyl.

Examples of where $Ar^2$ represents an optionally substituted bicyclic aromatic or bicyclic heteroaromatic include naphthyl, quinolinyl, napthhyridinyl, benzofuranyl, benzimidazolyl, quinoxalinyl or quinazolinyl. Additionally $Ar^2$ may be isoquinolinyl or benzoxazolyl. Furthermore it can benzotriazolyl, benzothienyl, indolyl, benzothiazolyl, or benzothiadiazolyl.

Preferably $Ar^2$ represents optionally substituted phenyl, pyridinyl, thiazolyl, pyrazolyl, pyridazinyl, thienyl, naphthyl, triazolyl, isoxazolyl, quinolinyl, or isoquinolinyl.

More preferably $Ar^2$ represents optionally substituted phenyl, pyridinyl, thiazolyl, pyrazolyl, thienyl, triazolyl, quinolinyl, or isoquinolinyl.

Even more preferably $Ar^2$ represents optionally substituted phenyl, pyridinyl, thiazolyl, pyrazolyl, thienyl, or 1,2,3-triazolyl.

Alternatively $R^1$ represents hydrogen, optionally substituted $(C_{1-4})$alkoxy, halo, optionally substituted $(C_{1-6})$alkyl, optionally substituted phenyl, or an optionally substituted 5- or 6-membered heterocyclyl group containing up to 3 heteroatoms selected from N, O and S.

Preferably $R^1$ represents optionally substituted $(C_{1-4})$ alkoxy, halo, optionally substituted $(C_{1-6})$alkyl, optionally substituted phenyl, or an optionally substituted 5- or 6-membered heterocyclyl group containing up to 3 heteroatoms selected from N, O and S.

Even more preferably $R^1$ represents an optionally substituted phenyl, pyridinyl, pyrazolyl pyrimidinyl or oxadiazolyl group.

Optional substituents for the groups Het, $Ar^2$, $R^1$ and $R^3$ include halogen, hydroxy, oxo, cyano, nitro, $(C_{1-4})$alkyl, $(C_{1-4})$alkoxy, hydroxy$(C_{1-4})$alkyl, hydroxy$(C_{1-4})$alkoxy, halo $(C_{1-4})$alkyl, halo$(C_{1-4})$alkoxy, aryl$(C_{1-4})$alkoxy, $(C_{1-4})$alkylthio, hydroxy$(C_{1-4})$alkyl, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$alkylsulfonyl$(C_{1-4})$alkyl, arylsulfonyl, arylsulfonyloxy, arylsulfonyl $(C_{1-4})$alkyl, $(C_{1-4})$alkylsulfonamido, $(C_{1-4})$alkylamido, ($C_{1-4}$)alkylsulfonamido($C_{1-4}$)alkyl, ($C_{1-4}$)alkylamido($C_{1-4}$)alkyl, arylsulfonamido, arylcarboxamido, arylsulfonamido ($C_{1-4}$)alkyl, arylcarboxamido($C_{1-4}$)alkyl, aroyl, aroyl($C_{1-4}$)alkyl, or aryl($C_{1-4}$)alkanoyl group; a group $R^aR^bN$—, $R^aOCO(CH_2)_r$, $R^aCON(R^a)(CH_2)_r$, $R^aR^bNCO(CH_2)_r$, $R^aR^bNSO_2(CH_2)_r$ or $R^aSO_2NR^b(CH_2)_r$ where each of $R^a$ and $R^b$ independently represents a hydrogen atom or a ($C_{1-4}$)alkyl group or where appropriate $R^aR^b$ forms part of a ($C_{3-6}$)azacyloalkane or ($C_{3-6}$)(2-oxo)azacycloalkane ring and r represents zero or an integer from 1 to 4. Additional substituents are ($C_{1-4}$)acyl, aryl, aryl($C_{1-4}$)alkyl, ($C_{1-4}$)alkylamino($C_{1-4}$)alkyl, $R^aR^bN(CH_2)n$-, $R^aR^bN(CH_2)nO$—, wherein n represents an integer from 1 to 4. Additionally when the substituent is $R^aR^bN(CH_2)n$- or $R^aR^bN(CH_2)nO$, $R^a$ with at least one $CH_2$ of the $(CH_2)n$ portion of the group form a ($C_{3-6}$)azacycloalkane and $R^b$ represents hydrogen, a ($C_{1-4}$)alkyl group or with the nitrogen to which it is attached forms a second ($C_{3-6}$)azacycloalkane fused to the first ($C_{3-6}$)azacycloalkane.

Preferred optional substituents for $Ar^2$ are halogen, cyano, ($C_{1-4}$)alkyl, hydroxy($C_{1-4}$)alkyl, ($C_{1-4}$)alkoxy($C_{1-4}$)alkyl, $R^aR^bN(CH_2)n$ or $R^aR^bN$, more preferably halogen, cyano and ($C_{1-4}$)alkyl. Additional substituents are ($C_{1-4}$)acyl, $R^aR^bN(CH_2)nO$, ($C_{1-4}$)alkoxy, phenyl, and ($C_{1-4}$)alkylamido.

More preferred substituents for $Ar^2$ are ($C_{1-4}$)alkyl, hydroxy($C_{1-4}$)alkyl, $R^aR^bN$, ($C_{1-4}$)alkoxy, $R^aR^bN(CH_2)n$, ($C_{1-4}$)acyl, and ($C_{1-4}$)alkylamido.

Preferred optional substituents for Het are halogen, cyano, ($C_{1-4}$)alkyl, hydroxy($C_{1-4}$)alkyl, ($C_{1-4}$)acyl, ($C_{1-4}$)alkoxy ($C_{1-4}$)alkyl, $R^aR^bNCO(CH_2)_r$, $R^aR^bN(CH_2)n$, $R^aR^bN(CH_2)nO$ or $R^aR^bN$. Additional optional substituents are ($C_{1-4}$)alkoxy or $CF_3$.

More preferred substituents for Het are halogen, $R^aR^bNCO(CH_2)_r$, cyano, ($C_{1-4}$)alkoxy, ($C_{1-4}$)alkyl, $R^aR^bN(CH_2)n$, hydroxy($C_{1-4}$)alkyl, ($C_{1-4}$)acyl or ($C_{1-4}$)alkoxy($C_{1-4}$)alkyl.

Preferred optional substituents for $R^1$ are halogen, ($C_{1-4}$)alkoxy($C_{1-4}$)alkyl, $R^aR^bN$, $R^aR^bN(CH_2)nO$ or $R^aR^bN(CH_2)n$. Additional optional substituents are ($C_{1-4}$)alkyl, ($C_{1-4}$)alkoxy and ($C_{1-4}$)acyl.

More preferred substituents for $R^1$ are halogen, $R^aR^bN(CH_2)nO$, ($C_{1-4}$)alkyl, and ($C_{1-4}$)alkoxy.

Preferred optional substituents for $R^3$ may be selected from halogen, hydroxy, cyano, ($C_{1-4}$)alkoxy, $R^aR^bN(CH_2)nO$ or $R^aR^bN$.

In the groups Het and $Ar^2$, substituents positioned ortho to one another may be linked to form a ring.

Illustrative compounds of formula (I) can be selected from:

| | |
|---|---|
| 1 | (RS)-2-(2-Benzonaranylmethyl)-1-((5-(4-fluorophenyl)-2-methyl-thiazol-4-yl)-carbonyl)-piperidine |
| 2 | (RS)-1-(2-Benzooxazol-2-ylmethyl-piperidin-1-yl)-1-[5-(4-fluoro-phenyl)-2-methyl-thiazol-4-yl]-methanone |
| 3 | (RS)-1-(2-Benzooxazol-2-ylmethyl-piperidin-1-yl)-1-[2-(3-methyl-[1,2,4]oxadiazol-5-yl)-phenyl]-methanone | and pharmaceutical acceptable salts thereof.

Additional compounds of formula (I) can be selected from:

| | |
|---|---|
| 4 | (RS)-1-(2-Benzofuran-2-ylmethyl-piperidin-1-yl)-1-[4-(4-fluoro-phenyl)-1-methyl-1-H-pyrazol-3-yl]-methane |
| 5 | (RS)-1-[2-(5-Fluoro-benzofuran-2-ylmethyl)-piperidin-1-yl]-1-[5-(4-fluoro-phenyl)-2-methyl-thiazol-4-yl]-methanone |
| 6 | (RS)-1-[2-(5-Fluoro-benzofuran-2-ylmethyl)-piperidin-1-yl]-1-(5-pyridin-2-yl-thiazol-4-yl)-methanone |
| 7 | (RS)-1-[2-(5-Fluoro-benzofuran-2-ylmethyl)-piperidin-1-yl]-1-quinolin-4-yl-methanone |
| 8 | (RS)-1-[2-(5-Fluoro-benzofuran-2-ylmethyl)-piperidin-1-yl]-1-quinolin-5-yl-methanone |
| 9 | (RS)-1-[2-(5-Fluoro-benzofuran-2-ylmethyl)-piperidin-1-yl]-1-(2-methoxy-pyridin-3-yl)-methanone |
| 10 | (RS)-1-[2-Dimethylamino-5-(4-fluoro-phenyl)-thiazol-4-yl]-1-[2-(5-fluoro-benzofuran-2-ylmethyl)-piperidin-1-yl]-methanone |
| 11 | (RS)-1-[2-(5-Fluoro-benzofuran-2-ylmethyl)-piperidin-1-yl]-1-(2-morpholin-4-yl-phenyl)-methanone |
| 12 | (RS)-1-[2-(5-Fluoro-benzofuran-2-ylmethyl)-piperidin-1-yl]-1-(2-trifluoromethoxy-phenyl)-methanone |
| 13 | (RS)-1-(2-Benzofuran-2-ylmethyl-piperidin-1-yl)-1-[2-(2-dimethylamino-ethoxy)-phenyl]-methanone |
| 14 | (RS)-1-(2-Benzofuran-2-ylmethyl-piperidin-1-yl)-1-quinolin-8-yl-methanone |
| 15 | (RS)-1-(2-Benzofuran-2-ylmethyl-piperidin-1-yl)-1-(2-pyrimidin-2-yl-phenyl)-methanone |
| 16 | (RS)-1-(2-Benzofuran-2-ylmethyl-piperidin-1-yl)-1-[5-(4-fluoro-phenyl)-2H-[1,2,3]triazol-4-yl]-methanone |
| 17 | (RS)-1-(2-Benzofuran-2-ylmethyl-piperidin-1-yl)-1-[4-(4-fluoro-phenyl)-1H-pyrazol-3-yl]-methanone |
| 18 | (RS)-1-(2-Benzofuran-2-ylmethyl-piperidin-1-yl)-1-[5-(4-fluoro-phenyl)-2-hydroxymethyl-thiazol-4-yl]-methanone |
| 19 | (RS)-1-(2-Benzofuran-2-ylmethyl-piperidin-1-yl)-1-isoquinolin-8-yl-methanone |
| 20 | (RS)-1-(2-Benzofuran-2-ylmethyl-piperidin-1-yl)-1-isoquinolin-5-yl-methanone |
| 21 | (RS)-1-(2-Benzofuran-2-ylmethyl-piperidin-1-yl)-1-{5-[3-(3-dimethylamino-propoxy)-phenyl]-2-methyl-thiazol-4-yl}-methanone |
| 22 | (RS)-1-(2-Benzofuran-2-ylmethyl-piperidin-1-yl)-1-{5-[3-(4-dimethylamino-butoxy)-phenyl]-2-methyl-thiazol-4-yl}-methanone |

-continued

| | |
|---|---|
| 23 | (RS)-1-[5-(4-Fluoro-phenyl)-2-methyl-thiazol-4-yl]-1-(2-furo[2,3-b]pyridin-2-ylmethyl-piperidin-1-yl)-methanone |
| 24 | (RS)-1-[4-(4-Fluoro-phenyl)-1-methyl-1H-pyrazole-3-yl]-(2-furo[2,3-b]pyridin-2-ylmethyl-piperidin-1-yl)methanone |
| 25 | (RS)-1-[5-(4-Fluoro-phenyl)-2-methyl-thiazol-4-yl]-1-(2-quinolin-2-ylmethyl-piperidin-1-yl)-methanone |
| 26 | (RS)-1-Benzofuran-2-yl-1-(1-{1-[5-(4-fluoro-phenyl)-2-methyl-thiazol-4-yl]-methanoyl}-piperidin-2-yl)-methanone |
| 27 | (RS)-1-[2-(1H-benzoimidazol-2-ylmethyl)-piperidin-1-yl]-1-[5-(4-fluoro-phenyl)-2-methyl-thiazol-4-yl]-methanone |
| 28 | (RS)-1-[2-(5-Chloro-1H-benzoimidazol-2-ylmethyl)-piperidin-1-yl]-1-[5-(4-fluoro-phenyl)-2-methyl-thiazol-4-yl]-methanone |
| 29 | (RS)-1-[2-(5-Fluoro-1H-benzoimidazol-2-ylmethyl)-piperidin-1-yl]-1-[5-(4-fluoro-phenyl)-2-methyl-thiazol-4-yl]-methanone |
| 30 | (RS)-1-[2-(5-Chloro-6-fluoro-1H-benzoimidazol-2-ylmethyl)-piperidin-1-yl]-1-[5-(4-fluoro-phenyl)-2-methyl-thiazol-4-yl]-methanone |
| 31 | (RS)-1-[5-(4-Fluoro-phenyl)-2-methyl-thiazol-4-yl]-1-[2-(4-methyl-1H-benzoimidazol-2-ylmethyl)-piperidin-1-yl]-methanone |
| 32 | (RS)-1-[2-(4,6-Difluoro-1H-benzoimidazol-2-ylmethyl)-piperidin-1-yl]-1-[5-(4-fluoro-phenyl)-2-methyl-thiazol-4-yl]-methanone |
| 33 | (RS)-1-[2-(4-Dimethylaminomethyl-1H-benzoimidazol-2-ylmethyl)-piperidin-1-yl]-1-[5-(4-fluoro-phenyl)-2-methyl-thiazol-4-yl]-methanone |
| 34 | (RS)-1-[2-(5-Bromo-1H-benzoimidazol-2-ylmethyl)-piperidin-1-yl]-1-[5-(4-fluoro-phenyl)-2-methyl-thiazol-4-yl]-methanone |
| 35 | (RS)-1-[2-(5,6-Difluoro-1H-benzoimidazol-2-ylmethyl)-piperidin-1-yl]-1-[5-(4-fluoro-phenyl)-2-methyl-thiazol-4-yl]-methanone |
| 36 | (RS)-1-[2-(4,5-Difluoro-1H-benzoimidazol-2-ylmethyl)-piperidin-1-yl]-1-[5-(4-fluoro-phenyl)-2-methyl-thiazol-4-yl]-methanone |
| 37 | (RS)-1-[2-(5,6-Difluoro-1H-benzoimidazol-2-ylmethyl)-piperidin-1-yl]-1-[5-(4-fluoro-phenyl)-2-hydroxymethyl-thiazol-4-yl]-methanone |
| 38 | (RS)-1-[2-(4,5-Difluoro-1H-benzoimidazol-2-ylmethyl)-piperidin-1-yl]-1-[5-(4-fluoro-phenyl)-2-hydroxymethyl-thiazol-4-yl]-methanone |
| 39 | (RS)-1-[2-(5,6-Difluoro-1H-benzoimidazol-2-ylmethyl)-piperidin-1-yl]-1-[4-(4-fluoro-phenyl)-1-methyl-1H-pyrazol-3-yl]-methanone |
| 40 | (RS)-1-[2-(5-Methoxy-1H-benzoimidazol-2-ylmethyl)-piperidin-1-yl]-1-[5-(4-fluoro-phenyl)-2-methyl-thiazol-4-yl]-methanone |
| 41 | (RS)-1-[2-(6,7-Difluoro-1H-benzoimidazol-2-ylmethyl)-piperidin-1-yl]-1-(2-methyl-5-phenyl-thiazol-4-yl)-methanone |
| 42 | (RS)-1-[2-(6,7-Difluoro-1H-benzoimidazol-2-ylmethyl)-piperidin-1-yl]-1-[4-(4-fluoro-phenyl)-1-methyl-1H-pyrazol-3-yl]-methanone |
| 43 | (RS)-1-[2-(6,7-Difluoro-1H-benzoimidazol-2-ylmethyl)-piperidin-1-yl]-1-[4-(4-fluoro-phenyl)-1H-pyrazol-3-yl]-methanone |
| 44 | (RS)-1-[2-(4,5-Difluoro-1H-benzoimidazol-2-ylmethyl)-piperidin-1-yl]-1-{5-[3-(2-dimethylamino-ethoxy)-phenyl]-2-methyl-thiazol-4-yl}-methanone |
| 45 | (RS)-1-[2-(4,5-Difluoro-1H-benzoimidazol-2-ylmethyl)-piperidin-1-yl]-1-[5-(2-fluoro-phenyl)-2-methyl-thiazol-4-yl]-methanone |
| 46 | (RS)-1-[2-(4,5-Difluoro-1H-benzoimidazol-2-ylmethyl)-piperidin-1-yl]-1-[5-(3-fluoro-phenyl)-2-methyl-thiazol-4-yl]-methanone |
| 47 | (RS)-1-[2-(4,5-Difluoro-1H-benzoimidazol-2-ylmethyl)-piperidin-1-yl]-1-(2-trifluoromethoxy-phenyl)-methanone |
| 48 | (RS)-1-[2-(4,5-Difluoro-1H-benzoimidazol-2-ylmethyl)-piperidin-1-yl]-1-(2-ethoxy-phenyl)-methanone |
| 49 | (RS)-1-[2-(4,5-Difluoro-1H-benzoimidazol-2-ylmethyl)-piperidin-1-yl]-1-(2,6-dimethoxy-phenyl)-methanone |
| 50 | (RS)-1-[2-(6,7-Difluoro-1H-benzoimidazol-2-ylmethyl)-piperidin-1-yl]-1-(2-pyrazol-1-yl-phenyl)-methanone |
| 51 | (RS)-1-[2-(5,6-Difluoro-1H-benzoimidazol-2-ylmethyl)-piperidin-1-yl]-1-[4-(4-fluoro-phenyl)-1H-pyrazol-3-yl]-methanone |
| 52 | (RS)-1-[2-(5,6-Difluoro-1H-benzoimidazol-2-ylmethyl)-piperidin-1-yl]-1-[2-(3-methyl-[1,2,4]oxadiazol-5-yl)-phenyl]-methanone |
| 53 | (RS)-1-[2-(Difluoro-1H-benzoimidazol-2-ylmethyl)-piperidin-1-yl]-1-[1-(2-dimethylamino-ethyl)-4-(4-fluoro-phenyl)-1H-pyrazol-3-yl]-methanone |
| 54 | (RS)-1-[2-(5,6-Difluoro-1H-benzoimidazol-2-ylmethyl)-piperidin-1-yl]-1-[5-(4-fluoro-phenyl)-2-methyl-2H-[1,2,3]triazol-4-yl]-methanone |
| 55 | (RS)-1-[2-(5,6-Difluoro-1H-benzoimidazol-2-ylmethyl)-piperidin-1-yl]-1-{2-[3-(3-dimethylamino-propoxy)-phenyl]-thiophen-3-yl}-methanone |
| 56 | (RS)-1-[2-(5,6-Difluoro-1-methyl-1H-benzoimidazol-2-ylmethyl)-piperidin-1-yl]-1-[5-(4-fluoro-phenyl)-2-methyl-thiazol-4-yl]-methanone |
| 57 | 1-[(S)-2-(1H-Benzoimidazol-2-ylmethyl)-pyrrolidin-1-yl]-1-[5-(4-fluoro-phenyl)-2-methyl-thiazol-4-yl]-methanone |
| 58 | 1-[(S)-2-(5,6-Difluoro-1H-Benzoimidazol-2-ylmethyl)-pyrrolidin-1-yl]-1-[5-(4-fluoro-phenyl)-2-methyl-thiazol-4-yl]-methanone |
| 59 | 1-[(S)-2-(5,6-Difluoro-1H-Benzoimidazol-2-ylmethyl)-pyrrolidin-1-yl]-1-[4-(4-fluoro-phenyl)-1-methyl-1H-pyrazol-3-yl]methanone |
| 60 | (RS)-1-(2-Benzothiazol-2-ylmethylpiperidin-1-yl)-1-[5-(4-fluorophenyl)-2-methylthiazol-4-yl]-methanone |
| 61 | (RS)-1-(2-Benzothiazol-2-ylmethylpiperidin-1-yl)-1-[4-(4-fluorophenyl)-1-methyl-1-H-pyrazol-3-yl]-methanone |

| | -continued |
|---|---|
| 62 | (RS)-1-(2-Benzothiazol-2-ylmethylpiperidin-1-yl)-1-[2-(3-methyl-[1,2,4]oxadiazol-5-yl)phenyl]-methanone |
| 63 | (RS)-1-[5-(4-Fluorophenyl)-2-methylthiazol-4-yl]-1-[2-(5,6,7,8-tetrahydro-[1,2,4]-triazolo[1,5-a]pyridin-2-ylmethyl)-piperidin-1-yl]-methanone |
| 64 | (RS)-1-[5-(4-Fluorophenyl)-2-methylthiazol-4-yl]-1-(2-[1,2,4]triazolo[1,5-a]pyridin-2-ylmethylpiperidin-1-yl)-methanone |
| 65 | 1-[(RS)-2-((RS)-2-Benzofuran-2-yl-2-hydroxy-ethyl)-piperidin-1-yl]-1-[5-(4-fluoro-phenyl)-2-methyl-thiazol-4-yl]-methanone (as separate diastereoisomers) |
| 66 | (RS)-1-[2-(4-Bromo-1H-benzoimidazol-2-ylmethyl)-piperidin-1-yl]-1-[5-(4-fluorophenyl)-2-methylthiazol-4-yl]methanone |
| 67 | (RS)-1-[2-(4-Cyano-1H-benzoimidazol-2-ylmethyl)-piperidin-1-yl]-1-[5-(4-fluorophenyl)-2-methylthiazol-4-yl]methanone |
| 68 | (RS)-1-[2-(4-Acetyl-1H-benzoimidazol-2-ylmethyl)-piperidin-1-yl]-1-[5-(4-fluorophenyl)-2-methylthiazol-4-yl]methanone |
| 69 | (RS)-2-(1-{1-[5-(4-Fluoro-phenyl)-2-methyl-thiazol-4-yl]-methanoyl}-piperidin-2-ylmethyl)-1H-benzoimidazole-5-carbonitrile |
| 70 | (RS)-1-[2-(5,6-Difluoro-1-propyl-1H-benzoimidazol-2-ylmethyl)-piperidin-1-yl]-1-[5-(4-fluoro-phenyl)-2-methyl-thiazol-4-yl]-methanone |
| 71 | (RS)-1-{2-[5,6-Difluoro-1-(2-methoxy-ethyl)-1H-benzoimidazol-2-ylmethyl]-piperidin-1-yl}-1-[5-(4-fluoro-phenyl)-2-methyl-thiazol-4-yl]-methanone |
| 72 | (RS)-1-{2-[1-(2-Dimethylamino-ethyl)-5,6-difluoro-1H-benzoimidazol-2-ylmethyl]-piperidin-1-yl}-1-[5-(4-fluoro-phenyl)-2-methyl-thiazol-4-yl]-methanone |
| 73 | (RS)-1-{2-[5,6-difluoro-1-(2-hydroxy-ethyl)-1H-benzoimidazol-2-ylmethyl]-piperidin-1-yl}-1-[5-(4-fluoro-phenyl)-2-methyl-thiazol-4-yl]-methanone |
| 74 | (RS)-1-[2-(6,7-Difluoro-1-methyl-1H-benzoimidazol-2-ylmethyl)-piperidin-1-yl]-1-[5-(4-fluorophenyl)-2-methyl-thiazol-4-yl]-methanone |
| 75 | (RS)-1-[2-(4,5-Difluoro-1-methyl-1H-benzoimidazol-2-ylmethyl)-piperidin-1-yl]-1-[5-(4-fluorophenyl)-2-methyl-thiazol-4-yl]-methanone |
| 76 | (RS)-2-(1-{1-[5-(4-Fluorophenyl)-2-methyl-thiazol-4-yl]-methanoyl}-piperidin-2-ylmethyl)-benzofuran-3-carboxylic acid amide |
| 77 | (RS)-2-(1-{1-[4-(4-Fluorophenyl)-1-methyl-1H-pyrazol-3-yl]-methanoyl}-piperidin-2-ylmethyl)-benzofuran-3-carboxylic acid amide |
| 78 | (RS)-1-[3-(4,5-Difluoro-1H-benzoimidazol-2-ylmethyl)-morpholin-4-yl]-1-[5-(4-fluoro-phenyl)-2-methyl-thiazol-4-yl]-methanone |
| 79 | (RS)-1-[5-(4-Fluoro-phenyl)-2-methyl-thiazol-4-yl]-1-(2-furo[3,2-b]-pyridin-2-ylmethyl-piperidin-1-yl)methanone |
| 80 | (RS)-1-[4-(4-Fluoro-phenyl)-1-methyl-1H-pyrazole-3-yl)-(2-furo[3,2-b]pyridin-2-ylmethyl-piperidin-1-yl)methanone |
| 81 | (RS)-1-[2-(3-Bromo-benzofuran-2-ylmethyl)-piperidin-1-yl]-1-[5-(4-fluoro-phenyl)-2-methyl-thiazol-4-yl]-methanone |
| 82 | (RS)-2-(1-{1-[5-(4-Fluoro-phenyl)-2-methyl-thiazol-4-yl]-methanoyl}-piperidin-2-ylmethyl)-benzofuran-3-carbonitrile |
| 83 | (RS)-1-[2-(5-Fluorobenzoruran-2-ylmethyl)-4-methylpiperazin-1-yl]-1-[5-(4-fluorophenyl)-2-methythiazol-4-yl]methanone |
| 84 | (RS)-1-(2-Benzofuran-2-ylmethyl-4-methyl-piperazin-1-yl)-1-[5-(4-fluoro-phenyl)-2-methyl-thiazol-4-yl)]-methanone |
| 85 | (RS)-1-(2-Benzofuran-2-ylmethyl-piperazin-1-yl)-1-[5-(4-fluorophenyl)-2-methyl-thiazol-4-yl]-methanone |
| 86 | 1-{(RS)-2-[(RS)-1-(5-Fluoro-benzofurany-2-yl)-1-hydroxy-methyl]-4-methyl-piperazin-1-yl}-1-[5-(4-fluoro-phenyl)-2-methyl-thiazol-4-yl]-methanone |
| 87 | 1-{(RS)-2-[(RS)-1-(5-Fluoro-benzofurany-2-yl)-1-hydroxy-methyl]-4-methyl-piperazin-1-yl}-1-(2-trifluoromethoxy-phenyl)-methanone |
| 88 | (RS)-1-[2-(1-{1-[5-(4-fluoro-phenyl)-2-methyl-thiazol-4-yl]-methanoyl}-piperidin-2-ylmethyl)-benzofuran-3-yl]-ethanone |
| 89 | (R)-1-[2-(5,6-Difluoro-1H-benzoimidazol-2-ylmethyl)-piperidin-1-yl]-1-[5-(4-fluoro-phenyl)-2-methyl-thiazol-4-yl]-methanone and(S)-1-[2-(5,6-Difluoro-1H-benzoimidazol-2-ylmethyl)-piperidin-1-yl]-1-[5-(4-fluoro-phenyl)-2-methyl-thiazol-4-yl]-methanone | and pharmaceutically acceptable salts thereof.

Further compounds of formula (I) can be selected from

| | |
|---|---|
| 90 | (RS)-1-(2-Benzofuran-2-ylmethyl-piperidin-1-yl)-1-[5-(4-methoxy-phenyl)-2-methyl-thiazol-4-yl]-methanone |
| 91 | (RS)-1-(2-Benzofuran-2-ylmethyl-piperidin-1-yl)-1-{5-[3-(2-dimethylamino-ethoxy)-phenyl]-2-methyl-thiazol-4-yl}-methanone |

| | |
|---|---|
| 92 | (RS)-1-[2-(4,5-Difluoro-1H-benzoimidazol-2-ylmethyl)-piperidin-1-yl]-1-(5-methyl-3-phenyl-isoxazol-4-yl)-methanone |
| 93 | 1-[3-(2,6-Dichloro-phenyl)-5-methyl-isoxazol-4-yl]-1-[2-(4,5-difluoro-1H-benzoimidazol-2-ylmethyl)-piperidin-1-yl]-methanone |
| 94 | (RS)-1-[2-(4,5-Difluoro-1H-benzoimidazol-2-ylmethyl)-piperidin-1-yl]-1-[4-(4-fluoro-phenyl)-2-methyl-2H-pyrazol-3-yl]-methanone |
| 95 | (RS)-1-[3-(2-Chloro-6-fluoro-phenyl)-5-methyl-isoxazol-4-yl]-1-[2-(4,5-difluoro-1H-benzoimidazol-2-ylmethyl)-piperidin-1-yl]-methanone |
| 96 | (RS)-1-[3-(2-Chloro-phenyl)-5-methyl-isoxazol-4-yl]-1-[2-(4,5-difluoro-1H-benzoimidazol-2-ylmethyl)-piperidin-1-yl]-methanone |
| 97 | (RS)-1-[2-(4,5-Difluoro-1H-benzoimidazol-2-ylmethyl)-piperidin-1-yl]-1-(2-propoxy-phenyl)-methanone |
| 98 | (RS)-1-[2-(4,5-Difluoro-1H-benzoimidazol-2-ylmethyl)-piperidin-1-yl]-1-(2-isopropoxy-phenyl)-methanone |
| 99 | (RS)-1-(2-Benzyloxy-phenyl)-1-[2-(4,5-difluoro-1H-benzoimidazol-2-ylmethyl)-piperidin-1-yl]-methanone |
| 100 | (RS)-1-[2-(4,5-Difluoro-1H-benzoimidazol-2-ylmethyl)-piperidin-1-yl]-1-(2-ethoxy-6-methoxy-phenyl)-methanone |
| 101 | (RS)-1-[2-(4,5-Difluoro-1H-benzoimidazol-2-ylmethyl)-piperidin-1-yl]-1-(2-ethoxy-6-methyl-phenyl)-methanone |
| 102 | (RS)-1-(2,6-Diethoxy-phenyl)-1-[2-(4,5-difluoro-1H-benzoimidazol-2-ylmethyl)-piperidin-1-yl]-methanone |
| 103 | 1-(3-{1-[2-(4,5-Difluoro-1H-benzoimidazol-2-ylmethyl)-piperidin-1-yl]-methanoyl}-4-ethoxy-phenyl)-ethanone |
| 104 | (RS)-1-[2-(4,5-Difluoro-1H-benzoimidazol-2-ylmethyl)-piperidin-1-yl]-1-(2-ethoxy-naphthalen-1-yl)-methanone |
| 105 | (RS)-1-[2-(4,5-Difluoro-1H-benzoimidazol-2-ylmethyl)-piperidin-1-yl]-1-(2-pyridin-2-yl-phenyl)-methanone |
| 106 | 1-[2-(6,7-Difluoro-1H-benzoimidazol-2-ylmethyl)-piperidin-1-yl]-1-(2-pyrrol-1-yl-phenyl)-methanone |
| 107 | (RS)-1-[2-(4,5-Difluoro-1H-benzoimidazol-2-ylmethyl)-piperidin-1-yl]-1-{5-[3-(3-dimethylamino-propoxy)-phenyl]-2-methyl-thiazol-4-yl}-methanone |
| 108 | (RS)-1-[2-(4,5-Difluoro-1H-benzoimidazol-2-ylmethyl)-piperidin-1-yl]-1-{5-[3-(4-dimethylamino-butoxy)-phenyl]-2-methyl-thiazol-4-yl}-methanone |
| 109 | (RS)-1-[2-(5,6-Difluoro-1H-benzoimidazol-2-ylmethyl)-piperidin-1-yl]-1-[5-(4-fluoro-phenyl)-2-methoxy-thiazol-4-yl]-methanone |
| 110 | (RS)-1-[2-(5,6-Difluoro-1H-benzoimidazol-2-ylmethyl)-piperidin-1-yl]-1-[2-ethyl-5-(4-fluoro-phenyl)-thiazol-4-yl]-methanone |
| 111 | (RS)-1-[2-(5,6-Difluoro-1H-benzoimidazol-2-ylmethyl)-piperidin-1-yl]-1-[5-(2-fluoro-phenyl)-2-methyl-thiazol-4-yl]-methanone |
| 112 | (RS)-1-[2-(5,6-Difluoro-1H-benzoimidazol-2-ylmethyl)-piperidin-1-yl]-1-[5-(3-fluoro-phenyl)-2-methyl-thiazol-4-yl]-methanone |
| 113 | (RS)-1-[2-(4-Fluoro-1H-benzoimidazol-2-ylmethyl)-piperidin-1-yl]-1-[5-(4-fluoro-phenyl)-2-methyl-thiazol-4-yl]-methanone |
| 114 | (RS)-1-[2-(4-Fluoro-1H-benzoimidazol-2-ylmethyl)-piperidin-1-yl]-1-[4-(4-fluoro-phenyl)-1-methyl-1H-pyrazol-3-yl]-methanone |
| 115 | (RS)-1-[2-(4-Fluoro-1H-benzoimidazol-2-ylmethyl)-piperidin-1-yl]-1-[4-(4-fluoro-phenyl)-1H-pyrazol-3-yl]-methanone |
| 116 | (RS)-1-[2-(4-Fluoro-1H-benzoimidazol-2-ylmethyl)-piperidin-1-yl]-1-[4-(4-fluoro-phenyl)-2-methyl-2H-pyrazol-3-yl]-methanone |
| 117 | (RS)-1-(2-Ethoxy-phenyl)-1-[2-(4-fluoro-1H-benzoimidazol-2-ylmethyl)-piperidin-1-yl]-methanone |
| 118 | (RS)-1-[2-(4-Fluoro-1H-benzoimidazol-2-ylmethyl)-piperidin-1-yl]-1-[5-(4-fluoro-phenyl)-2-hydroxymethyl-thiazol-4-yl]-methanone |
| 119 | (RS)-1-[5-(4-Fluoro-phenyl)-2-methyl-thiazol-4-yl]-1-{2-[4-(1-hydroxy-ethyl)-1H-benzoimidazol-2-ylmethyl]-piperidin-1-yl}-methanone |
| 120 | (RS)-1-(2-Benzofuran-2-ylmethyl-piperidin-1-yl)-1-[5-(4-chloro-phenyl)-2-methyl-thiazol-4-yl]-methanone |
| 121 | (RS)-1-[2-(3-Chloro-furo[3,2-b]pyridin-2-ylmethyl)-piperidin-1-yl]-1-[5-(4-fluoro-phenyl)-2-methyl-thiazol-4-yl]-methanone |
| 122 | (RS)-1-[2-(5,6-Difluoro-1-methyl-1H-benzoimidazol-2-ylmethyl)-piperidin-1-yl]-1-[5-(4-fluoro-phenyl)-2-hydroxymethyl-thiazol-4-yl]-methanone |
| 123 | (RS)-1-[2-(5-Chloro-benzofuran-2-ylmethyl)-4-methyl-piperazin-1-yl]-1-[5-(4-fluoro-phenyl)-2-methyl-thiazol-4-yl]-methanone |
| 124 | (RS)-1-[2-(5-Chloro-benzofuran-2-ylmethyl)-piperazin-1-yl]-1-[5-(4-fluoro-phenyl)-2-methyl-thiazol-4-yl]-methanone |
| 125 | (RS)-1-[2-(5,7-Dichloro-benzofuran-2-ylmethyl)-4-methyl-piperazin-1-yl]-1-[5-(4-fluoro-phenyl)-2-methyl-thiazol-4-yl]-methanone |
| 126 | (RS)-1-[2-(5,7-Dichloro-benzofuran-2-ylmethyl)-piperazin-1-yl]-1-[5-(4-fluoro-phenyl)-2-methyl-thiazol-4-yl]-methanone |
| 127 | (RS)-1-[5-(4-Fluoro-phenyl)-2-methyl-thiazol-4-yl]-1-[2-(1H-indol-2-ylmethyl)-piperidin-1-yl]-methanone |
| 128 | (RS)-5-[1-(2-Benzofuran-2-ylmethyl-piperidin-1-yl)-methanoyl]-4H-benzo[1,4]oxazin-3-one |
| 129 | (RS)-1-[2-(5-Bromo-benzofuran-2-ylmethyl)-piperidin-1-yl]-1-[5-(4-fluoro-phenyl)-2-methyl-thiazol-4-yl]-methanone |

-continued

| | |
|---|---|
| 130 | (RS)-1-[2-(5-Cyano-benzofuran-2-ylmethyl)-piperidin-1-yl]-1-[5-(4-fluoro-phenyl)-2-methyl-thiazol-4-yl]-methanone |
| 131 | (RS)-1-[2-(4-Bromo-benzofuran-2-ylmethyl)-piperidin-1-yl]-1-[5-(4-fluoro-phenyl)-2-methyl-thiazol-4-yl]-methanone |
| 132 | (RS)-1-[2-(4-Cyano-benzofuran-2-ylmethyl)-piperidin-1-yl]-1-[5-(4-fluoro-phenyl)-2-methyl-thiazol-4-yl]-methanone |
| 133 | (RS)-1-[5-(4-Fluoro-phenyl)-2-methyl-thiazol-4-yl]-1-[2-(3-methyl-benzofuran-2-ylmethyl)-piperidin-1-yl]-methanone |
| 134 | (RS)-1-[2-(4-Fluoro-benzofuran-2-ylmethyl)-piperidin-1-yl]-1-[5-(4-fluoro-phenyl)-2-methyl-thiazol-4-yl]-methanone |
| 135 | (RS)-1-[2-(4-Fluoro-benzofuran-2-ylmethyl)-piperidin-1-yl]-1-[4-(4-fluoro-phenyl)-1-methyl-1H-pyrazol-3-yl]-methanone |
| 136 | (RS)-1-[2-(4,6-Dichloro-benzofuran-2-ylmethyl)-4-methyl-piperazin-1-yl]-1-[5-(4-fluoro-phenyl)-2-methyl-thiazol-4-yl]-methanone |
| 137 | (RS)-1-[2-(4,6-Dichloro-benzofuran-2-ylmethyl)-piperazin-1-yl]-1-[5-(4-fluoro-phenyl)-2-methyl-thiazol-4-yl]-methanone |
| 138 | (RS)-1-(2-Benzofuran-2-ylmethyl-pyrrolidin-1-yl)-1-[5-(4-fluoro-phenyl)-2-methyl-thiazol-4-yl]-methanone |
| 139 | (RS)-1-(2-Benzofuran-2-ylmethyl-pyrrolidin-1-yl)-1-[4-(4-fluoro-phenyl)-1-methyl-1H-pyrazol-3-yl]-methanone |
| 140 | (RS)-1-(2-Benzo[b]thiophen-2-ylmethyl-piperidin-1-yl)-1-[5-(4-fluoro-phenyl)-2-methyl-thiazol-4-yl]-methanone |
| 141 | (RS)-1-(2-Benzo[b]thiophen-2-ylmethyl-piperidin-1-yl)-1-[4-(4-fluoro-phenyl)-1-methyl-1H-pyrazol-3-yl]-methanone |
| 142 | (RS)-1-(2-Benzo[b]thiophen-2-ylmethyl-piperidin-1-yl)-1-quinolin-8-yl-methanone |
| 143 | (RS)-1-(2-Benzoruran-2-ylmethyl-piperidin-1-yl)-1-(2-methyl-5-phenyl-thiazol-4-yl)-methanone |
| 144 | 1-[(S)-2-(5,6-Difluoro-1H-benzoimidazol-2-ylmethyl)-pyrrolidin-1-yl]-1-[5-(4-fluoro-phenyl)-2-hydroxymethyl-thiazol-4-yl]-methanone |
| 145 | (RS)-1-(2-Benzoruran-2-ylmethyl-piperidin-1-yl)-1-[2-(3-methyl-[1,2,4]oxadiazol-5-yl)-phenyl]-methanone |
| 146 | (R)-1-[2-(4,6-Difluoro-1H-benzoimidazol-2-ylmethyl)-piperidin-1-yl]-1-[5-(4-fluoro-phenyl)-2-methyl-thiazol-4-yl]-methanone and (S)-1-[2-(4,6-Difluoro-1H-benzoimidazol-2-ylmethyl)-piperidin-1-yl]-1-[5-(4-fluoro-phenyl)-2-methyl-thiazol-4-yl]-methanone | and pharmaceutically acceptable salts thereof.

When a halogen atom is present in the compound of formula (I) it may be fluorine, chlorine, bromine or iodine.

When the compound of formula (I) contains an alkyl group, whether alone or forming part of a larger group, e.g. alkoxy or alkylthio, the alkyl group may be straight chain, branched or cyclic, or combinations thereof, it is preferably methyl or ethyl.

When used herein the term aryl means a 5- to 6-membered ring for example phenyl, or a 7- to 12 membered bicyclic ring system where at least one of the rings is aromatic for example naphthyl.

When used herein the term bicyclic hetero aryl means a 7- to 12 membered bicyclic ring system where at least one of the rings is aromatic for example benzimidazoyl, or tetrahydrobenzimidazolyl.

It will be appreciated that compounds of formula (I) may exist as R or S enantiomers. The present invention includes within its scope all such isomers, including mixtures. Where additional chiral centres are present in compounds of formula (I), the present invention includes within its scope all possible diastereoismers, including mixtures thereof. The different isomeric forms may be separated or resolved one from the other by conventional methods, or any given isomer may be obtained by conventional synthetic methods or by stereospecific or asymmetric syntheses.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, ester or salt of such ester of a compound of formula (I) which, upon administration to the recipient is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and salts thereof. The following schemes detail some synthetic routes to compounds of the invention.

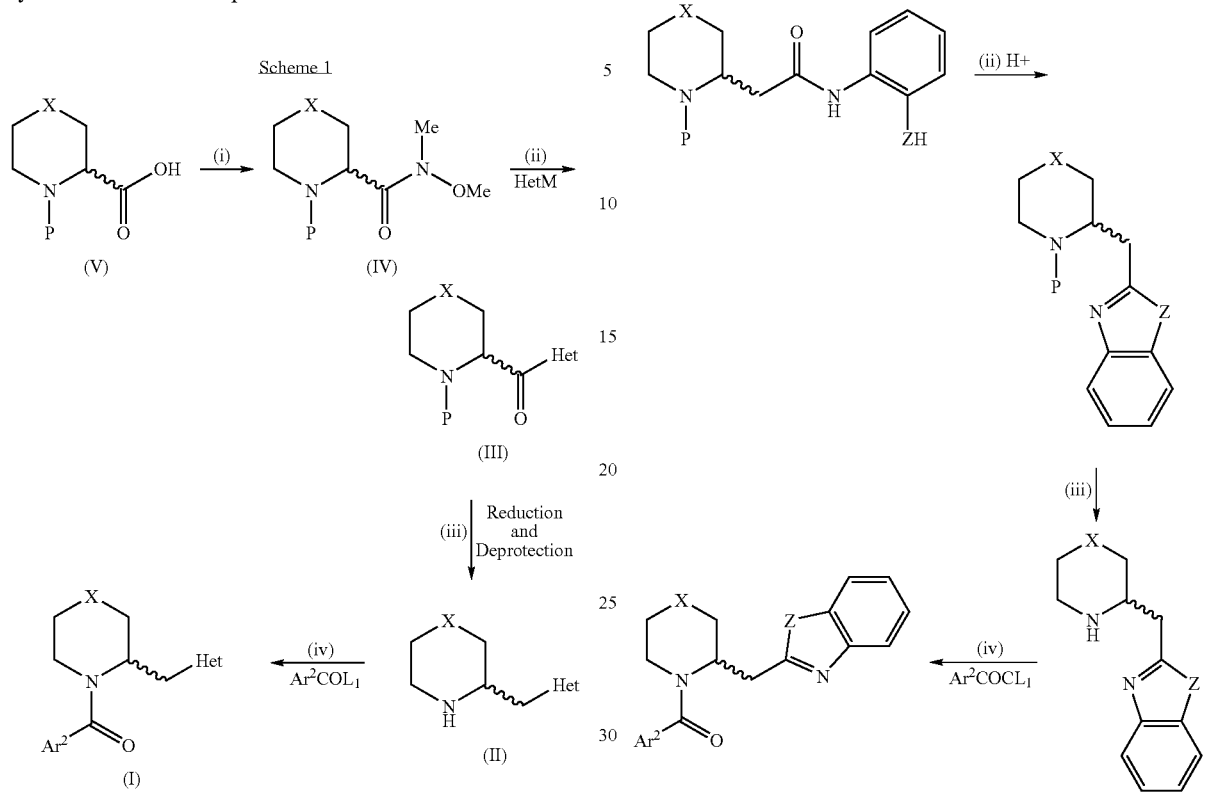

wherein, X, Het, and $Ar^2$ are as defined for compounds of formula (I), P is a protecting group and M is a metal for example lithium.

Examples of suitable leaving groups $L_1$ include halogen, OC(=O)alkyl and OC(=O)O-alkyl. The transformation (II) to (I) may be carried out in an inert solvent such as dichloromethane, in the presence of a base such as triethylamine. Alternatively this step may be carried out when $L^1$ represents hydroxy, in which case reaction with (II) takes place in an inert solvent such as dichloromethane in the presence of a diimide reagent such as 1-ethyl-3-(3-dimethylaminopropyl) carbodiimide hydrochloride, and an activator such as 1-hydroxybenzotriazole.

Examples of protecting groups P include t-butyloxycarbonyl, trifluoroacetyl and benzyloxycarbonyl. Deprotection conditions are respectively, acid (e.g. trifluoroacetic acid in dichloromethane), base (e.g. sodium hydroxide in a solvent such as aqueous methanol) and catalytic hydrogenolysis in an inert solvent (e.g using palladium on charcoal in a lower alcohol or ethyl acetate).

Compounds of formula (V) are known in the literature or can be prepared by known methods.

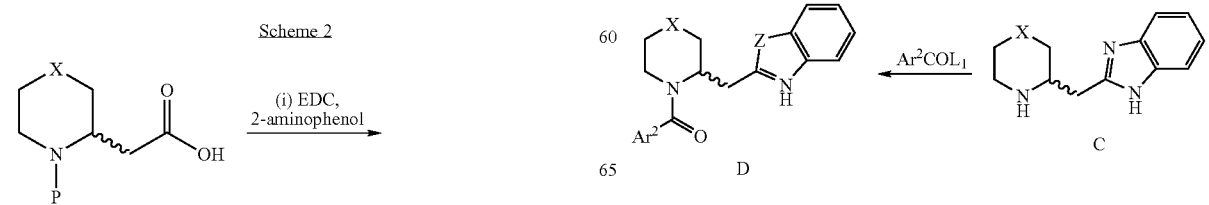

wherein, X, and $Ar^2$ are as defined for compounds of formula (I), Z is S, or O, and P is a protecting group.

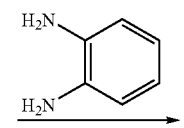

Scheme 3

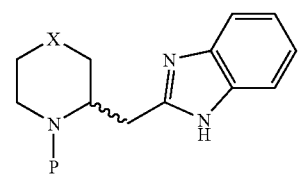

wherein, X, and Ar² are as defined for compounds of formula (I) and P is a protecting group.

Examples of protecting groups P include t-butyloxycarbonyl, trifluoroacetyl and benzyloxycarbonyl. Deprotection conditions are respectively, acid (e.g. trifluoroacetic acid in dichloromethane), base (e.g. sodium hydroxide in a solvent such as aqueous methanol) and catalytic hydrogenolysis in an inert solvent (e.g using palladium on charcoal in a lower alcohol or ethyl acetate).

The transformation of A to B can be carried out at elevated temperature in the absence of solvent or in the presence of an acid such as sulfuric acid or polyphosphoric acid, usually at elevated temperature. Deprotection can occur in situ under acidic conditions, if for example P is t-butoxycarbonyl to afford C directly.

Examples of suitable leaving groups $L_1$ include halogen, OC(=O)alkyl and OC(=O)O-alkyl. The transformation C to D may be carried out in an inert solvent such as dichloromethane, in the presence of a base such as triethylamine. Alternatively this step may be carried out when $L_1$ represents hydroxy, in which case reaction with C takes place in an inert solvent such as dichloromethane in the presence of a diimide reagent such as 1-ethyl-3-(3-dimethylaminopropyl)carbodiimide hydrochloride, and an activator such as 1-hydroxybenzotriazole. Also when $L_1$ represents hydroxy the reaction can be effected using O-(7-azabenzotrazol-1-yl)-N,N,N',N'-tetramethyluronium hexafluorophosphate (HATU) with a base such as triethylamine or N,N-diisopropylethylamine.

Wherein Het, X and Ar² are as defined for formula I and P is a protecting group. Suitable reducing agents include sodium borohydride which can be used at ambient temperature in methanol.

Scheme 5

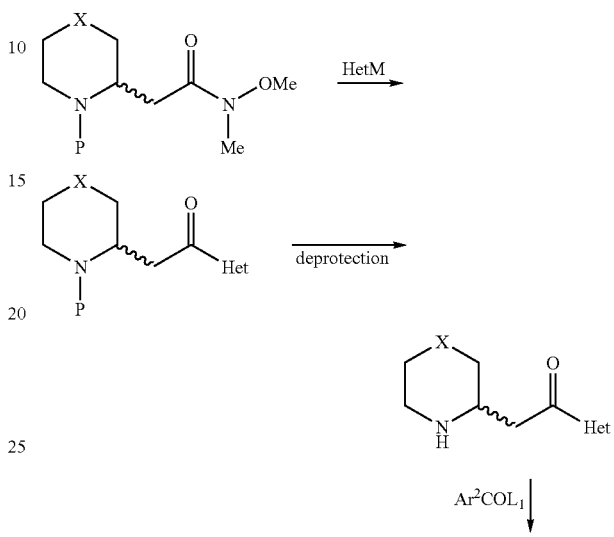

Scheme 4

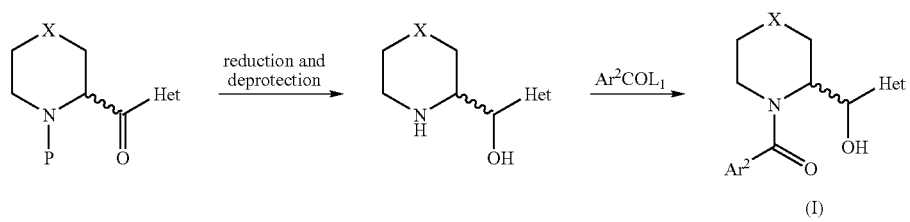

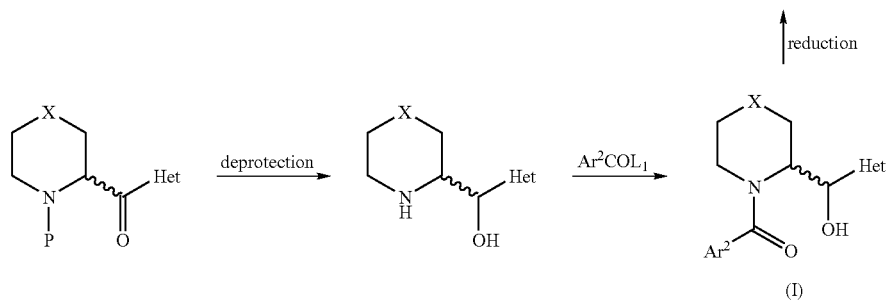

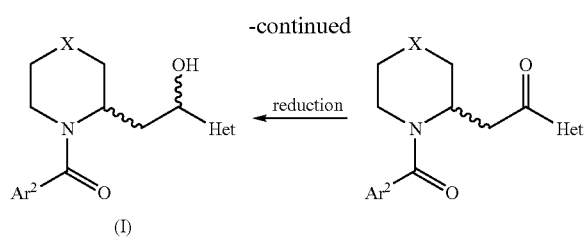

(I)

Wherein Het, X and Ar² are as defined for formula I, P is a protecting group and M is a metal for example lithium.

Within the schemes above there is scope for functional group interconversion; conversion of one compound of formula (I) to another of formula (I) by interconversion of substituents.

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable derivatives thereof.

Pharmaceutically acceptable salts may be prepared conventionally by reaction with the appropriate acid or acid derivative.

The compounds of formula (I) and their pharmaceutically acceptable derivatives are useful for the treatment of diseases or disorders where an antagonist of a human orexin receptor is required such as obesity and diabetes; prolactinoma; hypoprolactinemia; hypothalamic disorders of growth hormone deficiency; idiopathic growth hormone deficiency; Cushings syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; bulimia and hypopituitarism. The compounds of formula (I) or pharmaceutically acceptable derivatives thereof are also useful in the treatment of stroke, particular ischaemic or haemorrhagic stroke. Furthermore the compounds of formula (I) or pharmaceutically acceptable derivatives useful in the blocking an emetic response.

The compounds of formula (I) and their pharmaceutically acceptable derivatives are particularly useful for the treatment of obesity, including obesity associated with Type 2 diabetes, and sleep disorders. Additionally the compounds are useful in stroke and/or blocking the emetic response i.e. nausea and vomiting.

A further aspect of the invention is the use of

R)-1-[3,5-bis(trifluoromethyl)benzoyl]-2-(1H-indol-3-ylmethyl)piperazine;

(2R)-1-(3,5-dichlorobenzoyl)-2-[(1H-indol-3-yl)methyl]piperazine;

(2R)-2-[1H-indol-3-yl)methyl]-1-[3-methoxy-5-trifluoromethyl)benzoyl]piperazine; or 1-benzolyl-2-[1H-indol-3-yl)methyl]piperazine;

as an orexin antagonist.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The invention also provides a method of treating or preventing diseases or disorders where an antagonist of a human orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human orexin receptor is required.

The invention also provides the use of a compound of formula (I), or a pharmaceutically acceptable derivative thereof, in the manufacture of a medicament for the treatment or prophylaxis of diseases or disorders where an antagonist of a human orexin receptor is required.

A further aspect of the invention is the use of (2R)-1-[3,5-bis(trifluoromethyl)benzoyl]-2-(1H-indol-3-ylmethyl)piperazine in the manufacture of a medicament for the treatment or prophylaxis of diseases or disorders where an antagonist of a human orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical compositions adapted accordingly.

The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human orexin-A has the amino acid sequence:

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, *Drosophila* or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions D1-D 83 illustrate the preparation of intermediates to compounds of the invention.

In the Examples $^1$H NMR's were measured at 250 MHz in CDCl$_3$ unless otherwise stated.

The following abbreviations are used herein;

PyBop means benzotriazol-1-yloxytris(pyrrolidino)phosphonium hexafluorophosphate

```
pyroGlu Pro Leu Pro Asp Cys Cys Arg Gln Lys Thr Cys Ser Cys Arg Leu    (SEQ ID NO: 1)
   1           5                  10                  15

Tyr Glu Leu Leu His Gly Ala Gly Asn His Ala Ala Gly Ile Leu Thr
           20                  25                  30

Leu-NH₂
```

THF means tetrahyrdofuran

EDC.HCL means 1-(3-dimethylaminopropyl)-3-ethylcarbodiimide hydrochloride

HATU means O-(7-azabenzotriazol-1-yl)-N,N,N',N'-tetramethyluronium hexafluorophosphate TFA means trifluoroacetatic acid DMF means N,N-dimethylformamide DME means 1,2-dimethoxyethane

DESCRIPTION 1

(RS)-1-(tert-butyloxycarbonyl)-2-(N-methoxy-N-methylcarbamoyl)-piperidine

To (RS)-1-(tert-butyloxycarbonyl)-2-piperidine carboxylic acid (2.64 g, 11.5 mmol) in dichloromethane (10 ml) was added sequentially N,O-dimethyl hydroxylamine (1.34 g, 13.7 mmol), triethylamine (6 ml, 43.0 mmol) and Py.Bop (6.60 g, 12.7 mmol). The resultant mixture was stirred at ambient temperature for 6 h, then diluted with dichloromethane (170 ml) and poured into 1M HCl (22 ml). The organic phase was separated and washed with saturated aqueous sodium hydrogen carbonate (3×25 ml) and brine (25 ml) then evaporated in vacuo. The resultant colourless oil was chromatographed on silica gel eluting with 20% ethyl acetate in hexane to give the title compound (2.43 g, 77%) as a colourless oil.

Mass spectrum (API$^+$): Found 273 (MH$^+$). $C_{13}H_{24}N_2O_4$ requires 272.

DESCRIPTION 2

(RS)-2-(2-Benzofuranylcarbonyl)-1-(tert-butyloxycarbonyl)piperidine

To a solution of benzofuran (0.37 ml, 3.36 mmol) in THF (40 ml) at −35° C. was added nbutyllithium (1M in THF) (3.34 ml, 3.34 mmol) over 3 min. The resultant mixture was stirred for 10 min. at −35° C. then (RS)-1-(tert-butyloxycarbonyl)-2-(N-methoxy-N-methylcarbamoyl)-piperidine (1.0 g, 3.68 mmol) in THF (5 ml) was added over 1 min. and the resultant solution stirred for 15 min. at −35° C. The mixture was poured into saturated ammonium chloride (20 ml) and extracted with ethyl acetate (3×20 ml). The combined organics were washed with saturated aqueous sodium hydrogen carbonate (15 ml), then evaporated in vacuo. The resultant residue was chromatographed on silica gel eluting with 10% ethyl acetate in hexane to give the title compound (0.32 g, 26%) as a yellow solid.

Mass spectrum (API$^+$): Found 330 (MH$^+$) $C_{19}H_{23}NO_4$ requires 329.

DESCRIPTION 3

(RS)-2-(2-Benzofuranylmethyl)piperidine

To a solution of (RS)-2-(2-benzofuranylcarbonyl)-1-(tert-butyloxycarbonyl)piperidine (0.30 g, 0.91 mmol) in diethylene glycol (20 g), was added hydrazine hydrate (0.16 ml, 2.79 mmol) and the resultant mixture heated at 170° C. for 30 min. then cooled to room temperature. Potassium hydroxide (0.44 g, 7.86 mmol) was added and the mixture heated at 200° C. for 18 h. The resultant was then poured into water (100 ml) and extracted with diethyl ether (3×20 ml). The combined organic extracts were dried (Na$_2$SO$_4$) and evaporated in vacuo to give the title compound (10 mg, 36%) as a golden oil.

Mass spectrum (API$^+$). Found 216 (MH$^+$) $C_{14}H_{17}NO$ requires 215.

DESCRIPTION 4

(RS)-2-[(2-Hydroxy-phenylcarbamoyl)-methyl]-piperidine-1-carboxylic acid tert butyl ester A mixture of 2-carboxymethyl-piperidine-1-carboxylic acid tert butyl ester (0.97 g), (Peschke, Bernd; Ankersen, Michael; Hansen, Birgit Sehested; Hansen, Thomas Kruse; Johansen, Nils Langeland; Lau, Jesper; Madsen, Kjeld; Petersen, Hans; Thogersen, Henning; Watson, Brett. *Eur. J. Med. Chem.* (1999), 34(5), 363-380) in dimethylformamide (8.0 ml) was treated sequentially with EDC.HCl (0.76 g), 2-aminophenol (0.43 g) and 1-hydroxybenzotriazole (0.05 g). The mixture was stirred for 2 h, diluted with ethyl acetate and washed with water, dried (MgSO$_4$) and solvent removed at reduced pressure to give the title compound (1.29 g) as a gum.

Mass Spectrum (API$^+$): Found 335 (MH$^+$). $C_{18}H_{26}N_2O_4$ requires 334

DESCRIPTION 5

(RS)-2-Benzooxazol-2-ylmethyl-piperidine-1-carboxylic acid tert butyl ester (RS)-2-[(2-Hydroxy-phenylcarbamoyl)-methyl]-piperidine-1-carboxylic acid tert butyl ester (1.25 g), 4-toluenesulphonic acid (0.07 g) and 4-N,N-dimethylaminopyridine (0.023 g) were combined in 1,3-dichlorobenzene (30 ml) and the mixture boiled for 48 h. The mixture was diluted with dichloromethane and washed with water. The organic phase was dried (MgSO$_4$) and solvent removed at reduced pressure. The residue was column chromatographed (silica gel, 0→1% methanol in dichloromethane) to give the title compound (0.50 g)

Mass Spectrum (API$^+$): Found 317 (MH$^+$). $C_{18}H_{24}N_2O_3$ requires 316.

DESCRIPTION 6

(RS)-2-Piperidin-2-ylmethyl-benzooxazole (RS)-2-Benzooxazol-2-ylmethyl-piperidine-1-carboxylic acid tert butyl ester (0.50 g) in dichloromethane (8 ml) was cooled (ice-bath) and trifluoroacetic acid (2 ml) added. The mixture was stirred with ice-cooling for 4 h, poured onto saturated potassium carbonate (20 ml) and extracted with dichloromethane. The combined extracts were dried (MgSO$_4$) and solvent removed at reduced pressure to give the title compound (0.10 g)

Mass Spectrum (API$^+$): Found 217 (MH$^+$). $C_{13}H_{16}N_2O$ requires 216.

DESCRIPTION 7

(RS)-2-[1-(5-Fluoro-benzofuran-2-yl)methanoyl)-piperidine-1-carboxylic acid tert-butyl ester The title compound was prepared using the method of Description 2, from 5-fluorobenzofuran (1.36 g, 10 mmol, for preparation see WO99/51575), as a pale yellow solid (2.81 g, 84%)

$^1$H NMR δ: 1.20-1.60 (1H, m), 1.60-1.85 (2H, m), 1.90 (1H, broad m), 2.15-2.30 (1H, broad m), 3.20-3.40 (1H, broad m), 3.85-4.05 (1H, broad m), 5.20-5.70 (1H, broad m), 7.10-7.25 (1H, m), 7.25-7.4 (1H, d, J=7.4 Hz), 7.45-7.75 (2H, m).

DESCRIPTION 8

(RS)-2-(5-Fluoro-benzofuran-2-ylmethyl)-piperidine

The title compound was prepared using the method of Description 3, from (RS)-2-[1-(5-Fluoro-benzofuran-2-yl)methanoyl]-piperidine-1-carboxylic acid tert-butyl ester, D7 (1.21 g, 3.49 mmol), as a pale yellow gum (0.72 g, 89%).

Mass spectrum (API+): Found 234 (MH+) $C_{14}H_{16}FNO$ requires 233.

DESCRIPTION 9

(RS)-1-Benzofuran-2-yl-1-piperidin-2-yl-methanone

A solution of (RS)-2-(2-benzofuranylcarbonyl)-1-(tert-butyloxycarbonyl)piperidine, D2 (0.86 g, 2.61 mmol) in trifluoroacetic acid (5 ml) and dichloromethane (20 ml) was warmed at 35° C. for 0.5 h. The reaction mixture was evaporated in vacuo and the residue partitioned between dichloromethane (30 ml) and 1N sodium hydroxide (30 ml). The aqueous layer was extracted with dichloromethane (30 ml) and the combined organic layers dried ($Na_2SO_4$) and evaporated in vacuo to afford the title compound as a pale yellow gum (0.59 g, 99%).

Mass spectrum (API+): Found 230 (MH+). $C_{14}H_{15}NO_2$ requires 229.

DESCRIPTION 10

(RS)-2-(1-Furo[2,3-b]pyridin-2-yl)methanoyl-piperidine-1-carboxylic acid tert-butyl ester 2.5N n-Butyllithium in hexanes (2.3 ml, 5.75 mmol) was added dropwise over 10 min to a stirred solution of furo[2,3-b]pyridine (0.57 g, 4.79 mmol) (H. Sliwa, Bull. Soc. Chim. France, 646, 1970) in anhydrous THF (20 ml) at −75° C. under argon. The resultant mixture was stirred for 5 min at −70° C. then a solution of (RS)-1-(tert-butyloxycarbonyl)-2-1-methoxy-N-methylcarbamoyl)-piperidine, D1 (1.41 g, 5.19 mmol) in anhydrous THF (20 ml) was added over 2 min. and the resultant solution stirred at −70° C. for 15 min. The mixture was poured into saturated ammonium chloride (100 ml) and extracted with ethyl acetate (2×50 ml). The combined organics were dried ($Na_2SO_4$) and evaporated in vacuo. The residue was chromatographed on silica gel eluting with 0-1% ethyl acetate in dichloromethane to give the title compound as a colourless solid (0.51 g, 32%).

$^1$H NMR δ: 1.25-1.55 (11H, m), 1.60-1.80 (2H, m), 1.85-2.05 (1H, broad m), 2.15-2.40 (1H, broad m), 3.15-3.40 (1H, broad m), 3.80-4.15 (1H, broad m), 5.35-5.65 (1H, broad m), 7.30 (1H, broad m), 7.56 (1H, broad s), 8.08 (1H, broad m), 8.53 (1H, broad m).

DESCRIPTION 11

(RS)-2-Piperidin-2-ylmethyl-furo[2,3-b]pyridine

The title compound was prepared using the method of Description 3, from (RS)-2-(1-furo[2,3-b]pyridin-2-yl)methanoyl)piperidine-1-carboxylic acid tert-butyl ester, D10 (0.51 g, 1.55 mmol), as a light brown gum (0.26 g, 74%).

Mass spectrum (API+): Found 217 (MH+) $C_{13}H_{16}N_2O$ requires 216.

DESCRIPTION 12

(RS)-2-(1-Quinolin-2-yl-methanoyl)-piperidine-1-carboxylic acid tert-butyl ester 30% Potassium hydride dispersed in mineral oil (0.8 g, 6 mmol) was added to a stirred solution of 2-bromoquinoline (1.12 g, 5.29 mmol) (O. Sugimoto, Tet. Lett. 4, (1999), 7477-8) in anhydrous THF (20 ml) at −70° C. under argon. To this was added 2N n-butyllithium in hexanes (2.7 ml, 6.75 mmol) dropwise over 5 min. The resultant mixture was stirred for 10 min at −70° C. then a solution of (RS)-1-(tert-butyloxycarbonyl)-2-1-methoxy-N-methylcarbamoyl)-piperidine, D1 (1.57 g, 5.77 mmol) in anhydrous THF (10 ml) was added over 2 min. The cooling bath was removed and the reaction mixture allowed to warm to −20° C. and held at −20° C. for 10 min. The mixture was poured into saturated ammonium chloride (300 ml) and extracted with ethyl acetate (2×100 ml). The combined organics were dried ($Na_2SO_4$) and evaporated in vacuo. The residue was chromatographed on silica gel eluting with 0-10% ethyl acetate in pentane to yield the title compound as a pale yellow solid (1.2 g, 66%).

$^1$H NMR δ: 1.2-1.65 (12H, m), 1.65-1.85 (1H, m), 1.90-2.10 (1H, m), 2.20-2.50 (1H, m), 3.30-3.60 (1H, m), 3.85-4.20 (1H, m), 6.20-6.40 (1H, m), 7.50-7.90 (3H, m), 8.07 (1H, d, J=8.4 Hz), 8.18 (1H, d, J=8.8 Hz), 8.20-8.35 (1H, m).

DESCRIPTION 13

(RS)-2-Piperidin-2-ylmethyl-quinoline

The title compound was prepared using the method of Description 3, from (RS)-2-(1-quinolin-2-yl-methanoyl)-piperidine-1-carboxylic acid tert-butyl ester, D12 (1.2 g, 3.66 mmol), as a pale brown gum (0.053 g, 6%)

Mass spectrum (Electrospray LC/MS): Found 227 (MH+). $C_{15}H_{18}N_2$ requires 226.

DESCRIPTION 14

2-Amino-N,N-dimethyl-3-nitro-benzamide

EDC.HCl (2.47 g, 12.88 mmol) was added to a stirred mixture of 2-amino-3-nitrobenzoic acid (2.18 g, 11.98 mmol) (Mickelson, J. Med. Chem, 39(23) 4662 (1996)), 2M dimethylamine in THF (6.45 ml, 12.9 mmol) and 1-hydroxybenzotriazole (0.1 g, 0.74 mmol) in dichloromethane (100 ml). The reaction mixture was stirred at room temperature for 18 h, washed with saturated aqueous sodium bicarbonate and the organic layer dried ($Na_2SO_4$) and evaporated in vacuo to afford the title compound as a pale orange gum (2.5 g, 100%).

$^1$H NMR δ: 3.08 (6H, s), 6.70 (1H, m), 6.85 (2H, broad s), 7.33 (1H, dd, J=2 and 8 Hz), 8.2 (1H, dd, J=2 and 8 Hz).

DESCRIPTION 15

3-Dimethylaminomethyl-benzene-1,2-diamine

1M Lithium aluminium hydride in THF (18.1 ml, 18.1 mmol) was added dropwise over 5 min. to a stirred, ice cooled solution of 2-Amino-N,N-dimethyl-3-nitro-benzamide, D14 (1.26 g, 6.03 mmol) in anhydrous THF (40 ml) under argon. The reaction mixture was stirred at 0° C. for 0.5 h then at room temperature for a further 2 h before being recooled in ice, as water (3.2 ml), 2N sodium hydroxide (3.6 ml) and water (3.2 ml) were added dropwise sequentially. The mixture was stirred for 10 min, solid $Na_2SO_4$ added and stirring continued for 10 min. Solids were filtered, washed with ethyl acetate and the combined organics evaporated in vacuo to give the title compound as an orange solid (0.9 g, 91%).

$^1$H NMR δ: 2.19 (6H, s), 3.29 (2H, broad s), 3.42 (2H, s), 4.50 (2H, broad s), 6.50-6.80 (3H, m).

DESCRIPTION 16

(RS)-(1-{1-[5-(4-Fluoro-phenyl)-2-methyl-thiazol-4-yl]-methanoyl}-piperidin-2-yl)-acetic acid methyl ester A stirring solution of 5-(4-fluoro-phenyl)-2-methyl-thiazole-4-carboxylic acid (3.00 g, 12.5 mmol) in DMF (50 ml), under argon was treated sequentially with N,N-diisopropylethylamine (6.8 ml), HATU (4.77 g, 12.5 mmol) then after stirring for 0.25 h, piperidin-2-yl-acetic acid methyl ester (Beckett et al, J. Med. Chem., 563, 1969) (1.83 g, 12.5 mmol) was added. The mixture was stirred for 16 h at room temperature and was then diluted with water. The product was extracted into diethyl ether. The organic phase was washed with water (3×) and brine, was dried (MgSO$_4$) and the solvent removed in vacuo to afford the title compound as a yellow gum (4.00 g, 85%).

Mass spectrum (API$^+$). Found 377 (MH$^+$). $C_{19}H_{21}FN_2O_3S$ requires 376.

DESCRIPTION 17

(RS)-(1-{1-[5-(4-Fluoro-phenyl)-2-methyl-thiazol-4-yl]-methanoyl}-piperidin-2-yl)-acetic acid A stirring solution of (1-{1-[5-(4-Fluoro-phenyl)-2-methyl-thiazol-4-yl]-methanoyl}-piperidin-2-yl)-acetic acid methyl ester, D16 (4.00 g, 10.6 mmol) in methanol/water (75 ml/25 ml) was treated with sodium hydroxide (0.85 g, 21.3 mmol). The mixture was stirred for 16 h at room temperature. The methanol was removed in vacuo and the residue was diluted with water and extracted with diethyl ether (2×). The aqueous phase was acidified with 5N HCl and the product was extracted with ethyl acetate. The organic phase was dried (MgSO$_4$) and the solvent removed in vacuo. The residue was triturated with pentane to afford the title compound as a white solid (3.10 g, 82%).

$^1$H NMR (D$_6$-DMSO) δ: 0.98 (0.6H, m), 1.15-1.70 (5.4H, bm), 2.18 (0.4H, dd), 2.38 (0.6H, dd, J=6 and 15 Hz), 2.70 (4.4H, m), 2.93 (0.6H, m), 3.17 (0.6H, d, J=12 Hz), 3.94 (0.4H, m), 4.40 (0.4H, d, J=12 Hz), 5.05 (0.6H, m), 7.27 (2H, m), 7.47 (2H, m), 12.20 (1H, bs).

DESCRIPTION 18

(RS)-5,6-Difluoro-2-piperidin-2-ylmethyl-1H-benzoimidazole

A mixture of 2-carboxymethyl-piperidine-1-carboxylic acid tert-butyl ester (Beckett et al, J. Med. Chem., 563, 1969) (10.0 g, 41 mmol) and 4,5-difluoro-benzene-1,2-diamine (5.95 g, 41 mmol) in polyphosphoric acid (140 g) was heated at 140° C. for 7 h. The cooled reaction mixture was poured onto excess solid potassium carbonate and crushed ice. The resulting basic, aqueous solution was extracted with ethyl acetate (2×) and the combined organics were washed with brine, dried (Na$_2$SO$_4$) and the solvent removed in vacuo. The residue was triturated with diethyl ether, ethyl acetate and pentane to afford the title compound as a light brown solid (7.14 g, 69%).

$^1$H NMR (D$_6$-DMSO) δ: 1.08 (1H, m), 1.27 (2H, m), 1.50 (2H, m), 1.70 (1H, m), 2.48 (1H, m, obscured by DMSO), 2.78 (2H, d, J=7 Hz), 2.88 (2H, m), 7.51 (2H, app. t, J=6 Hz).

DESCRIPTION 19

(RS)-2-(5,6-Difluoro-1H-benzoimidazol-2-ylmethyl)-piperidine-1-carboxylic acid tert-butyl ester 4,5-Difluoro-benzene-1,2-diamine (1.00 g, 6.9 mmol) and 2-carboxymethyl-piperidine-1-carboxylic acid tert-butyl ester (Beckett et al, J. Med. Chem., 563, 1969) (1.69 g, 6.9 mmol) were heated at 120° C. with stirring, under argon for 4 h. A further portion of 2-carboxymethyl-piperidine-1-carboxylic acid tert-butyl ester (0.85 g) was added and heating was continued for a further 2 h. The cooled reaction mixture was diluted with ethyl acetate, washed with saturated aqueous sodium bicarbonate (2×) and brine, dried (MgSO$_4$) and the solvent removed in vacuo. The residue was chromatographed (silica gel, 0-30% ethyl acetate-pentane) to give a yellow solid which was triturated with diethyl ether to afford the title compound as a pale brown solid (0.38 g, 15%).

Mass spectrum (API$^+$). Found 352 (MH$^+$) $C_{18}H_{23}F_2N_3O_2$ requires 351.

DESCRIPTION 20

(RS)-5,6-Difluoro-2-piperidin-2-ylmethyl-1H-benzoimidazole. 2HCl

A stirring solution of 2-(5,6-Difluoro-1H-benzoimidazol-2-ylmethyl)-piperidine-1-carboxylic acid tert-butyl ester, D19 (375 mg, 1.1 mmol) in MeOH (20 ml) was treated with 1M HCl in 1,4-dioxane (5 ml). After stirring under argon at room temperature for 5 h the volatiles were removed in vacuo to afford the title compound as a gum (100%).

Mass spectrum (API$^+$). Found 252 (MH$^+$) $C_{13}H_{15}F_2N_3$ requires 251.

DESCRIPTION 21

(RS)-4,5-Difluoro-2-piperidin-2-ylmethyl-1H-benzoimidazole

A mixture of 2-carboxymethyl-piperidine-1-carboxylic acid tert-butyl ester (Beckett et al, J. Med. Chem., 563, 1969) (6.72 g, 28 mmol) and 3,4-difluoro-benzene-1,2-diamine (4.00 g, 28 mmol) in polyphosphoric acid (130 g) was heated at 140° C. for 7.5 h. The cooled reaction mixture was poured onto excess solid potassium carbonate and crushed ice. The resulting basic, aqueous solution was extracted with ethyl acetate (2×) and the combined organics were washed with brine, dried (Na$_2$SO$_4$) and the solvent removed in vacuo. The residue was triturated with diethyl ether, ethyl acetate and pentane to afford the title compound as a white solid (4.29 g, 62%).

$^1$H NMR (D$_6$-DMSO) δ: 1.08 (1H, m), 1.28 (2H, m), 1.50 (2H, m), 1.72 (1H, m), 2.46 (1H, m, obscured by DMSO), 2.81 (2H, d, J=7 Hz), 2.90 (2H, m), 7.14 (1H, m), 7.24 (1H, m).

DESCRIPTION 22

1-(2-Dimethylamino-ethyl)-4-(4-fluoro-phenyl)-1H-pyrazole-3-carboxylic acid ethyl ester 4-(4-Fluoro-phenyl)-1H-pyrazole-3-carboxylic acid ethyl ester (2.4 g, 10 mmol) was added to an ice-cooled slurry of sodium hydride (0.82 g, 60% dispersion in mineral oil, 20 mmol) in DMF (20 ml), under argon. N,N-diisopropylethylamine (1.8 ml, 10 mmol) was added followed by 2-chloroethyl dimethylamine.HCl (1.48 g, 10 mmol) and potassium iodide (5 mg). The reaction mixture was stirred at room temperature for 16 h then at 80° C. for 48 h. 2N HCl and water were added and the product extracted with ethyl acetate (3×). The combined organics were washed with brine, dried ($Na_2SO_4$) and the solvent removed in vacuo. Chromatography (silica gel, 3-10% methanol-dichloromethane) afforded 2-(2-dimethylamino-ethyl)-4-(4-fluoro-phenyl)-1H-pyrazole-3-carboxylic acid ethyl ester (900 mg) and the title compound (630 mg).

$^1$H NMR δ: 1.31 (3H, t. J=7 Hz), 2.29 (6H, s), 2.80 (2H, t, J=6 Hz), 4.30 (4H, m), 7.05 (2H, m), 7.44 (2H, m), 7.56 (1H, s).

DESCRIPTION 23

1-(2-Dimethylamino-ethyl)-4-(4-fluoro-phenyl)-1H-pyrazole-3-carboxylic acid

A solution of 1-(2-Dimethylamino-ethyl)-4-(4-fluoro-phenyl)-1H-pyrazole-3-carboxylic acid ethyl ester, D22 (610 mg, 2 mmol) in methanol/water (15 ml/10 ml) was treated with 2N sodium hydroxide (4 ml). After stirring at room temperature for 16 h the methanol was removed in vacuo and the residue treated with 2N HCl (4 ml). The water was removed in vacuo. Dichloromethane was added to the residue and the inorganic solid was removed by filtration. Removal of the solvent form the filtrate in vacuo afforded the title compound as a white solid (350 mg, 63%).

Mass spectrum (API$^+$). Found 278 (MH$^+$) $C_{14}H_{16}FN_3O_2$ requires 277.

DESCRIPTION 24

5-(4-Fluoro-phenyl)-2-methyl-2H-[1,2,3]triazole-4-carboxylic acid methyl ester 5-(4-Fluoro-phenyl)-2H-[1,2,3]triazole-4-carboxylic acid methyl ester (2.21 g, 10 mmol) in THF (10 ml) was added drop-wise to an ice-cooled slurry of sodium hydride (0.42 g, 60% dispersion in mineral oil, 10 mmol) in THF (45 ml), under argon. After stirring at room temperature for 1 h, the reaction mixture was heated at 80° C. for 16 h. Water was added to the cooled mixture and the product was extracted with diethyl ether (2×). The combined organics were washed with brine, dried ($Na_2SO_4$) and the solvent removed in vacuo. Chromatography (silica gel, 10-50% ethyl acetate-pentane) afforded 5-(4-Fluoro-phenyl)-1-methyl-2H-[1,2,3]triazole-4-carboxylic acid methyl ester (763 mg, 33%) and the title compound (943 mg, 40%).

$^1$H NMR δ: 3.94 (3H, s), 4.29 (3H, s), 7.13 (2H, m), 7.87 (2H, m).

DESCRIPTION 25

5-(4-Fluoro-phenyl)-2-methyl-2H-[1,2,3]triazole-4-carboxylic acid 5-(4-Fluoro-phenyl)-2-methyl-2H-[1,2,3]triazole-4-carboxylic acid methyl ester D24 (940 mg, 4 mmol) in water (65 ml) was treated with 2N sodium hydroxide (4 ml) and the mixture was heated at 120° C. for 2 h. The volume of water was reduced to 20 ml in vacuo and the ice-cooled residue was treated with 2N HCl (4 ml). Filtration, washing with water and drying in vacuo afforded the title compound as a white solid (810 mg, 91%).

Mass spectrum (API$^+$). Found 222 (MH$^+$) $C_{10}H_8FN_3O_2$ requires 221.

DESCRIPTION 26

(S)-Pyrrolidin-2-ylmethyl-1H-benzoimidazole

A mixture of benzene-1,2-diamine (0.235 g, 2.2 mmol) and (S)-2-carboxymethyl-pyrrolidine-1-carboxylic acid tert-butyl ester (0.500 g, 2.2 mmol) in polyphosphoric acid (10 g) was heated under argon at 140° C. for 4 h then at 160° C. for 20 h. The reaction mixture was cooled and partitioned between aqueous saturated potassium carbonate and dichloromethane. The aqueous phase was extracted with 9-1 dichloromethane-methanol (4×). The combined organics were dried ($MgSO_4$) and the solvent removed in vacuo to afford the title compound as a pale brown foam (0.328 g) contaminated with 9% starting diamine.

$^1$H NMR δ: 1.30-2.10 (4H, bm), 2.80-3.60 (6H, bm incl. NH), 7.20 (1H, m), 7.55 (1H, m).

DESCRIPTION 27

(S)-5,6-Difluoro-pyrrolidin-2-ylmethyl-1H-benzoimidazole

A mixture of 4,5-difluorobenzene-1,2-diamine (0.360 g, 2.5 mmol) and (S)-2-carboxymethyl-pyrrolidine-1-carboxylic acid tert-butyl ester (0.570 g, 2.5 mmol) in polyphosphoric acid (9.5 g) was heated under argon at 160° C. for 20 h. The reaction mixture was cooled and partitioned between aqueous saturated potassium carbonate and dichloromethane. The aqueous phase was extracted with 9-1 dichloromethane-methanol (4×). The combined organics were dried ($MgSO_4$) and the solvent removed at reduced pressure to afford the title compound as a pale brown foam (0.394 g).

Mass Spectrum (API$^+$): Found 236 (M-H). $C_{12}H_{13}F_2N_3$ requires 237.

DESCRIPTION 28

(RS)-[1-(2,2,2-Trifluoroethanoyl)-piperidin-2-yl] acetic acid ethyl ester (RS)-Piperidin-2-yl acetic acid ethyl ester (Rhodes et al, J. Am. Pharm. Assoc., 1956, 45, 746) (6.0 g) was dissolved in dry dichloromethane (60 ml) and cooled to −10° C. under an atmosphere of argon. Triethylamine (5.0 ml), followed by trifluoroacetic anhydride (5.1 ml) was added to the stirred solution and stirring was continued at room temperature for 16 h. The reaction solution was then partitioned between dichloromethane and saturated sodium bicarbonate solution. The organic solution was dried ($MgSO_4$) and the solvent removed in vacuo to yield the title compound as an oil (4.2 g).

Mass Spectrum (API$^+$): Found 268 (MH$^+$). $C_{11}H_{16}F_3NO_3$ requires 267.

DESCRIPTION 29

(R,S)-1-(2-Benzothiazol-2-ylmethylpiperidin-1-yl)-2,2,2-trifluoro-ethanone

[1-(2,2,2-Trifluoroethanoyl)piperidin-2-yl]acetic acid ethyl ester, D28 (1.34 g) and 2-aminothiophenol (1.50 g) were suspended in polyphosphoric acid (30 ml) and heated to 90° C. for 2 h with vigorous stirring. After cooling, the reaction mixture was poured into iced water and stirred vigorously for 1 h. The aqueous solution was then extracted several times with ethyl acetate. After drying (MgSO$_4$), the solvent was removed in vacuo and the residue chromatographed (silica gel) to afford the title compound as an oil (1.2 g).

Mass Spectrum (API$^+$): Found 329 (MH$^+$). $C_{15}H_{15}F_3N_2SO$ requires 328.

DESCRIPTION 30

(RS)-2-Piperidin-2-ylmethylbenzothiazole 1-(2-Benzothiazol-2-ylmethylpiperidin-1-yl)-2,2,2-trifluoroethanone, D29 (1.2 g) was dissolved in methanol (40 ml) and 2N sodium hydroxide solution (20 ml) and heated to 50° C. for 0.75 h. After cooling, the reaction solution was partitioned between dichloromethane and water. The organic solution was dried (MgSO$_4$) and the solvent removed in vacuo. The residue was chromatographed (silica gel, 0-10% [9:1 MeOH/conc. ammonia solution] in dichloromethane) to afford the title compound (0.68 g).

Mass Spectrum (API$^+$): Found 233 (MH$^+$). $C_{13}H_{16}N_2S$ requires 232.

DESCRIPTION 31

(RS)-1-Benzyl-2-bromomethylpiperidine (RS)-(1-Benzyl-piperidin-2-yl)-methanol (R. Sreekumar et al, Tetrahedron Lett., 1998, 39 5151) (10.0 g) was converted to the title compound (5.2 g) by treatment with triphenylphosphine (13.0 g) and N-bromosuccinimide (9.4 g) in dichloromethane using literature procedures, (Tetrahedron Lett, 1999, 40, 7477-8).

Mass Spectrum (API$^+$): Found 270 (MH$^+$). $C_{13}H_{18}^{81}BrN$ requires 269.

DESCRIPTION 32

(RS)-1-Benzyl-2-cyanomethylpiperidine (RS)-1-Benzyl-2-bromomethylpiperidine, D31 (4.2 g) was dissolved in dry dimethylsulphoxide (15 ml) and treated with sodium cyanide (5.0 g). The solution was then stirred at 85° C. under argon for 18 h. The reaction solution was then poured into water (300 ml) and extracted with dichloromethane (2×200 ml). The organic solution was dried (MgSO$_4$) and the solvent removed in vacuo. Chromatography (silica gel, diethyl ether/petroleum ether mixtures) afforded the title compound (3.3 g).

Mass Spectrum (API$^+$): Found 215 (MH$^+$). $C_{14}H_{18}N_2$ requires 214.

DESCRIPTION 33

(RS)-2-(1-Benzylpiperidin-2-ylmethyl)-[1,2,4]-triazolo[1,5-a]pyridine (RS)-1-Benzyl-2-cyanomethylpiperidine, D32 (1.0 g) was dissolved in dry tetrahydrofuran (10 ml) containing ethanol (0.28 ml). The reaction solution was then cooled to ice bath temperature and hydrogen chloride gas was bubbled through the solution for 1 h. The solution was then stirred at room temperature for 16 h. The resulting solution was diluted with tetrahydrofuran (30 ml) and dichloromethane (30 ml) and 1-aminopyridinium iodide (1.0 g), followed by excess potassium carbonate and ethanol (30 ml) was added. The reaction mixture was then stirred at room temperature under argon for 24 h. The mixture was then filtered and the solvent removed in vacuo. The residue was chromatographed (silica gel, 80-20 diethyl ether-petroleum ether then 9-1 dichloromethane-methanol) to afford the title compound.

Mass Spectrum (API$^+$): Found 307 (MH$^+$). $C_{14}H_{18}N_2$ requires 306.

DESCRIPTION 34

(RS)-2-Piperidin-2-ylmethyl-5,6,7,8-tetrahydro-[1,2,4]-triazolo[1,5-a]pyridine and 2-Piperidin-2-ylmethyl-[1,2,4]-triazolo[1,5-a]pyridine (RS)-2-(1-Benzylpiperidin-2-ylmethyl)-[1,2,4]-triazolo[1,5-a]pyridine, D33 (0.200 g) was dissolved in ethanol (25 ml). Palladium hydroxide (0.100 g), followed by platinum IV sulphide (0.020 g) were added and the reaction mixture hydrogenated at 50 psi and 50° C. for 16 h. The suspension was evaporated to yield a mixture of the title compounds (0.180 g).

DESCRIPTION 35

(RS)-2-[(Methoxy-methyl-carbamoyl)-methyl]-piperidine-1-carboxylic acid tert-butyl ester A solution of 2-carboxymethyl-piperidine-1-carboxylic acid tert-butyl ester (Beckett et al, J. Med. Chem., 563, 1969) (2.29 g, 10 mmol) in DMF (20 ml) was treated sequentially with N,N-diisopropylethylamine (4.0 ml), HATU (3.8 g, 10 mmol) and O,N-dimethyl-hydroxylamine.HCl (0.98 g, 10 mmol). The reaction mixture was stirred under argon at room temperature for 16 h. The volatiles were removed in vacuo and the residue was chromatographed (silica gel, diethyl ether) to afford the title compound as a white solid (2.60 g, 90%).

Mass Spectrum (API$^+$): Found 187 (MH$^+$—$^t$BOC). $C_{14}H_{26}N_2O_4$ requires 286.

DESCRIPTION 36

(RS)-2(2-Benzofuran-2-yl-2-oxo-ethyl)-piperidine-1-carboxylic acid tert-butyl ester To a solution of benzofuran (0.95 g, 8.0 mmol) in THF (40 ml), under argon at −40° C. was added n-butyllithium (2.5M in hexanes) (4.00 ml, 10.0 mmol) over 5 min. The resultant mixture was stirred for 15 min. at −40° C. then (RS)-2-[(methoxy-methyl-carbamoyl)-methyl]-piperidine-1-carboxylic acid tert-butyl ester, D35 (2.30 g, 8.0 mmol) in THF (10 ml) was added over 1 min. and the resultant solution stirred for 20 min. at −40° C. The mixture was poured into saturated ammonium chloride (20 ml) and extracted with ethyl acetate (3×). The combined organics were dried (MgSO$_4$) and the solvent removed in vacuo. The resultant residue was chromatographed (silica gel, dichloromethane) to afford the title compound (2.2 g, 84%).

$^1$H NMR δ: 1.35 (9H, s), 1.44 (1H, m), 1.65 (5H, m), 2.94 (1H, dt, J=3 and 13 Hz), 3.17 (2H, m), 4.05 (1H, broad d), 4.89 (1H, m), 7.31 (1H, t, J=8 Hz), 7.48 (1H, m), 7.57 (2H, m), 7.72 (1H, d, J=8 Hz).

DESCRIPTION 37

(RS)-1-Benzofuran-2-yl-2-piperidin-2-yl-ethanone

A stirring solution of (RS)-2(2-benzofuran-2-yl-2-oxo-ethyl)-piperidine-1-carboxylic acid tert-butyl ester, D36 (1.68 g, 4.9 mmol) in dichloromethane (20 ml) was treated with trifluoroacetic acid (5 ml). The mixture was stirred at 50° C. for 1 h, cooled and the volatiles removed in vacuo.

The residue was dissolved in dichloromethane and washed with saturated sodium bicarbonate, dried (MgSO$_4$) and the solvent removed in vacuo to afford the title compound (1.20 g, 99%).

Mass Spectrum (API$^+$): Found 244 (MH$^+$). $C_{15}H_{17}NO_2$ requires 243.

DESCRIPTION 38

(RS)-1-Benzofuran-2-yl-2-(1-{1-[5-(4-fluoro-phenyl)-2-methyl-thiazol-4-yl]-methanoyl}-piperidin-2-yl)-ethanone The title compound was prepared from 5-(4-fluoro-phenyl)-2-methyl-thiazole-4-carboxylic acid
and (RS)-1-benzofuran-2-yl-2-piperidin-2-yl-ethanone, D37 according to a procedure similar to that for Description 35.

Mass Spectrum (API$^+$): Found 463 (MH$^+$). $C_{26}H_{23}FN_2O_3S$ requires 462.

DESCRIPTION 39

(RS)-4-Bromo-2-piperidin-2-ylmethyl-1H-benzimidazole

The title compound was prepared using the method of Description 18 from 3-bromobenzene-1,2-diamine (0.50 g, 2.7 mmol) and 2-carboxymethyl-piperidine-1-carboxylic acid tert-butyl ester (0.65 g, 2.7 mmol), as a pale brown amorphous solid (0.70 g, 88%)

Mass spectrum (Electrospray LC/MS): Found M-H 292. $C_{13}H_{16}{}^{79}BrN_3$ requires 293.

DESCRIPTION 40

(RS)-1-(2-Benzofuran-2-ylmethyl-piperidin-1-yl)-2,2,2-trifluoro-ethanone

To (RS)-2-(2-Benzofuranylmethyl)piperidine, D3 (500 mg, 2.3 mmol) in dichloromethane containing triethylamine (0.35 ml, 2.5 mmol) at 0° C. under argon was added trifluoroacetic anhydride (0.36 ml, 2.5 mmol) in dichloromethane (3 ml) over 5-10 min. The reaction was stirred at room temperature for 64 h, diluted with dichloromethane and washed sequentially with water and saturated sodium hydrogen carbonate, dried (Na$_2$SO$_4$) and the solvent removed in vacuo. Chromatography (silica gel) afforded the title compound as a solid (740 mg, 99%).

$^1$H NMR δ: 1.50-1.90 (6H, m), 2.90-3.20 (2H, m), 3.27-3.35 (1H, m), 3.85-3.89 (0.66H, m), 4.51-4.54 (0.66H, m), 5.09-5.14 (0.66H, m), 6.48 and 6.50 (1H, s), 7.15-7.25 (2H, m), 7.39-7.45 (1H, m), 7.45-7.50 (1H, m).

DESCRIPTION 41

(RS)-1-(2-(3-Bromo-benzofuran-2-ylmethyl-piperidin-1-yl)-2,2,2-trifluoro-ethanone To a solution of (RS)-1-(2-benzofuran-2-ylmethyl-piperidin-1-yl)-2,2,2-trifluoro-ethanone, D40 (700 mg, 2.2 mmol) in diethyl ether (10 ml) at −12° C. under argon was added a solution of bromine (360 mg, 2.2 mmol) in dichloromethane (4 ml) drop-wise over 0.3 h. The reaction mixture was allowed to reach room temperature and after 1 h the volatiles were removed in vacuo. Re-evaporation from dichloromethane (3×) afforded the title compound as a solid (840 mg, 96%).

Mass spectrum (Electrospray LC/MS): Found 310 (MH$^+$—Br). $C_{16}H_{15}{}^{79}BrF_3NO_2$ requires 389.

DESCRIPTION 42

(RS)-2-(1-(2,2,2-Trifluoro-ethanoyl)-piperidin-2-ylmethyl)-benzofuran-3-carbonitrile To a solution of (RS)-1-(2-(3-bromo-benzofuran-2-ylmethyl-piperidin-1-yl)-2,2,2-trifluoro-ethanone, D41 (840 mg, 2.1 mmol) in N-methylpyrrolidinone (15 ml) was added copper(I)cyanide (387 mg, 4.2 mmol) and the mixture refluxed for 4.5 h. The reaction mixture was cooled and diluted with water (100 ml), 0.880 ammonia (3 ml) and ethyl acetate (3×). The combined extracts were dried (Na$_2$SO$_4$) and the solvent removed in vacuo. The residual oil was redissolved in ethyl acetate (75 ml) and washed with water (4×), brine, dried (Na$_2$SO$_4$) and the solvent removed in vacuo. Chromatography (silica gel) afforded the title compound as a solid.

Mass spectrum (Electrospray LC/MS): Found 337 (MH$^+$). $C_{17}H_{15}F_3N_2O_2$ requires 336.

DESCRIPTION 43

(RS)-Morpholin-3-yl-acetic acid ethyl ester

N-chloromorpholine (24 g) in diethyl ether (20 ml) was added drop-wise over 2.5 h to a vigorously stirred solution of potassium hydroxide (22.1 g, 0.37 mol) in ethanol (130 ml) at 90° C. Heating was continued at 80° C. for 2 h. After standing at room temperature for 48 h the mixture was filtered to remove the inorganics and the solvent removed from the filtrate in vacuo. The residue was partitioned between diethyl ether and brine, dried (Na$_2$SO$_4$) and the solvent removed in vacuo. The resulting brown oil was dissolved in acetonitrile (100 ml). Triethylamine (25 ml) and monoethyl malonate (25 g) were added and the mixture heated at 16° C. for 16 h. The volatiles were removed in vacuo and the residue partitioned between saturated aqueous potassium carbonate and diethyl ether. The organic phase was dried (Na$_2$SO$_4$) and the solvent removed in vacuo to afford the title compound as a brown oil (3.5 g).

Mass Spectrum (API$^+$): Found 174 (MH$^+$). $C_8H_{15}NO_3$ requires 173.

DESCRIPTION 44

(RS)-(4-{1-[5-(4-Fluoro-phenyl)-2-methyl-thiazol-4-yl]-methanoyl}-morpholin-3-yl)-acetic acid ethyl ester The title compound (1.48 g, 66%) was prepared from (RS)-morpholin-3-yl-acetic acid ethyl ester, D43 (1.37 g, 5.8 mmol) and 5-(4-fluoro-phenyl)-2-methyl-thiazole-4-carboxylic acid (1.00 g, 5.8 mmol) according to a procedure similar to that described for D16.

Mass spectrum (Electrospray LC/MS): Found 393 (MH$^+$). $C_{19}H_{21}FN_2O_4S$ requires 392.

DESCRIPTION 45

(RS)-(4-{1-[5-(4-Fluoro-phenyl)-2-methyl-thiazol-4-yl]-methanoyl}-morpholin-3-yl)-acetic acid The title compound (1.33 g, 99%) was prepared from (RS)-(4-{1-[5-(4-Fluoro-phenyl)-2-methyl-thiazol-4-yl]-methanoyl}-morpholin-3-yl)-acetic acid ethyl ester, D44 (1.46 g, 3.7 mmol) according to a procedure similar to that described for D17.

Mass Spectrum (API$^+$): Found 363 (M-H). $C_{17}H_{17}FN_2O_4S$ requires 364.

DESCRIPTION 46

(RS)-2-(1-Furo[3,2-b]pyridin-2-yl)methanoyl)piperidine-1-carboxylic acid tert-butyl ester The title compound was prepared using the method of Description 10 from furo[3,2-b]pyridine (1.14 g, 9.6 mmol) (Shiotani and Morita, *J. Het. Chem.*, 23, 665, 1986), as a pale yellow solid (1.97 g, 62%).

Mass Spectrum (API$^+$): Found 331 (MH$^+$). $C_{18}H_{22}N_2O_4$ requires 330.

DESCRIPTION 47

(RS)-2-Piperidin-2-ylmethyl-furo[3,2-b]pyridine

The title compound was prepared using the method of Description 3 from (RS)-2-(1-furo[3,2-b]pyridin-2-yl)methanoyl)piperidine-1-carboxylic acid tert-butyl ester, D46 (1.95 g, 5.9 mmol), as a pale green gum (0.75 g, 59%).

Mass Spectrum (API$^+$): Found 217 (MH$^+$). $C_{13}H_{16}N_2O$ requires 216.

DESCRIPTION 48

(RS)-2-[1-(5-Fluorobenzofuran-2-yl)-methanoyl]-piperazine-1,4-dicarboxylic acid 1-benzyl ester 4-tert-butyl ester The title compound was prepared from (RS)-2-(methoxymethylcarbamoyl)piperazine-1,4-dicarboxylic acid 1-benzyl ester 4-tert-butyl ester (1.25 g, 3.07 mmol) (WO01/00214) and 5-fluorobenzofuran (0.42 g, 3.09 mmol) (WO99/51575) by the method of Description 2 as a pale green gum (0.81 g, 55%).

Mass spectrum (API$^+$): Found 505 (MNa$^+$). $C_{26}H_{27}FN_2O_6$ requires 482.

DESCRIPTION 49

(RS)-2-[1-(5-Fluoro-benzofuran-2-yl)methanoyl]-piperazine-1-carboxylic acid benzyl ester The title compound was prepared from (RS)-2-[1-(5-fluorobenzofuran-2-yl)-methanoyl]-piperazine-1,4-dicarboxylic acid 1-benzyl ester 4-tert-butyl ester, D48 (0.81 g, 1.68 mmol) by the method of Description 52 as a pale yellow amorphous solid (0.57 g, 90%).

Mass spectrum (API$^+$): Found 383 (MH$^+$). $C_{21}H_{19}FN_2O_4$ requires 382.

DESCRIPTION 50

(RS)-2-[1-(5-Fluoro-benzofuran-2-yl)methanoyl]-4-methyl-piperazine-1-carboxylic acid benzyl ester 97% Formic acid (0.19 g, 4 mmol) was added to a stirred mixture of (RS)-2-[1-(5-fluoro-benzofuran-2-yl)methanoyl]-piperazine-1-carboxylic acid benzyl ester, D49 (0.57 g, 1.5 mmol) in water (5 ml). Stirring was continued as a 37% formaldehyde solution in water (0.155 g) was added. The resultant mixture was heated at 100° C. for 3.5 h, cooled, diluted with water (30 ml) and basified with 2N sodium hydroxide. The mixture was extracted with ethyl acetate (2×) and the combined extracts dried (Na$_2$SO$_4$) and the solvent removed in vacuo to afford the title compound (0.57 g, 96%).

Mass spectrum (API$^+$): Found 397 (MH$^+$). $C_{22}H_{21}FN_2O_4$ requires 396.

DESCRIPTION 51

(RS)-3-(5-Fluorobenzofuran-2-ylmethyl)-1-methylpiperazine

The title compound was prepared from (RS)-2-[1-(5-fluoro-benzofuran-2-yl)methanoyl]-4-methyl-piperazine-1-carboxylic acid benzyl ester, D50 using the method of Description 3 as a yellow gum (0.43 g).

Mass spectrum (API$^+$): Found 249 (MH$^+$). $C_{14}H_{17}FN_2O$ require 248.

DESCRIPTION 52

(RS)-2-(Methoxy-methyl-carbamoyl)-piperazine-1-carboxylic acid benzyl ester

A mixture of (RS)-2-(methoxy-methyl-carbamoyl)-piperazine-1,4-dicarboxylic acid 1-benzyl ester 4-tert-butyl ester (WO 01/00214) (5 g, 0.012 mol) in dichloromethane (100 ml) and trifluoroacetic acid (20 ml) was heated at 40° C. for 0.5 h, cooled and evaporated. The residual oil was dissolved in dichloromethane (150 ml) and washed with 1M sodium hydroxide (80 ml). The aqueous phase was re-extracted with dichloromethane (2×) and the combined extracts dried (Na$_2$SO$_4$) and the solvent removed in vacuo to give the title compound as an oil (3.6 g, 100%).

Mass spectrum (API$^+$): Found 308 (MH$^+$). $C_{15}H_{21}N_3O_4$ requires 307.

DESCRIPTION 53

(RS)-2-(Methoxy-methyl-carbamoyl)-4-methyl-piperazine-1-carboxylic acid benzyl ester To (RS)-2-(methoxy-methyl-carbamoyl)-piperazine-1-carboxylic acid benzyl ester, D52 (3 g, 10 mmol) in 1,2-dichloroethane (50 ml) was added formaldehyde (0.85 ml of 37% w/w solution in water, 11 mmol) and the mixture stirred at ambient temperature for 0.75 h. Sodium triacetoxyborohydride (2.55 g, 12 mmol) was added portionwise over 0.25 h, and the resulting mixture stirred at ambient temperature for 18 h. The reaction was partitioned between dichloromethane (300 ml) and 1M sodium hydroxide (100 ml). The aqueous was re-extracted with dichloromethane (250 ml) and the combined extracts dried (Na$_2$SO$_4$) and the solvent removed in vacuo. The residue was chromatographed on silica gel eluting with ethyl acetate-hexane mixtures to afford the title product (3 g, 96%) as a gum.

Mass spectrum (API$^+$): Found 322. $C_{16}H_{23}N_3O_4$ requires 321.

DESCRIPTION 54

(RS)-2-(Methoxy-methyl-carbamoyl)-4-methyl-piperazine-1-carboxylic acid dimethyl-ethyl ester A mixture of (RS)-2-(Methoxy-methyl-carbamoyl)-4-methyl-piperazine-1-carboxylic acid benzyl ester, D53 (2.9 g, 9 mmol) and di-tert-butyl dicarbonate (2.4 g, 11 mmol) in ethyl acetate (180 ml) was hydrogenated at NTP over 10% Pd—C (1.45 g, 50% aqueous paste) for 64 h. The mixture was filtered through kieselguhr, washed with ethyl acetate and the filtrate evaporated. The residue was chromatographed on silica gel eluting with ethyl acetate-methanol mixtures to afford the title product as a white solid (2.9 g, 92%).

Mass spectrum (API$^+$): Found 288 (MH$^+$). $C_{13}H_{25}N_3O_4$ requires 287.

DESCRIPTION 55

(RS)-2-(1-Benzofuran-2-yl-methanoyl)-4-methyl-piperazine-1-carboxylic acid tert-butyl ester The title compound (1.81 g, 52%) was prepared from (RS)-2-(methoxy-methyl-carbamoyl)-4-methyl-piperazine-1-carboxylic acid dimethyl-ethyl ester, D54 (2.9 g, 10.1 mmol) and benzofuran (0.74 g, 10.1 mol) using the method of Description 2.

Mass spectrum (API$^+$): Found 345 (MH$^+$). $C_{19}H_{24}N_2O_4$ requires 344.

DESCRIPTION 56

(RS)-3-Benzofuran-2-ylmethyl-1-methyl-piperazine

The title compound was obtained from (RS)-2-(1-benzofuran-2-yl-methanoyl)-4-methyl-piperazine-1-carboxylic acid tert-butyl ester, D55 (1.28 g, 3.7 mmol) using the method of Description 3 and was used without purification.

Mass spectrum (API$^+$): Found 231 (MH$^+$). $C_{14}H_{18}N_2O$ require 230.

DESCRIPTION 57

(RS)-1-(5-Fluoro-benzofuran-2-yl)-1-((RS)-4-methyl-piperazin-2-yl)-methanol (RS)-2-[1-(5-Fluoro-benzofuran-2-yl)methanoyl]-4-methyl-piperazine-1-carboxylic acid benzyl ester, D50 (0.65 g, 1.6 mmol) in ethyl acetate (20 ml) and methanol (20 ml) was hydrogenated at NTP over 10% Pd—C (0.47 g, 50% w/w paste in water) for 3.5 h. The reaction mixture was filtered through Kieselguhr, washing well with methanol and the filtrate evaporated to afford the title product (0.41 g, 90%).

$^1$H NMR δ: 2.05 and 2.70 (together 2H, m), 2.12 and 2.62 (together 2H, m), 2.24 (3H, s), 2.94 and 3.12 (2H, m), 3.28 (1H, m), 4.84 (1H, d, J=6 Hz), 6.69 (1H, s), 6.97 (1H, m), 7.19 (1H, dd, J=8 and 2 Hz), 7.36 (1H, dd, J=8 and 4 Hz).

Mass spectrum (API$^+$): Found 265 (MH$^+$). $C_{14}H_{17}N_2O_2$ require 264.

DESCRIPTION 58

(RS)-4-Fluoro-2-piperidin-2-ylmethyl-1H-benzoimidazole (RS)-2-Carboxymethyl-piperidine-1-carboxylic acid tert-butyl ester (1.93 g) was heated with 1,2-diamino-3-fluorobenzene (1.00 g) (Kirk, K. L, J. Org. Chem., 1969, 34, 384) as described in Description 18 to afford the title compound (1.14 g).

Mass Spectrum (API$^+$): Found 234 (MH$^+$). $C_{13}H_{16}FN_3$ requires 333.

DESCRIPTION 59

(RS)-2-(5,6-Difluoro-1H-benzoimidazol-2-ylmethyl)-piperidine-1-carboxylic acid tert-butyl ester A solution of (RS)-5,6-difluoro-2-piperidin-2-ylmethyl-1H-benzoimidazole, D18 (1.5 g) in dichloromethane was treated with triethylamine (0.98 ml), then di-tert-butyl dicarbonate (1.3 g). After stirring for 18 h at room temperature under argon the mixture was diluted with dichloromethane then washed with HCl (2M). The aqueous phase was basified with solid $K_2CO_3$ and extracted with dichloromethane. The organic phase was washed with aqueous $NaHCO_3$, brine and dried ($MgSO_4$). The solvent was removed in vacuo to afford the title compound (2 g).

Mass Spectrum (API$^+$): Found 352 (MH$^+$). $C_{18}H_{23}F_2N_3O_2$ requires 351.

DESCRIPTION 60

(RS)-2-(5,6-Difluoro-1-methyl-1H-benzoimidazol-2-ylmethyl)-piperidine-1-carboxylic acid tert-butyl ester To a stirred suspension of sodium hydride (0.46 g, 60% dispersion in mineral oil) in dimethylformamide (30 ml) at 0° C., under argon, was added (RS)-2-(5,6-difluoro-1H-benzoimidazol-2-ylmethyl)-piperidine-1-carboxylic acid tert-butyl ester, D59 (2 g) and the reaction mixture stirred for a further 30 min. before the addition of iodomethane (0.78 ml). The reaction mixture was then stirred at room temperature for 18 h, a further equivalent of iodomethane (0.35 ml) was added and stirring continued for 24 h. Further portions of sodium hydride (0.23 g, 60% dispersion in mineral oil) and iodomethane (0.35 ml) were added and the reaction stirred for an additional 24 h. After diluting with water, the aqueous layer was extracted with diethyl ether (3×). The combined organics were dried ($MgSO_4$) and solvent removed in vacuo to afford the title compound (0.5 g).

Mass Spectrum (Electrospray LC/MS): Found 266 (MH$^+$—$^t$BOC). $C_{19}H_{25}F_2N_3O_2$ requires 365.

DESCRIPTION 61

(RS)-5,6-Difluoro-1-methyl-2-piperidin-2-ylmethyl-1H-benzoimidazole (RS)-2-(5,6-Difluoro-1-methyl-1H-benzoimidazol-2-ylmethyl)-piperidine-1-carboxylic acid tert-butyl ester, D60 (0.5 g) was treated with trifluoroacetic acid (5 ml) as described for Description 6 to afford the title compound (0.363 g)

Mass spectrum (Electrospray): Found 266 (MH$^+$). $C_{14}H_{17}F_2N_3$ requires 265.

DESCRIPTION 62

(RS)-2-[1-(5-Chloro-benzofuran-2-yl)-methanoyl]-4-methyl-piperazine-1-carboxylic acid tert-butyl ester The title compound (0.98 g) was prepared from (RS)-2-(methoxy-methyl-carbamoyl)-4-methyl-piperazine-1-carboxylic acid dimethyl-ethyl ester, D54 (1.60 g) and 5-chloro-benzofuran (0.86 g, FP1.537.206) using the method of Description 2.

Mass Spectrum (Electrospray LC/MS): Found 279 (MH$^+$—$^t$BOC). $C_{19}H_{23}{}^{35}ClN_2O_4$ requires 378.

DESCRIPTION 63

3-(5-Chloro-benzofuran-2-ylmethyl)-1-methyl-piperazine

The title compound (0.61 g) was prepared from (RS)-2-[1-(5-chloro-benzofuran-2-yl)-methanoyl]-4-methyl-piperazine-1-carboxylic acid tert-butyl ester, D62 (0.98 g) using the method of Description 3 and used without purification.

Mass Spectrum (Electrospray LC/MS): Found 265 (MH$^+$). $C_{14}H_{17}{}^{35}ClN_2O$ requires 264.

DESCRIPTION 64

(RS)-2-[1-(5,7-Dichloro-benzofuran-2-yl)-methanoyl]-4-methyl-piperazine-1-carboxylic acid tert-butyl ester The title compound (0.94 g) was prepared from (RS)-2-(methoxy-methyl-carbamoyl)-4-methyl-piperazine-1-carboxylic acid dimethyl-ethyl ester, D54 (1.00 g) and 5,7-dichloro-benzofuran (0.65 g, FP1.537.206) using the method of Description 2.

Mass Spectrum (Electrospray LC/MS): Found 413 (MH$^+$). $C_{19}H_{22}{}^{35}Cl_2N_2O_4$ requires 412.

DESCRIPTION 65

(RS)-3-(5,7-Dichloro-benzofuran-2-ylmethyl)-1-methyl-piperazine

The title compound (0.53 g) was prepared from (RS)-2-[1-(5,7-dichloro-benzofuran-2-yl)-methanoyl]-4-methyl-piperazine-1-carboxylic acid tert-butyl ester, D64 (0.94 g) using the method of Description 3 and used without purification.

Mass Spectrum (API$^+$LC/MS): Found 299 (MH$^+$). $C_{14}H_{16}{}^{35}Cl_2N_2O$ requires 298.

DESCRIPTION 66

1-(2-Trimethylsilanyl-ethoxymethyl)-1H-indole

A stirring, ice-cooled solution of indole (5.86 g, 50 mmol) in DMF (130 ml) under argon was treated with sodium hydride (3.3 g, 60% dispersion on mineral oil, 80 mmol) and the reaction mixture then stirred at room temperature for 45 min. After cooling to 0° C. 2,2-(trimethylsilyl)ethoxymethyl chloride (12.5 g, 75 mmol) was added dropwise. The reaction mixture was then stirred at room temperature for 4 h. The DMF was removed in vacuo, the residue was poured into water and the product was extracted with diethyl ether. The combined organics were washed with brine, dried ($Na_2SO_4$) and the solvent removed in vacuo. Chromatography (silica gel, 0-20% diethyl ether-40-60 pet.ether) afforded the title compound (12.2 g, 100%).

$^1$HNMR δ: 0.00 (9H, s), 0.96 (2H, t, J=8 Hz), 3.53 (2H, t, J=8 Hz), 5.55 (2H, s), 6.59 (1H, m), 7.20 (2H, m), 7.30 (1H, m with CHCl$_3$), 7.55 (1H, dd, J=1 and 8 Hz), 7.70 (1H, dd, J=1 and 8 Hz).

DESCRIPTION 67

(RS)-2-{1-[1-(2-Trimethylsilanyl-ethoxymethyl)-1H-indol-2-yl]-methanoyl}-piperidine-1-carboxylic acid tert-butyl ester A stirring, ice-cooled solution of 1-(2-trimethylsilanyl-ethoxymethyl)-1H-indole, D66 (742 mg, 3 mmol) in DME (5 ml) was treated drop-wise with n-butyl lithium (2.2 ml, 1.6M in hexanes, 3.5 mmol). The resulting green solution was stirred at 0-5° C. for 15 min. then was treated with (RS)-1-(tert-butyloxycarbonyl)-2-(N-methoxy-N-methylcarbamoyl)-piperidine, D1 (952 mg, 3.5 mmol) in DME (2.5 ml). After stirring at this temperature for a further 45 min. saturated aqueous NH$_4$Cl was added (10 ml) and the product was extracted with diethyl ether. The organics were combined, the solvent removed in vacuo and the residue chromatographed (silica gel, 10% diethyl ether-pentane) to afford the title compound as a colourless oil (510 mg, 37%).

Mass Spectrum (API$^+$): Found 359 (MH$^+$—$^t$BOC). $C_{25}H_{38}N_2O_4Si$ requires 458.

DESCRIPTION 68

(RS)-2-Piperidin-2-ylmethyl-1-(2-trimethylsilanyl-ethoxymethyl)-1H-indole

The title compound (1.1 g) was prepared from (RS)-2-{1-[1-(2-trimethylsilanyl-ethoxymethyl)-1H-indol-2-yl]-methanoyl}-piperidine-1-carboxylic acid tert-butyl ester, D67 (1.9 g) according to a procedure similar to that for Description 3 and used without purification.

DESCRIPTION 69

(RS)-2-[1-(5-Bromo-benzofuran-2-yl)-methanoyl]-piperidine-1-carboxylic acid tert-butyl ester The title compound (0.96 g) was prepared from 5-bromo-benzofuran (3.6 g, prepared according to procedures similar to those described in Synth. Commun., 257, (1989)) and (RS)-1-(tert-butyloxycarbonyl)-2-(N-methoxy-N-methylcarbamoyl)-piperidine, D1 (4.9 g) according to a procedure similar to that for Description 2.

Mass Spectrum (API$^+$): Found 308 (MH$^+$—$^t$BOC). $C_{19}H_{22}{}^{79}BrNO_4$ requires 407.

DESCRIPTION 70

(RS)-2-(5-Bromo-benzofuran-2-ylmethyl)-piperidine

The title compound (0.53 g) was prepared from (RS)-2-[1-(5-bromo-benzofuran-2-yl)-methanoyl]-piperidine-1-carboxylic acid tert-butyl ester, D69 (1.00 g)

according to a procedure similar to that for Description 3 and used without purification.

Mass Spectrum (API$^+$): Found 294 (MH$^+$). $C_{14}H_{16}{}^{79}BrNO$ requires 293.

DESCRIPTION 71

(RS)-2-[1-(4-Bromo-benzofuran-2-yl)-methanoyl]-piperidine-1-carboxylic acid tert-butyl ester The title compound (1.45 g) was prepared from 4-bromo-benzofuran (3.65 g, WO0109111) and (RS)-1-(tert-butyloxycarbonyl)-2-(N-methoxy-N-methylcarbamoyl)-piperidine, D1 (5.17 g) according to a procedure similar to that for Description 2.

Mass Spectrum (API$^+$): Found 308 (MH$^+$—$^t$BOC). $C_{19}H_{22}{}^{79}BrNO_4$ requires 407.

DESCRIPTION 72

(RS)-2-(4-Bromo-benzofuran-2-ylmethyl)-piperidine

The title compound (0.90 g) was prepared from (RS)-2-[1-(4-bromo-benzofuran-2-yl)-methanoyl]-piperidine-1-carboxylic acid tert-butyl ester, D71 (1.40 g) according to a procedure similar to that for Description 3 and used without purification.

DESCRIPTION 73

(RS)-2-[1-(3-Methyl-benzofuran-2-yl)-methanoyl]-piperidine-1-carboxylic acid tert-butyl ester The title compound (300 mg) was prepared from 3-methyl-benzofuran (390 mg) and (RS)-1-(tert-butyloxycarbonyl)-2-(N-methoxy-N-methylcarbamoyl)-piperidine, D1 (820 mg) according to a procedure similar to that for Description 2.

Mass Spectrum (API$^+$): Found 244 (MH$^+$—$^t$BOC). $C_{20}H_{25}NO_4$ requires 343.

DESCRIPTION 74

(RS)-2-(3-Methyl-benzofuran-2-ylmethyl)-piperidine

The title compound (184 mg) was prepared from (RS)-2-[1-(3-methyl-benzofuran-2-yl)-methanoyl]-piperidine-1-carboxylic acid tert-butyl ester, D73 (300 mg) according to a procedure similar to that for Description 3 and used without purification.

DESCRIPTION 75

2-[1-(4-Fluoro-benzofuran-2-yl)-methanoyl]-piperidine-1-carboxylic acid-tert-butyl ester The title compound (500 mg) was prepared from 4-fluoro-benzofuran (450 mg) and (RS)-1-(tert-butyloxycarbonyl)-2-(N-methoxy-N-methylcarbamoyl)-piperidine, D1 (900 mg) according to a procedure similar to that for Description 2.

Mass Spectrum (API$^+$): Found 248 (MH$^+$—$^t$BOC). $C_{19}H_{22}FNO_4$ requires 347.

DESCRIPTION 76

(RS)-2-(4-Fluoro-benzofuran-2-ylmethyl)-piperidine

The title compound (310 mg) was prepared from (RS)-2-[1-(4-fluoro-benzofuran-2-yl)-methanoyl]-piperidine-1-carboxylic acid tert-butyl ester, D75 (500 mg) according to a procedure similar to that for Description 3 and used without purification.

DESCRIPTION 77

(RS)-2-[1-(4,6-Dichloro-benzofuran-2-yl)-methanoyl]-4-methyl-piperazine-1-carboxylic acid tert-butyl ester The title compound (566 mg) was prepared from 4,6-dichloro-benzofuran (390 mg) and (RS)-1-(tert-butyloxycarbonyl)-2-1-methoxy-N-methylcarbamoyl)-piperidine, D1 (600 mg) according to a procedure similar to that for Description 2.

DESCRIPTION 78

(RS)-3-(4,6-Dichloro-benzofuran-2-ylmethyl)-1-methyl-piperazine

The title compound (527 mg) was prepared from (RS)-2-[1-(4,6-dichloro-benzofuran-2-yl)-methanoyl]-4-methyl-piperazine-1-carboxylic acid tert-butyl ester, D77 (900 mg) according to a procedure similar to that for Description 3 and used without purification.

Mass Spectrum (API$^+$): Found 299 (MH$^+$). $C_{14}H_{16}{}^{35}Cl_2N_2O$ requires 298.

DESCRIPTION 79

(RS)-2-(Methoxy-methyl-carbamoyl)-pyrrolidine-1-carboxylic acid tert-butyl ester The title compound was prepared from (RS)-pyrrolidine-1,2-dicarboxylic acid 1-tert-butyl ester (14.8 g) and N,O-dimethylhydroxylamine.HCl (7.37 g) according to a procedure similar to that for Example 4.

Mass Spectrum (Electrospray LC/MS): Found 159 (MH$^+$—$^t$BOC). $C_{12}H_{22}N_2O_4$ requires 258.

DESCRIPTION 80

(RS)-2-(1-Benzofuran-2-yl-methanoyl)-pyrrolidine-1-carboxylic acid tert-butyl ester The title compound (2.7 g) was prepared from benzofuran (2.29 g) and (RS)-2-(methoxy-methyl-carbamoyl)-pyrrolidine-1-carboxylic acid tert-butyl ester, D79 (5.00 g) according to a procedure similar to that for Description 2.

Mass Spectrum (API$^+$): Found 216 (MH$^+$—$^t$BOC). $C_{18}H_{221}NO_4$ requires 315.

DESCRIPTION 81

(RS)-2-Benzofuran-2-ylmethyl-pyrrolidine

The title compound (0.57 g) was prepared from (RS)-2-(1-benzofuran-2-yl-methanoyl)-pyrrolidine-1-carboxylic acid tert-butyl ester, D80 (1.00 g) according to a procedure similar to that for Description 3 and used without purification.

DESCRIPTION 82

(RS)-2-(1-Benzo[b]thiophen-2-yl-methanoyl)-piperidine-1-carboxylic acid tert-butyl ester The title compound (1.60 g) was prepared from benzo[b]thiophene (0.80 g) and (RS)-1-(tert-butyloxycarbonyl)-2-(N-methoxy-N-methylcarbamoyl)-piperidine, D1 (1.62 g) according to a procedure similar to that for Description 2.

DESCRIPTION 83

(RS)-2-Benzo[b]thiophen-2-ylmethyl-piperidine

The title compound (410 mg) was prepared from (RS)-2-(1-benzo[b]thiophen-2-yl-methanoyl)-piperidine-1-carboxylic acid tert-butyl ester, D82 (666 mg)

according to a procedure similar to that for Description 3 and used without purification.

EXAMPLE 1

(RS)-2-(2-Benzofuranylmethyl)-1-((5-(4-fluorophenyl)-2-methyl-thiazol-4-yl)-carbonyl)-piperidine 5-(4-(Fluorophenyl)-2-methyl-thiazole-4-carbonyl chloride (136 mg, 0.53 mmol) in dichloromethane (1 ml) was added to a solution of (RS)-2-(2-benzofuranylmethyl)piperidine (104 mg, 0.48 mmol) and triethylamine (0.20 ml, 1.45 mmol) in dichloromethane (4 ml) and the mixture shaken at ambient temperature for 30 min. The resultant was washed with saturated aqueous sodium hydrogen carbonate (8 ml). The organic layer was applied directly onto a pre-packed silica gel column and chromatographed eluting with ethyl acetate hexane mixtures to give the title compound (50 mg, 24%) as an off-white solid.

Mass spectrum (API$^+$): found 435 (MH$^+$): $C_{25}H_{23}FN_2O_2S$ requires 434.

EXAMPLE 2

(RS)-1-(2-Benzooxazol-2-ylmethyl-piperidin-1-yl)-1-[5-(4-fluoro-phenyl)-2-methyl-thiazol-4-yl]-methanone 5-(4-Fluoro-phenyl)-2-methyl-thiazole-4-carboxylic acid (0.05 g) in dimethylformamide (2.5 ml) was treated sequentially with diisopropylethylamine (0.12 ml), [O-(7-azabenzotriazol-1-yl)-1,1,3,3-tetramethyluronium hexafluorophosphate] (0.08 g) and the amine of Description 6 (0.047 g) in dimethylformamide (2.5 ml). The mixture was stirred for 16 h, diluted with ethyl acetate and the organic phase washed with water, dried (MgSO$_4$) and solvent removed at reduced pressure. The residue was chromatographed (silica gel, 0→30% ethyl acetate:pentane) to give the title compound (0.06 g)

Mass spectrum (API$^+$): found 436 (MH$^+$): $C_{24}H_{22}FN_3O_2S$ requires 435.

EXAMPLE 3

(RS)-1-(2-Benzooxazol-2-ylmethyl-piperidin-1-yl)-1-[2-(3-methyl-[1,2,4]oxadiazol-5-yl)-phenyl]-methanone The title compound (0.02 g) was prepared from the amine of Description 6 (0.047 g) and 2-(3-methyl-[1,2,4]oxadiazol-5-yl)-benzoic acid (0.045 g) according to the method of Example 2.

Mass spectrum (API$^+$): found 403 (MH$^+$): $C_{23}H_{22}N_4O_3$ requires 402.

EXAMPLE 4

(RS)-1-(2-Benzofuran-2-ylmethyl-piperidin-1-yl)-1-[4-(4-fluoro-phenyl)-1-methyl-1-H-pyrazol-3-yl]-methane A mixture of (RS)-2-(2-benzofuranylmethyl)piperidine, D3 (0.108 g, 0.5 mmol), 4-(4-fluoro-phenyl)-1-methyl-1H-pyrazole-3-carboxylic acid (0.11 g, 0.5 mmol), EDC.HCl (0.106 g, 0.55 mmol) and 1-hydroxybenzotriazole (0.01 g, 0.07 mmol) in dichloromethane (4 ml) was shaken for 20 h. The resultant was washed with saturated aqueous sodium bicarbonate (8 ml) and the organic layer was added directly onto a dry 10 g prepacked silica gel cartridge. Elution with 10-100% ethyl acetate in hexane gradient then 1-20% methanol in ethyl acetate gradient afforded the title compound as a colourless amorphous solid (0.059 g, 28%).

$^1$H NMR (CDCl$_3$) δ: 1.05-1.30 (1H, m), 1.35-1.80 (5H, m), 2.80-3.20 (3H, m), 3.53 (0.55H, broad m), 3.81 and 3.93 (3H, 2×s), 4.13 (0.45H, broad m), 4.74 (0.45H, broad m), 5.41 (0.55H, broad m), 6.26 and 6.60 (1H, 2×s), 6.85 and 6.95 (2H, 2×t, J=8.6 Hz), 7.10-7.55 (7H, m).

Mass spectrum (Electrospray LC/MS): Found 418 (MH$^+$). $C_{25}H_{24}FN_3O_2$ requires 417.

The compounds of Examples 5-22 and 90-91 in Table 1 were prepared from the appropriate amine and acid using similar procedures to that described in Example 4. The compound of Example 13 was prepared as the hydrochloride salts.

TABLE 1

| Example | Ar$^2$ | R | Mass Spectrum (Electrospray LC/MS) |
|---|---|---|---|
| 5 | 2-methyl-5-(4-fluorophenyl)thiazol-4-yl | F | Found MH$^+$ 453. $C_{25}H_{22}F_2N_2O_2S$ requires 452 |
| 6 | 2-(pyridin-2-yl)thiazol-4-yl | F | Found MH$^+$ 422. $C_{23}H_{20}FN_3O_2S$ requires 421 |

TABLE 1-continued

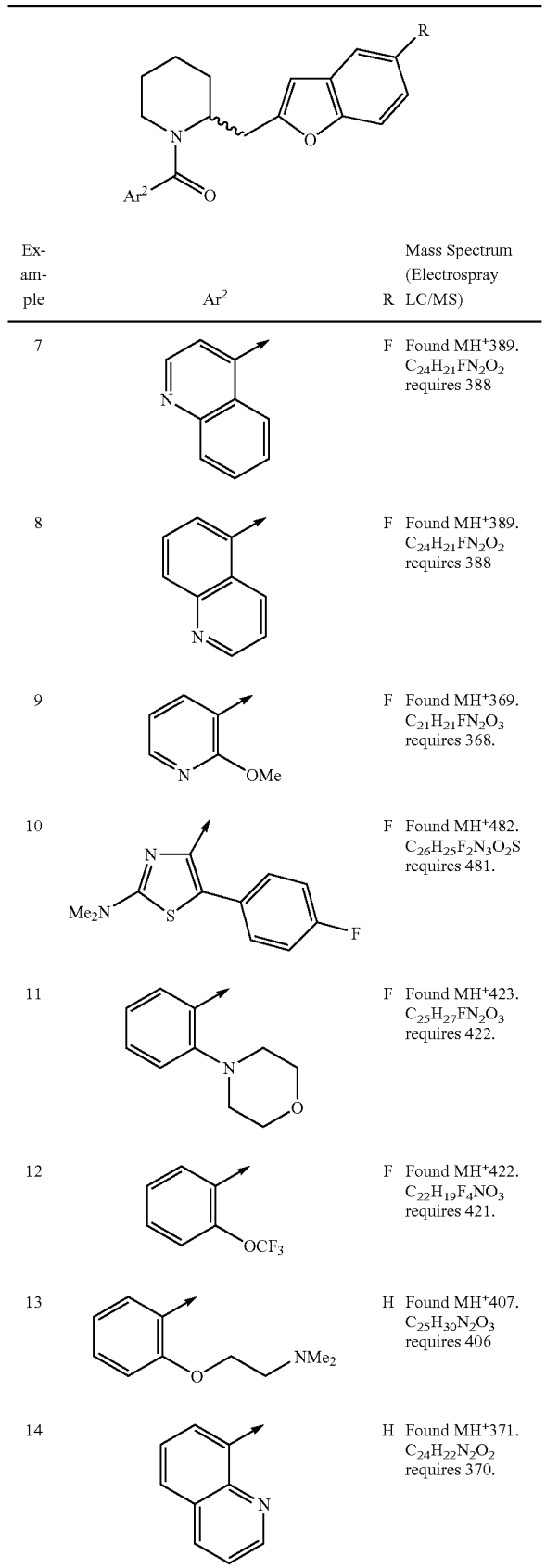

| Example | Ar² | R | Mass Spectrum (Electrospray LC/MS) |
|---|---|---|---|
| 7 | 4-quinolinyl | F | Found MH⁺389. $C_{24}H_{21}FN_2O_2$ requires 388 |
| 8 | 5-quinolinyl | F | Found MH⁺389. $C_{24}H_{21}FN_2O_2$ requires 388 |
| 9 | 2-methoxy-3-pyridyl | F | Found MH⁺369. $C_{21}H_{21}FN_2O_3$ requires 368. |
| 10 | 2-dimethylamino-5-(4-fluorophenyl)thiazol-4-yl | F | Found MH⁺482. $C_{26}H_{25}F_2N_3O_2S$ requires 481. |
| 11 | 2-(morpholin-4-yl)phenyl | F | Found MH⁺423. $C_{25}H_{27}FN_2O_3$ requires 422. |
| 12 | 2-(trifluoromethoxy)phenyl | F | Found MH⁺422. $C_{22}H_{19}F_4NO_3$ requires 421. |
| 13 | 2-(2-dimethylaminoethoxy)phenyl | H | Found MH⁺407. $C_{25}H_{30}N_2O_3$ requires 406 |
| 14 | 8-quinolinyl | H | Found MH⁺371. $C_{24}H_{22}N_2O_2$ requires 370. |

TABLE 1-continued

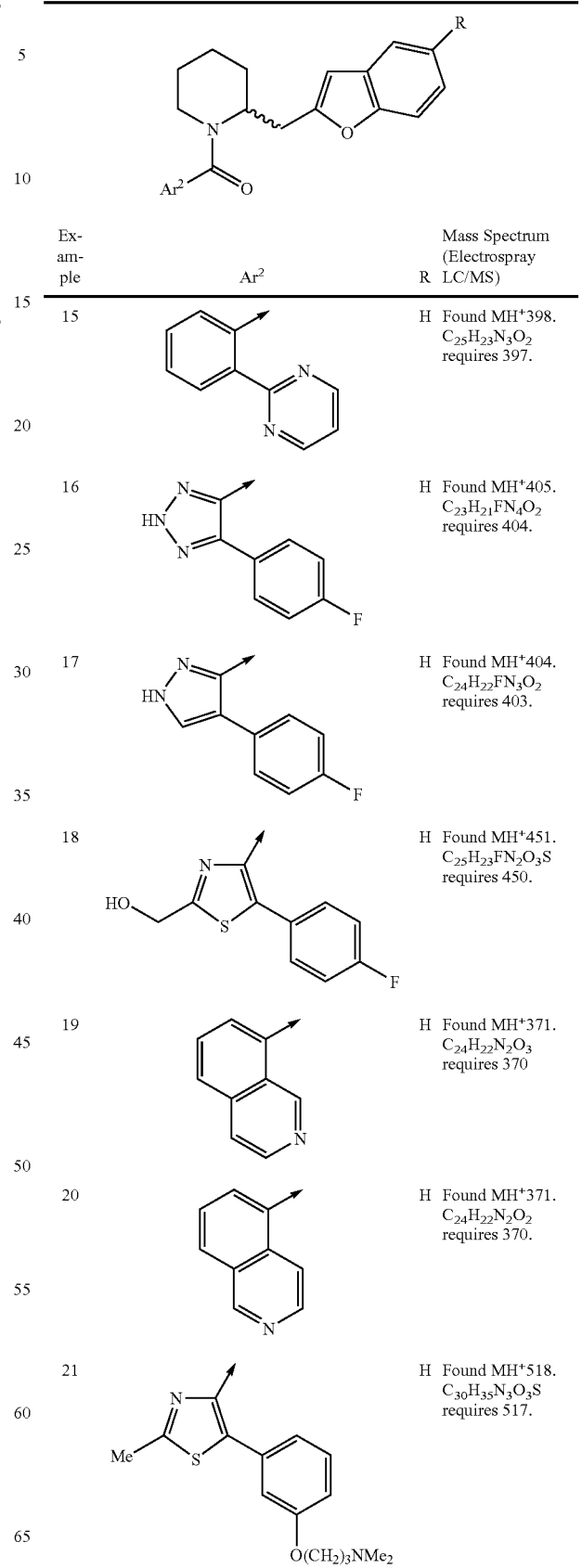

| Example | Ar² | R | Mass Spectrum (Electrospray LC/MS) |
|---|---|---|---|
| 15 | 2-(pyrimidin-2-yl)phenyl | H | Found MH⁺398. $C_{25}H_{23}N_3O_2$ requires 397. |
| 16 | 4-(4-fluorophenyl)-1H-1,2,3-triazol-5-yl | H | Found MH⁺405. $C_{23}H_{21}FN_4O_2$ requires 404. |
| 17 | 4-(4-fluorophenyl)-1H-pyrazol-3-yl | H | Found MH⁺404. $C_{24}H_{22}FN_3O_2$ requires 403. |
| 18 | 2-(hydroxymethyl)-5-(4-fluorophenyl)thiazol-4-yl | H | Found MH⁺451. $C_{25}H_{23}FN_2O_3S$ requires 450. |
| 19 | 8-isoquinolinyl | H | Found MH⁺371. $C_{24}H_{22}N_2O_3$ requires 370 |
| 20 | 5-isoquinolinyl | H | Found MH⁺371. $C_{24}H_{22}N_2O_2$ requires 370. |
| 21 | 2-methyl-5-[3-(3-dimethylaminopropoxy)phenyl]thiazol-4-yl | H | Found MH⁺518. $C_{30}H_{35}N_3O_3S$ requires 517. |

TABLE 1-continued

[Structure: piperidine with N-C(=O)-Ar² substituent and CH₂-linked benzofuran bearing R group]

| Example | Ar² | R | Mass Spectrum (Electrospray LC/MS) |
|---|---|---|---|
| 22 | [2-methyl-thiazol-5-yl substituted with 3-(O(CH₂)₄NMe₂)phenyl] | H | Found MH⁺532. $C_{31}H_{37}N_3O_3S$ requires 531. |
| 90 | [2-methyl-thiazol-5-yl substituted with 4-methoxyphenyl] | H | Found MH⁺447. $C_{26}H_{26}N_2O_3S$ requires 446. (API LC/MS) |
| 91 | [2-methyl-thiazol-5-yl substituted with 3-(OCH₂CH₂NMe₂)phenyl] | H | Found MH⁺504. $C_{29}H_{33}N_3O_3S$ requires 436. |

EXAMPLE 23

(RS)-1-[5-(4-Fluoro-phenyl)-2-methyl-thiazol-4-yl]-1-(2-furo[2,3-b]pyridin-2-ylmethyl-piperidin-1-yl)-methanone The title compound was prepared, using the method of Example 4, from 5-(4-fluoro-phenyl)-2-methyl-thiazole-4-carboxylic acid (0.171 g, 0.72 mmol) and (RS)-2-piperidin-2-ylmethyl-furo[2,3-b]pyridine, D11 (0.13 g, 0.60 mmol) as a colourless solid (0.129 g, 49%).

¹H NMR δ: 0.90-1.20 (1H, m), 1.30-1.85 (5H, m), 2.49 and 2.70 (3H, 2xs), 2.80-3.20 (3H, m), 3.40 (0.45H, m), 4.10 (0.55H, m), 4.70 (0.55, m), 5.35 (0.45H, m), 6.34 and 6.65 (1H, 2xs), 6.92 and 7.00 (2H, 2xt, J=8.6 Hz), 7.15 (1H, m), 7.35-7.50 (2H, m), 7.80 (1H, m), 8.23 (1H, m).

Mass spectrum (Electrospray LC/MS): Found 436 (MH⁺). $C_{24}H_{22}FN_3O_2S$ requires 435.

EXAMPLE 24

(RS)-1-[4-(4-Fluoro-phenyl)-1-methyl-1H-pyrazole-3-yl]-(2-furo[2,3-b]pyridin-2-ylmethyl-piperidin-1-yl)methanone The title compound was prepared using the method of Example 4, from 4-(4-(fluoro-phenyl)-1-methyl-1H-pyrazole-3-carboxylic acid (0.159 g, 0.72 mmol) and (RS)-2-piperidin-2-ylmethyl-furo[2,3-b]pyridine, D11 (0.13 g, 0.60 mmol) as a colourless solid (0.12 g, 48%).

Mass Spectrum (Electrospray LC/MS): Found 419 (MH⁺). $C_{24}H_{23}FN_4O_2$ requires 418.

EXAMPLE 25

(RS)-1-[5-(4-Fluoro-phenyl)-2-methyl-thiazol-4-yl]-1-(2-quinolin-2-ylmethyl-piperidin-1-yl)-methanone The title compound was prepared, using the method of Example 1, from 5-(4-fluoro-phenyl)-2-methyl-thiazole-4-carbonyl chloride (0.09 g, 0.35 mmol) and 2-piperidin-2-ylmethyl-quinoline, D13 (0.053 g, 0.23 mmol) as a colourless solid (0.038 g, 37%).

¹H NMR (DMSO-d₆) δ: 1.00-1.90 (6H, m), 2.37 and 2.66 (3H, 2xs), 2.90-3.30 (3.5H, m), 4.15 (0.5H, m), 4.45 (0.5H, m), 5.25 (0.5H, m), 7.05 (2H, m), 7.10-7.85 (6H, m), 7.90 (1H, m), 8.05-8.30 (1H, 2xd, J=8.4 Hz).

Mass spectrum (Electrospray LC/MS): Found 446 (MH⁺). $C_{26}H_{24}FN_3OS$ requires 445.

EXAMPLE 26

(RS)-1-Benzofuran-2-yl-1-(1-{1-[5-(4-fluoro-phenyl)-2-methyl-thiazol-4-yl]-methanoyl}-piperidin-2-yl)-methanone The title compound was prepared, using the method of Example 1, from 5-(4-fluoro-phenyl)-2-methyl-thiazole-4-carbonyl chloride (0.1 g, 0.39 mmol) and (RS)-1-benzofuran-2-yl-1-piperidin-2-yl-methanone, D9 (0.1 g, 0.43 mmol) as a colourless solid (0.074 g, 43%)

Mass spectrum (Electrospray LC/MS): Found 449 (MH⁺). $C_{25}H_{21}FN_2O_3S$ requires 448.

EXAMPLE 27

(RS)-1-[2-(1H-benzoimidazol-2-ylmethyl)-piperidin-1-yl]-1-[5-(4-fluoro-phenyl)-2-methyl-thiazol-4-yl]-methanone (RS)-(1-{1-[5-(4-Fluoro-phenyl)-2-methyl-thiazol-4-yl]-methanoyl}-piperidin-2-yl)-acetic acid, D17 (110 mg, 0.3 mmol) and benzene-1,2-diamine (33 mg, 0.3 mmol) in PPA (2 g) were heated at 140° C. for 3.5 h. The cooled reaction mixture was poured onto a mixture of crushed ice and K₂CO₃. The basic aqueous solution was extracted with ethyl acetate (3×). The combined organics were washed with brine, dried (MgSO₄) and the solvent removed in vacuo. Chromatography (silica gel, ethyl acetate) afforded the title compound as a dark yellow gum (72 mg, 52%).

Mass Spectrum (Electrospray LC/MS): Found 435 (MH⁺). $C_{24}H_{23}FN_4OS$ requires 434.

The compounds of the Examples 28-34 in Table 2 below were prepared from the appropriate benzene-1,2-diamine and (RS)-(1-{1-[5-(4-fluoro-phenyl)-2-methyl-thiazol-4-yl]-methanoyl}-piperidin-2-yl)-acetic acid, D17 using similar procedures to that described in Example 27.

TABLE 2

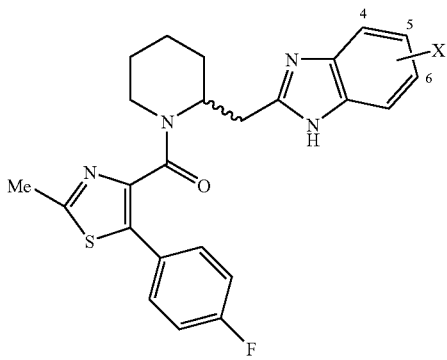

| Example | X | Mass Spectrum (Electrospray LC/MS) |
|---|---|---|
| 28 | 5-Cl | Found MH+469. $C_{24}H_{22}^{35}ClFN_4OS$ requires 468. |
| 29 | 5-F | Found MH+453. $C_{24}H_{22}F_2N_4OS$ requires 452. |
| 30 | 5-Cl, 6-F | Found MH+487. $C_{24}H_{21}^{35}ClF_2N_4OS$ requires 486. |
| 31 | 4-Me | Found MH+449. $C_{25}H_{25}FN_4OS$ requires 448. |
| 32 | 4,6-di-F | Found MH+471. $C_{24}H_{21}F_3N_4OS$ requires 470. |
| 33 | 4-CH$_2$NMe$_2$ | Found MH+492. $C_{27}H_{30}FN_5OS$ requires 491. |
| 34 | 5-Br | Found MH+513. $C_{24}H_{22}^{79}BrFN_4OS$ requires 512. |

EXAMPLE 35

(RS)-1-[2-(5,6-Difluoro-1H-benzoimidazol-2-ylmethyl)-piperidin-1-yl]-1-[5-(4-fluoro-phenyl)-2-methyl-thiazol-4-yl]-methanone A solution of 5-(4-fluoro-phenyl)-2-methyl-thiazole-4-carboxylic acid (700 mg, 3.0 mmol), HATU (1.12 g, 3.0 mmol) and N,N-diisopropylethylamine (1.54 ml, 9.0 mmol) in DMF (20 ml) was stirred at room temperature under argon for 2 min. The mixture was then treated with (RS)-5,6-difluoro-2-piperidin-2-ylmethyl-1H-benzoimidazole, D18 (742 mg, 3.0 mmol) and stirring was continued for 16 h. The solvent was removed in vacuo and the residue partitioned between water and ethyl acetate. The organic phase was dried (Na$_2$SO$_4$) and the solvent removed in vacuo. Chromatography (silica gel, 0-5% methanol-ethyl acetate) afforded the title compound as a pale yellow solid (1.35 g, 97%).

Mass spectrum (Electrospray LC/MS): Found 471 (MH+). $C_{24}H_{21}F_3N_4OS$ requires 470

$^1$H NMR δ: 0.80-1.90 (6H+H$_2$O, bm), 2.71 and 2.75 (3H, 2×s), 3.04 (1H, dt, J=3 and 13 Hz), 3.17 (0.8H, dd, J=5 and 13 Hz), 3.42-3.58 (1.8H, bm), 3.74 (0.2H, m), 4.43 (0.4H, m), 5.35 (1H, 0.8H, m), 6.75 (1.6H, t, J=8 Hz), 7.00-7.20 (3H, bm), 7.40-7.57 (1.4H, m), 11.30 and 12.38 (1H, 2×bs).

The title compound (900 mg) was dissolved in methanol and treated with 1M HCl in diethyl ether (excess). The volatiles were removed in vacuo and the residue was triturated with ethyl acetate to give a white solid (805 mg). A sample (450 mg) was crystallised form ethyl acetate to give the hydrochloride salt of the title compound as white solid (420 mg).

Mass spectrum (Electrospray LC/MS) Found 471. $C_{24}H_{21}F_3N_4OS$ requires 470.

EXAMPLE 36

(RS)-1-[2-(4,5-Difluoro-1H-benzoimidazol-2-ylmethyl)-piperidin-1-yl]-1-[5-(4-fluoro-phenyl)-2-methyl-thiazol-4-yl]-methanone A solution of 5-(4-fluoro-phenyl)-2-methyl-thiazole-4-carboxylic acid (1.00 g, 4.2 mmol), HATU (1.60 g, 4.2 mmol) and N,N-diisopropylethylamine (2.00 ml, 11.6 mmol) in DMF (20 ml) was stirred at room temperature under argon for 2 min. The mixture was then treated with (RS)-4,5-difluoro-2-piperidin-2-ylmethyl-1H-benzoimidazole, D21 (1.06 g, 4.2 mmol) and stirring was continued for 16 h. The solvent was removed in vacuo and the residue was washed with water then was triturated with ethyl acetate to afford the title compound as an off-white solid (1.68 g, 85%).

Mass spectrum (Electrospray LC/MS): Found 471 (MH+). $C_{24}H_{21}F_3N_4OS$ requires 470.

The title compound (650 mg) was dissolved in methanol and treated with 1M HCl in diethyl ether (excess). The volatiles were removed in vacuo and the residue was triturated with ethyl acetate to afford the hydrochloride salt of the title compound as a white solid (615 mg). Mass spectrum (Electrospray LC/MS) Found 471 (MH+). $C_{24}H_{21}F_3N_4OS$ requires 470.

EXAMPLE 37

(RS)-1-[2-(5,6-Difluoro-1H-benzoimidazol-2-ylmethyl)-piperidin-1-yl]-1-[5-(4-fluoro-phenyl)-2-hydroxymethyl-thiazol-4-yl]-methanone A stirring solution of 5-(4-fluoro-phenyl)-2-hydroxymethyl-thiazole-4-carboxylic acid (632 mg, 2.0 mmol, 80% pure), EDC.HCl (311 mg, 2.0 mmol) and 1-hydroxybenzotriazole (270 mg, 2.0 mmol) in DMF (20 ml) was treated with (RS)-5,6-difluoro-2-piperidin-2-ylmethyl-1H-benzoimidazole, D18 (500 mg, 2.0 mmol). The reaction mixture was stirred at room temperature, under argon for 16 h. The DMF was removed in vacuo and the residue was partitioned between ethyl acetate and water. The organic phase was dried (Na$_2$SO$_4$) and the solvent removed in vacuo. Chromatography (silica gel, 0-10% methanol-ethyl acetate) afforded the title compound as a pale yellow solid (350 mg, 36%).

Mass spectrum (Electrospray LC/MS): Found 487 (MH+). $C_{24}H_{21}F_3N_4O_2S$ requires 486.

$^1$H NMR (DMSO-d$_6$) δ: 0.90-1.80 (6H, bm), 2.92-3.30 (3H+DMSO, bm), 4.15 (0.4H, m), 4.40-4.60 (1H, bm), 4.73 (1H, d, J=9 Hz), 5.30 (0.6H, m), 6.20 (1H, m), 7.05-7.65 (6H, bm), 12.24 and 12.56 (1H, 2×bs).

The title compound (350 mg) was dissolved in methanol and treated with 1M HCl in diethyl ether (excess). The volatiles were removed in vacuo and the residue was triturated with EtOAc to afford the hydrochloride salt of the title compound as a white solid (215 mg). Mass spectrum (Electrospray LC/MS) Found 487 (MH+). $C_{24}H_{21}F_3N_4O_2S$ requires 486.

EXAMPLE 38

(RS)-1-[2-(4,5-Difluoro-1H-benzoimidazol-2-ylmethyl)-piperidin-1-yl]-1-[5-(4-fluoro-phenyl)-2-hydroxymethyl-thiazol-4-yl]-methanone A stirring solution of 5-(4-fluoro-phenyl)-2-hydroxymethyl-thiazole-4-carboxylic acid (320 mg, 1.0 mmol, 80% pure) and (RS)-4,5-difluoro-2-piperidin-2-ylmethyl-1H- benzoimidazole, D21 (250 mg, 1.0 mmol) in DMF (10 ml) was treated with EDC.HCl (194 mg, 1.0 mmol) and 1-hydroxybenzotriazole (50 mg, 0.4 mmol). The reaction mixture was stirred at room temperature, under argon for 16 h. The resulting solution was diluted with diethyl ether then washed with saturated aqueous NaHCO$_3$, water (3×) and brine. Drying (MgSO$_4$) and removal of the solvent in vacuo afforded an orange gum. Chromatography (silica gel, 0-2% methanol-dichloromethane) afforded the title compound as an orange powder (160 mg, 33%). Mass spectrum (Electrospray LC/MS) Found 487 (MH$^+$). C$_{24}$H$_{21}$F$_3$N$_4$O$_2$S requires 486.

The title compound (80 mg) was dissolved in methanol and treated with 1M HCl in diethyl ether (excess). The volatiles were removed in vacuo and the residue was triturated with diethyl ether to afford the hydrochloride salt of the title compound as a pale orange solid (65 mg).

Mass spectrum (Electrospray LC/MS): Found 487 (MH$^+$). C$_{24}$H$_{21}$F$_3$N$_4$O$_2$S requires 486.

EXAMPLE 39

(RS)-1-[2-(5,6-Difluoro-1H-benzoimidazol-2-ylmethyl)-piperidin-1-yl]-1-[4-(4-fluoro-phenyl)-1-methyl-1H-pyrazol-3-yl]-methanone A solution of 4-(4-fluoro-phenyl)-1-methyl-1H-pyrazole-3-carboxylic acid (73 mg, 0.33 mmol), HATU (124 mg, 0.33 mmol) and N,N-diisopropylethylamine (0.35 ml) in DMF (6 ml) was stirred at room temperature under argon for 0.5 h. The mixture was then treated with (RS)-5,6-difluoro-2-piperidin-2-ylmethyl-1H-benzoimidazole.2HCl, D$_{20}$ (105 mg, 0.33 mmol) and stirring, under argon was continued for 16 h. The reaction mixture was diluted with diethyl ether and washed with water (3×), dried (MgSO$_4$) and the solvent removed in vacuo. Chromatography (silica gel, ethyl acetate) afforded the title compound (88 mg, 57%).

Mass spectrum (Electrospray LC/MS): Found 454 (MH$^+$). C$_{24}$H$_{22}$F$_3$N$_5$O requires 453.

EXAMPLE 40

(RS)-1-[2-(5-Methoxy-1H-benzoimidazol-2-ylmethyl)-piperidin-1-yl]-1-[5-(4-fluoro-phenyl)-2-methyl-thiazol-4-yl]-methanone A stirring mixture of (1-{1-[5-(4-Fluoro-phenyl)-2-methyl-thiazol-4-yl]-methanoyl}-piperidin-2-yl)-acetic acid, D17 (150 mg, 0.42 mmol) and 4-methoxy-benzene-1,2-diamine (58 mg, 0.42 mmol) was heated at 120° C. for 4 h. The cooled reaction mixture was dissolved in ethyl acetate, washed with sodium hydrogen carbonate (2×) then brine. The solvent was removed in vacuo and the residue was chromatographed (silica gel, ethyl acetate) to afford the title compound as a brown gum (25 mg, 13%).

Mass spectrum (Electrospray LC/MS): Found 465 (MH$^+$). C$_{25}$H$_{25}$FN$_4$O$_2$S requires 464.

The compounds of the Examples 41-50 and 92-108 were prepared from the appropriate carboxylic acid or acid chloride and (RS)-4,5-difluoro-2-piperidin-2-ylmethyl-1H-benzoimidazole, D21 using a similar procedure to that described in Example 2 or a procedure similar to that described in Examples 1 or 4. The compounds of Examples 47, 48 and 49 were converted to hydrochloride salts by treatment with 1M HCl in diethyl ether. The compound of Example 96 was prepared as the trifluoroacetate salt.

TABLE 3

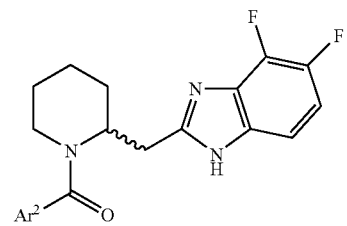

| Example | Ar$^2$ | Method | Mass Spectrum (Electrospray LC/MS) |
|---|---|---|---|
| 41 | 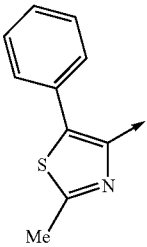 | E2 | Found MH$^+$453. C$_{24}$H$_{22}$F$_2$N$_4$OS requires 452. |
| 42 | 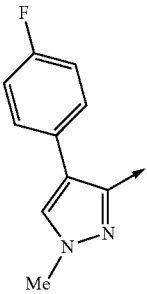 | E2 | Found MH$^+$454. C$_{24}$H$_{22}$F$_3$N$_5$O requires 453. |
| 43 | 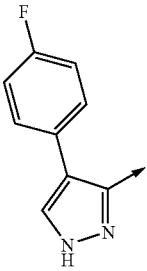 | E2 | Found MH$^+$440. C$_{23}$H$_{20}$F$_3$N$_5$O requires 439. |
| 44 | 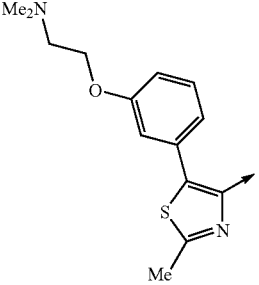 | E2 | Found MH$^+$540. C$_{28}$H$_{31}$F$_2$N$_5$O$_2$S requires 539. |

TABLE 3-continued

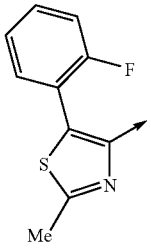

| Example | Ar² | Method | Mass Spectrum (Electrospray LC/MS) |
|---|---|---|---|
| 45 | 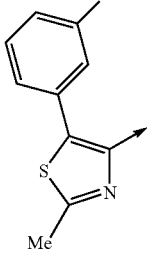 | E4 | Found MH⁺471. $C_{24}H_{21}F_3N_4OS$ requires 470. |
| 46 | 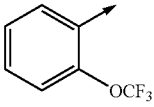 | E4 | Found MH⁺471. $C_{24}H_{21}F_3N_4OS$ requires 470. |
| 47 | 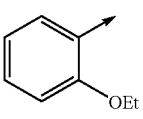 | E2 | Found MH⁺440. $C_{21}H_{18}F_5N_3O_2$ requires 439. |
| 48 | 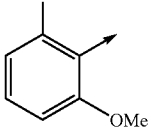 | E2 | Found MH⁺400. $C_{22}H_{23}F_2N_3O_2$ requires 399. |
| 49 | 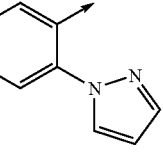 | E2 | Found MH⁺416. $C_{22}H_{23}F_2N_3O$ requires 415. |
| 50 | 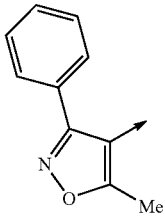 | E2 | Found MH⁺422. $C_{23}H_{21}F_2N_5O$ requires 421. |
| 92 | 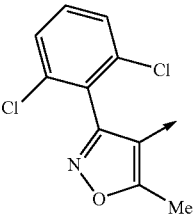 | E2 | Found MH⁺437. $C_{24}H_{22}F_2N_4O_2$ requires 436. |
| 93 | 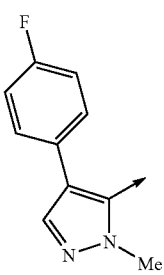 | E2 | Found MH⁺505. $C_{24}H_{20}{}^{35}Cl_2F_2N_4O_2$ requires 504. |
| 94 | 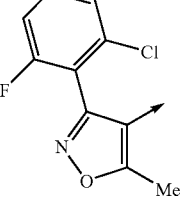 | E2 | Found MH⁺454. $C_{24}H_{22}F_3N_5O$ requires 453. |
| 95 | 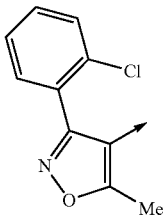 | E1 | Found MH⁺489. $C_{24}H_{20}{}^{35}ClF_3N_4O_2$ requires 488. |
| 96 |  | E2 | Found MH⁺471. $C_{24}H_{21}{}^{35}ClF_2N_4O_2$ requires 470. |

TABLE 3-continued

| Example | Ar² | Method | Mass Spectrum (Electrospray LC/MS) |
|---|---|---|---|
| 97 | 2-propoxyphenyl | E2 | Found MH⁺414. $C_{23}H_{25}F_2N_3O_2$ requires 413. |
| 98 | 2-isopropoxyphenyl | E2 | Found MH⁺414. $C_{23}H_{25}F_2N_3O_2$ requires 413. |
| 99 | 2-benzyloxyphenyl | E2 | Found MH⁺462. $C_{27}H_{25}F_2N_3O_2$ requires 461. |
| 100 | 2,6-(OEt)(OMe)phenyl | E2 | Found MH⁺430. $C_{23}H_{25}F_2N_3O_3$ requires 429. |
| 101 | 2-OEt-6-Me-phenyl | E2 | Found MH⁺414. $C_{23}H_{25}F_2N_3O_2$ requires 413. |
| 102 | 2,6-(OEt)₂phenyl | E2 | Found MH⁺444. $C_{24}H_{27}F_2N_3O_3$ requires 443. |
| 103 | 3-acetyl-4-ethoxyphenyl | E2 | Found MH⁺442. $C_{24}H_{25}F_2N_3O_3$ requires 441. |
| 104 | 2-ethoxynaphth-1-yl | E2 | Found MH⁺450. $C_{26}H_{25}F_2N_3O_2$ requires 449. |
| 105 | 2-(pyridin-2-yl)phenyl | E2 | Found MH⁺433. $C_{25}H_{22}F_2N_4O$ requires 432. |
| 106 | 2-(pyrrol-1-yl)phenyl | E2 | Found MH⁺421. $C_{24}H_{22}F_2N_4O$ requires 420. |
| 107 | 3-[3-(dimethylamino)propoxy]-5-(2-methylthiazol-4-yl)phenyl | E2 | Found MH⁺554. $C_{29}H_{33}F_2N_5O_2S$ requires 553. |
| 108 | 3-[4-(dimethylamino)butoxy]-5-(2-methylthiazol-4-yl)phenyl | E2 | Found MH⁺568. $C_{30}H_{35}F_2N_5O_2S$ requires 567. |

The compounds of the Examples 51-55 and 109-112 in Table 4 were prepared from the appropriate carboxylic acid and (RS)-5,6-difluoro-2-piperidin-2-ylmethyl-1H-benzoimidazole, D18 using a similar procedure to that described in Example 2 or Example 4 or from the appropriate acid chloride and (RS)-5,6-difluoro-2-piperidin-2-ylmethyl-1H-benzoimidazole, D18 using a procedure similar to that described for Example 1. The compound of Example 55 was converted to the hydrochloride salt by treatment with 1M HCl in diethyl ether. The compound of Example 109 was prepared as the trifluoroacetate salt.

TABLE 4

| Example | Ar² | Method | Mass Spectrum (Electrospray LC/MS) |
|---|---|---|---|
| 51 | 4-F-phenyl-pyrazole | E2 | Found MH⁺440. $C_{23}H_{20}F_3N_5O$ requires 439. |
| 52 | 2-substituted phenyl-(3-Me-1,2,4-oxadiazol-5-yl) | E2 | Found MH⁺438. $C_{23}H_{21}F_2N_5O_2$ requires 437 |
| 53 | 4-F-phenyl-1-(2-dimethylaminoethyl)pyrazole | E2 | Found MH⁺511. $C_{27}H_{29}F_3N_6O$ requires 510 |
| 54 | 4-F-phenyl-2-Me-triazole | E2 | Found MH⁺455. $C_{23}H_{21}F_3N_6O$ requires 454 |
| 55 | 3-[O(CH₂)₃NMe₂]-phenyl-thiophene | E1 | Found MH⁺539. $C_{29}H_{32}F_2N_4O_2S$ requires 538. |
| 109 | 4-F-phenyl-(2-MeO-thiazole) | E4 | Found MH⁺487. $C_{24}H_{21}F_3N_4O_2S$ requires 486. |
| 110 | 4-F-phenyl-(2-Et-thiazole) | E2 | Found MH⁺485. $C_{25}H_{23}F_3N_4OS$ requires 484. |
| 111 | 2-F-phenyl-(2-Me-thiazole) | E4 | Found MH⁺471. $C_{24}H_{21}F_3N_4OS$ requires 470. |

TABLE 4-continued

| Example | Ar² | Method | Mass Spectrum (Electrospray LC/MS) |
|---------|-----|--------|------------------------------------|
| 112 | F—[3-fluorophenyl-thiazol-Me] | E4 | Found MH⁺471. C$_{24}$H$_{21}$F$_3$N$_4$OS requires 470. |

EXAMPLE 56

(RS)-1-[2-(5,6-Difluoro-1-methyl-1H-benzoimidazol-2-ylmethyl)-piperidin-1-yl]-1-[5-(4-fluoro-phenyl)-2-methyl-thiazol-4-yl]-methanone (RS)-1-[2-(5,6-Difluoro-1H-benzoimidazol-2-ylmethyl)-piperidin-1-yl]-1-[5-(4-fluoro-phenyl)-2-methyl-thiazol-4-yl]-methanone, E35 (400 mg, 0.85 mmol) was slowly added to an ice-cooled slurry of NaH (68 mg, 60% dispersion on mineral oil, 1.7 mmol) in DMF (10 ml). After 0.5 h iodomethane (0.90 mmol) was added. The reaction mixture was stirred at room temperature, under argon for 16 h. 2N HCl (9 drops) then water (100 ml) were added. The aqueous phase was extracted with EtOAc (2×) and the combined organics washed with brine, dried (Na$_2$SO$_4$) and the solvent removed in vacuo. The residue was chromatographed (silica gel, 50-100% pentane-ethyl acetate). Residual DMF was removed by dissolving in ethyl acetate/diethyl ether and washing with water (2×). Drying (Na$_2$SO$_4$) and removal of the solvent in vacuo afforded the title compound as a pale yellow solid (142 mg, 34%).

Mass spectrum (Electrospray LC/MS): Found 485 (MH⁺). C$_{25}$H$_{23}$F$_3$N$_4$OS requires 484.

EXAMPLE 57

1-[(S)-2-(1H-Benzoimidazol-2-ylmethyl)-pyrrolidin-1-yl]-1-[5-(4-fluoro-phenyl)-2-methyl-thiazol-4-yl]-methanone The title compound was prepared from (S)-pyrrolidin-2-ylmethyl-1H-benzoimidazole, D26 and 5-(4-fluoro-phenyl)-2-methyl-thiazol-4-carboxylic acid by a procedure similar to that described for Example 2. Chromatography (silica gel, 0-8%[10% 0.880 NH$_3$ in MeOH] in dichloromethane) afforded the title compound as a brown gum.

Mass spectrum (API⁺): found 421 (MH⁺). C$_{23}$H$_{21}$N$_4$OS requires 420.

EXAMPLE 58

1-[(S)-2-(5,6-Difluoro-1H-benzoimidazol-2-ylmethyl)-pyrrolidin-1-yl]-1-[5-(4-fluoro-phenyl)-2-methyl-thiazol-4-yl]-methanone The title compound was prepared from, (S)-5,6-difluoro-pyrrolidin-2-ylmethyl-1H-benzoimidazole, D27 and 5-(4-fluoro-phenyl)-2-methyl-thiazole-4-carboxylic acid by a procedure similar to that described for Example 1. Chromatography (silica gel, 0-8%[10% 0.880 NH$_3$ in methanol] in dichloromethane) afforded the title compound as a beige solid.

Mass spectrum (API⁺): found 457 (MH⁺). C$_{23}$H$_{19}$F$_3$N$_4$OS requires 456.

EXAMPLE 59

1-[(S)-2-(5,6-Difluoro-1H-benzoimidazol-2-ylmethyl)-pyrrolidin-1-yl]-1-[4-(4-fluoro-phenyl)-1-methyl-1H-pyrazol-3-yl]methanone The title compound was prepared from, (S)-5,6-difluoro-pyrrolidin-2-ylmethyl-1H-benzoimidazole, D27 and 4-(4-fluoro-phenyl)-1-methyl-1H-pyrazole-3-carboxylic acid by a procedure similar to that described for Example 2. Chromatography (silica gel, 0→8%[10% 0.880 NH$_3$ in methanol] in dichloromethane) afforded the title compound as a beige solid.

Mass spectrum (API⁺): found 440 (MH⁺): C$_{23}$H$_{20}$F$_3$N$_5$O requires 439.

EXAMPLE 60

(RS)-1-(2-Benzothiazol-2-ylmethylpiperidin-1-yl)-1-[5-(4-fluorophenyl)-2-methylthiazol-4-yl]-methanone 2-Piperidin-2-ylmethylbenzothiazole, D30 (0.135 g), HATU (0.228 g), diisopropylethylamine (0.300 ml) and 5-(4-fluorophenyl)-2-methylthiazol-4-carboxylic acid (0.144 g) were dissolved in dry DMF and shaken at room temperature for 16 hours. The solvent was then evaporated and the residue partitioned between dichloromethane and brine. The organic layer was dried (MgSO$_4$), evaporated and the residue chromatographed over silica gel. Elution with diethyl ether provided the title compound as a foam (220 mg).

Mass spectrum (API⁺): found 452 (MH⁺): C$_{24}$H$_{22}$FN$_3$OS$_2$ requires 451.

EXAMPLE 61

(RS)-1-(2-Benzothiazol-2-ylmethylpiperidin-1-yl)-1-[4-(4-fluorophenyl)-1-methyl-1-H-pyrazol-3-yl]-methanone The title compound (0.210 g) was prepared from 2-piperidin-2-ylmethyl-benzothiazole, D30 (0.135 g) and 4-(4-fluorophenyl)-1-methyl-1-H-pyrazol-3-carboxylic acid (0.135 g) using the procedure described in Example 60.

Mass spectrum (API⁺): found 435 (MH⁺): C$_{24}$H$_{23}$FN$_4$OS requires 434.

EXAMPLE 62

(RS)-1-(2-Benzothiazol-2-ylmethylpiperidin-1-yl)-1-[2-(3-methyl-[1,2,4]oxadiazol-5-yl)phenyl]-methanone The title compound (0.170 g) was prepared from 2-piperidin-2-ylmethyl-benzothiazole, D30 (0.135 g), and 2-(3-methyl-[1,2,4]oxadiazol-5-yl)benzoic acid (0.126 g) using the procedure described in Example 60.

Mass spectrum (API$^+$): found 419 (MH$^+$): $C_{23}H_{22}N_4O_2S$ requires 418.

EXAMPLE 63 AND EXAMPLE 64

(RS)-1-[5-(4-Fluorophenyl)-2-methylthiazol-4-yl]-1-[2-(5,6,7,8-tetrahydro-[1,2,4]-triazolo[1,5-a]pyridin-2-ylmethyl)-piperidin-1-yl]-methanone and (RS)-1-[5-(4-Fluorophenyl)-2-methylthiazol-4-yl]-1-(2-[1,2,4]triazolo[1,5-a]pyridin-2-ylmethylpiperidin-1-yl)-methanone The mixture of 2-piperidin-2-ylmethyl-5,6,7,8-tetrahydro-[1,2,4]-triazolo[1,5-a]pyridine and 2-piperidin-2-ylmethyl-[1,2,4]-triazolo[1,5-a]pyridine, D34 (0.220 g) was treated with HATU (0.380 g), N,N-diisopropylethylamine (1.0 ml) and 5-(4-fluorophenyl)-2-methylthiazole-4-carboxylic acid (0.240 g) in dry DMF, according to the procedure described in Example 60. The crude product was chromatographed (silica gel, 4% methanol-diethyl ether) to afford 1-[5-(4-fluoro-phenyl)-2-methylthiazol-4-yl]-1-(2-[1,2,4]-triazolo[1,5-a]pyridin-2-ylmethylpiperidin-1-yl)-methanone as a colourless foam (0.070 g) (Mass spectrum (API$^+$): found 436 (MH$^+$): $C_{23}H_{22}FN_5OS$ requires 435). Continued elution (10% methanol-diethyl ether) afforded 1-[5-(4-fluoro-phenyl)-2-methyl-thiazol-4-yl]-1-[2-(5,6,7,8-tetrahydro-[1,2,4]-triazolo[1,5-a]pyridin-2-ylmethyl)-piperidin-1-yl]-methanone as a colourless foam (0.230 g) (Mass spectrum (API$^+$): found 440 (MH$^+$): $C_{23}H_{26}FN_5OS$ requires 439).

EXAMPLE 65a AND b

1-[(RS)-2-((RS)-2-Benzofuran-2-yl-2-hydroxy-ethyl)-piperidin-1-yl]-1-[5-(4-fluoro-phenyl)-2-methyl-thiazol-4-yl]-methanone (as separate diastereoisomers)

A solution of (RS)-1-Benzofuran-2-yl-2-(1-{1-[5-(4-fluoro-phenyl)-2-methyl-thiazol-4-yl]-methanoyl}-piperidin-2-yl)-ethanone, D38 (50 mg, 0.11 mmol) in methanol was treated with sodium borohydride (50 mg). The reaction mixture was stirred at room temperature, under argon for 16 h. The volatiles were removed in vacuo and the residue was triturated with dichloromethane. The dichloromethane soluble material was chromatographed (silica gel, diethyl ether) to afford, separately the two diastereoisomers of the title compound.

Mass spectrum (API$^+$): found 447 (MH$^+$—H$_2$O): $C_{26}H_{25}FN_2O_3S$ requires 464 (first eluting diastereoisomer).

Mass spectrum (API$^+$): found 447 (MH$^+$—H$_2$O): $C_{26}H_{25}FN_2O_3S$ requires 464 (second eluting diastereoisomer)

EXAMPLE 66

(RS)-1-[2-(4-Bromo-1H-benzoimidazol-2-ylmethyl)-piperidin-1-yl]-1-[5-(4-fluorophenyl)-2-methylthiazol-4-yl]methanone 2-Methyl-5-(4-fluorophenyl)thiazole-4-carbonyl chloride (383 mg, 1.5 mmol) was added portionwise over 5 min. to a stirred solution of (RS)-4-bromo-2-piperidin-2-ylmethyl-1H-benzoimidazole, D39 (400 mg, 1.4 mmol) and triethylamine (0.57 ml, 5.0 mmol) in dichloromethane (20 ml) at room temperature. After 20 h the mixture was washed with saturated sodium hydrogen carbonate. The organic layer was dried (Na$_2$SO$_4$) and the solvent removed in vacuo. Chromatography (silica gel, 10-100% ethyl acetate-hexane then 1-10% methanol-ethyl acetate) afforded the title compound as a pale brown amorphous solid (620 mg, 89%).

Mass spectrum (Electrospray LC/MS): Found 513 (MH$^+$). $C_{24}H_{22}{}^{79}BrFN_4OS$ requires 512.

EXAMPLE 67

(RS)-1-[2-(4-Cyano-1H-benzoimidazol-2-ylmethyl)-piperidin-1-yl]-1-[5-(4-fluorophenyl)-2-methylthiazol-4-yl]methanone A mixture of (RS)-1-[2-(4-bromo-1H-benzoimidazol-2-ylmethyl)-piperidin-1-yl]-1-[5-(4-fluorophenyl)-2-methylthiazol-4-yl]methanone, E66 (216 mg, 0.42 mmol) and copper(I)cyanide (76 mg, 0.84 mmol) in N-methylpyrrolidinone (15 ml) was heated at reflux for 3 h. The reaction mixture was cooled, poured into water and extracted with ethyl acetate (2×). Solid sodium chloride was added to the aqueous layer which was further extracted with ethyl acetate (2×). The combined organic extracts were washed with brine, dried (Na$_2$SO$_4$) and the solvent removed in vacuo. The residue was Chromatographed (silica gel, 10-100% ethyl acetate-hexane then 1-20% methanol-ethyl acetate). Further purification by HPLC (Supercosil ABZ$^+$, 5-95% acetonitrile containing 0.1% trifluoroacetic acid-water containing 0.1% trifluoroacetic acid) afforded the title compound as a pale brown amorphous solid (5.3 mg, 3%).

Mass spectrum (Electrospray LC/MS): Found 460 (MH$^+$). $C_{25}H_{22}FN_5OS$ requires 459.

EXAMPLE 68

(RS)-1-[2-(4-Acetyl-1H-benzoimidazol-2-ylmethyl)-piperidin-1-yl]-1-[5-(4-fluorophenyl)-2-methylthiazol-4-yl]methanone To a deoxygenated solution of (RS)-1-[2-(4-bromo-1H-benzoimidazol-2-ylmethyl)-piperidin-1-yl]-1-[5-(4-fluorophenyl)-2-methylthiazol-4-yl]methanone, E66 (200 mg, 0.39 mmol) in anhydrous 1,4-dioxane (10 ml) was added tributyl(1-ethoxyvinyl)tin (155 mg, 0.43 mmol) and tetrakis(triphenylphosphine)palladium(0) (30 mg, 0.026 mmol). The resultant mixture was refluxed under argon for 20 h. Further tetrakis(triphenylphosphine)palladium(0) (60 mg, 0.052 mmol) was added and refluxing continued for a further 24 h. On cooling, water (15 ml) and 5N hydrochloric acid (10 drops) were added and the mixture stirred at room temperature for 2 h. The reaction mixture was poured into water and extracted with ethyl acetate (3×). The combined organics were dried (Na$_2$SO$_4$) and the solvent removed in vacuo. Chromatography (silica gel, 0-100% ethyl acetate-hexane then 2-5% methanol-ethyl acetate) afforded the title compound as a pale orange solid (62 mg, 33%).

Mass spectrum (Electrospray LC/MS): Found 475 (M-H). $C_{26}H_{25}FN_4O_2S$ requires 476.

EXAMPLE 69

(RS)-2-(1-{1-[5-(4-Fluoro-phenyl)-2-methyl-thiazol-4-yl]-methanoyl}-piperidin-2-ylmethyl)-1H-benzoimidazole-5-carbonitrile A stirring mixture of (RS)-1-[2-(5-bromo-1H-benzoimidazol-2-ylmethyl)-piperidin-1-yl]-1-[5-(4-fluoro-phenyl)-2-methyl-thiazol-4-yl]-methanone, E34 (25 mg, 0.44 mmol) and copper(I)cyanide (79 mg, 0.88 mmol) in N-methylpyrrolidinone (7 ml) under argon was heated at 200° C. for 5 h. The cooled reaction mixture was diluted with water/ethyl acetate and filtered through Kieselghur. The organic phase was washed with water (2×), brine (2×), dried (MgSO$_4$) and the solvent removed in vacuo. The residue was chromatograped (silica gel, 0-4% methanol (containing 10%. 0.880 ammonia)-dichloromethane). Further purification by HPLC (Supercosil ABZ$^+$, 5-95% acetonitrile containing 0.1% trifluoroacetic acid-water containing 0.1% trifluoroacetic acid) afforded the title compound as a pale brown gum (2 mg, 1%).

Mass spectrum (Electrospray LC/MS): Found 460 (MH$^+$). $C_{25}H_{22}FN_5OS$ requires 459.

EXAMPLE 70

(RS)-1-[2-(5,6-Difluoro-1-propyl-1H-benzoimidazol-2-ylmethyl)-piperidin-1-yl]-1-[5-(4-fluoro-phenyl)-2-methyl-thiazol-4-yl]-methanone (RS)-1-[2-(5,6-Difluoro-1H-benzoimidazol-2-ylmethyl)-piperidin-1-yl]-1-[5-(4-fluoro-phenyl)-2-methyl-thiazol-4-yl]-methanone, E35 (150 mg, 0.32 mmol) was added slowly to an ice-cooled slurry of sodium hydride (26 mg, 0.64 mmol, 60% dispersion in mineral oil) in DMF (10 ml). After stirring for a further 0.5 h, 1-iodopropane (60 mg, 0.35 mmol) was added. The mixture was stirred at room temperature for 16 h then partitioned between water and ethyl acetate. The organic phase was washed with water, brine, dried (Na$_2$SO$_4$) and the solvent removed in vacuo. Chromatography (silica gel, 50-100% ethyl acetate-pentane then 0-5% methanol-ethyl acetate) afforded the title compound as a white solid.

Mass spectrum (Electrospray LC/MS): Found 513 (MH$^+$). $C_{27}H_{27}F_3N_4OS$ requires 512.

The product was dissolved in methanol and treated with 1M HCl in diethyl ether (excess). The volatiles were removed in vacuo to afford the hydrochloride salt of the title compound as pale green solid (170 mg).

Mass spectrum (Electrospray LC/MS): Found 513. $C_{27}H_{27}F_3N_4OS$ requires 512.

EXAMPLE 71

(RS)-1-{2-[5,6-Difluoro-1-(2-methoxy-ethyl)-1H-benzoimidazol-2-ylmethyl]-piperidin-1-yl}-1-[5-(4-fluoro-phenyl)-2-methyl-thiazol-4-yl]-methanone (RS)-1-[2-(5,6-Difluoro-1H-benzoimidazol-2-ylmethyl)-piperidin-1-yl]-1-[5-(4-fluoro-phenyl)-2-methyl-thiazol-4-yl]-methanone, E35 (300 mg, 0.64 mmol) was added slowly to an ice-cooled slurry of sodium hydride (51 mg, 1.3 mmol, 60% dispersion in mineral oil) in DMF (10 ml). After stirring for 0.5 h 1-bromo-2-methoxy-ethane (139 mg, 10 mmol), N,N-diisopropylethylamine (0.3 ml) and potassium iodide (5 mg) was added. The mixture was stirred at room temperature for 0.5 h then 100° C. for 16 h. The volatiles were removed in vacuo from the cooled reaction mixture. The residue was partitioned between ethyl acetate and water. The aqueous phase was extracted with ethyl acetate (2×). The combined organics were dried (Na$_2$SO$_4$) and the solvent removed in vacuo. The residue was triturated with ethyl acetate to afford the title compound as a solid (306 mg, 65%).

Mass spectrum (Electrospray LC/MS) Found 529 (MH$^+$). $C_{27}H_{27}F_3N_4O_2S$ requires 528.

The product was dissolved in methanol and treated with 1M HCl in diethyl ether (excess). The volatiles were removed in vacuo and the residue triturated with methanol-ethyl acetate to afford the hydrochloride salt of the title compound as a white solid (66 mg).

Mass spectrum (Electrospray LC/MS): Found 529 (MH$^+$). $C_{27}H_{27}F_3N_4O_2S$ requires 528.

EXAMPLE 72

(RS)-1-{2-[1-(2-Dimethylamino-ethyl)-5,6-difluoro-1H-benzoimidazol-2-ylmethyl]-piperidin-1-yl}-1-[5-(4-fluoro-phenyl)-2-methyl-thiazol-4-yl]-methanone The title compound was prepared from (RS)-1-[2-(5,6-difluoro-1H-benzoimidazol-2-ylmethyl)-piperidin-1-yl]-1-[5-(4-fluoro-phenyl)-2-methyl-thiazol-4-yl]-methanone, E35 (300 mg) and (2-chloro-ethyl)-dimethyl-amine, according to a procedure similar to that described for Example 71 as a white solid (88 mg, 26%).

Mass spectrum (Electrospray LC/MS): Found 542 (MH$^+$). $C_{28}H_{30}F_3N_5OS$ requires 541. The hydrochloride salt of the title compound was prepared as described for E71

Mass spectrum (Electrospray LC/MS): Found 542 (MH$^+$). $C_{28}H_{30}F_3N_5OS$ requires 541.

EXAMPLE 73

(RS)-1-{2-[5,6-difluoro-1-(2-hydroxy-ethyl)-1H-benzoimidazol-2-ylmethyl]-piperidin-1-yl}-1-[5-(4-fluoro-phenyl)-2-methyl-thiazol-4-yl]-methanone (RS)-1-[2-(5,6-Difluoro-1H-benzoimidazol-2-ylmethyl)-piperidin-1-yl]-1-[5-(4-fluoro-phenyl)-2-methyl-thiazol-4-yl]-methanone, E35 (250 mg, 0.53 mmol) was added slowly to an ice-cooled slurry of sodium hydride (43 mg, 1.1 mmol, 60% dispersion in mineral oil) in DMF (10 ml), under argon. After stirring for a further 0.5 h, 2-bromoethanol (0.045 ml, 0.64 mmol) was added. The mixture was heated at 110° C. for 48 h, but only a minor amount of product had formed (MS). Potassium carbonate (1.00 g), N,N-diisopropylethylamine (1.0 ml) and a further portion of 2-bromoethanol (0.5 ml) were added and heating was continued for 16 h. The volatiles were removed in vacuo from the cooled reaction mixture. The residue was partitioned between ethyl acetate and water. The organic phase was dried (Na$_2$SO$_4$) and the solvent removed in vacuo. Chromatography (silica gel, 0-5% methanol-ethyl acetate) afforded the title compound as a white solid (78 mg, 29%).

Mass spectrum (Electrospray LC/MS): Found 515 (MH$^+$). $C_{26}H_{25}F_3N_4O_2S$ requires 514.

EXAMPLE 74 AND EXAMPLE 75

(RS)-1-[2-(6,7-Difluoro-1-methyl-1H-benzoimidazol-2-ylmethyl)-piperidin-1-yl]-1-[5-(4-fluorophenyl)-2-methyl-thiazol-4-yl]-methanone and (RS)-1-[2-(4,5-Difluoro-1-methyl-1H-benzoimidazol-2-ylmethyl)-piperidin-1-yl]-1-[5-(4-fluorophenyl)-2-methyl-thiazol-4-yl]-methanone (RS)-1-[2-(4,5-Difluoro-1H-benzoimidazol-2-ylmethyl)-piperidin-1-yl]-1-[5-(4-fluoro-phenyl)-2-methyl-thiazol-4-yl]-methanone, E36 (400 mg, 0.85 mmol) was added slowly to an ice-cooled slurry of sodium hydride (68 mg, 1.7 mmol, 60% dispersion in mineral oil) in DMF (10 ml). After stirring for a further 0.5 h, iodomethane (266 mg, 0.87 mmol) was added. The mixture was stirred at room temperature for 72 h then partitioned between water and ethyl acetate. The organic phase was washed with water, brine, dried ($Na_2SO_4$) and the solvent removed in vacuo. Purification by HPLC (Supercosil ABZ+, 5-95% acetonitrile containing 0.1% trifluoroacetic acid-water containing 0.1% trifluoroacetic acid) afforded the title compounds (structures assignment based on nOe experiments):

1-[2-(6,7-Difluoro-1-methyl-1H-benzoimidazol-2-ylmethyl)-piperidin-1-yl]-1-[5-(4-fluorophenyl)-2-methyl-thiazol-4-yl]-methanone (76 mg)

Mass spectrum (Electrospray LC/MS): Found 485 ($MH^+$). $C_{25}H_{23}F_3N_4OS$ requires 484.

$^1$H NMR δ: 0.75-1.85 (6H, bm), 2.42 and 2.72 (3H, s), 0.85-3.15 (2H, bm), 3.30 (1H, m), 3.42 (0.7H, m), 3.70 and 4.15 (3H, s), 4.25 (0.3H, m), 4.75 (0.3H, m), 5.10 (0.7H, m), 7.00 (3H, m), 7.35 (3H, m).

1-[2-(4,5-Difluoro-1-methyl-1H-benzoimidazol-2-ylmethyl)-piperidin-1-yl]-1-[5-(4-fluorophenyl)-2-methyl-thiazol-4-yl]-methanone (106 mg)

Mass spectrum (Electrospray LC/MS): Found 485 ($MH^+$). $C_{25}H_{23}F_3N_4OS$ requires 484.

$^1$H NMR δ: 0.75-1.90 (6H, bm), 2.25 and 2.70 (3H, s), 2.9-3.2 (2H, bm), 3.15-3.45 (1.7H, bm), 3.56 and 3.94 (3H, s), 4.25 (0.3H, m), 4.76 (0.3H, m), 5.09 (0.7H, m), 6.98 (3H, m), 7.08 (1H, m), 7.36 (2H, m).

EXAMPLE 76

(RS)-2-(1-{1-[5-(4-Fluorophenyl)-2-methyl-thiazol-4-yl]-methanoyl}-piperidin-2-ylmethyl)-benzofuran-3-carboxylic acid amide To a solution of (RS)-2-(1-(2,2,2-trifluoro-ethanoyl)-piperidin-2-yl-methyl)-benzofuran-3-carbonitrile, D42 (480 mg, 1.4 mmol) in methanol (15 ml) and water (3 ml) was added potassium carbonate (700 mg, 4.9 mmol) and the mixture heated at reflux for 1.25 h. The solvent was removed in vacuo and the residue was partitioned between dichloromethane and water and basified to pH14. The aqueous phase was re-extracted with dichloromethane (3×). The combined organics were dried ($Na_2SO_4$) and the solvent removed in vacuo to afford a solid (0.34 g, 99%). To a portion of this material (67 mg, 0.28 mmol) in dichloromethane was added 5-(4-fluorophenyl)-2-methyl-thiazole-4-carboxylic acid (73 mg, 0.30 mmol), EDC.HCl (60 mg, 0.30 mml) and 1-hydroxybenzotriazole (10 mg). After 16 h at room temperature the reaction mixture was washed with saturated aqueous sodium hydrogen carbonate and the organic phase applied directly onto a pre-packed silica gel column. Elution with ethyl acetate-methanol mixtures afforded the title compound as an amorphous solid (8 mg, 6%).

Mass spectrum (Electrospray LC/MS): Found 478 ($MH^+$). $C_{26}H_{24}FN_3O_3S$ requires 477.

EXAMPLE 77

(RS)-2-(1-{1-[4-(4-Fluorophenyl)-1-methyl-1H-pyrazol-3-yl]-methanoyl}-piperidin-2-ylmethyl)-benzofuran-3-carboxylic acid amide The title compound (7 mg, 5%), was prepared as described for E76 from (RS)-2-(1-(2,2,2-trifluoro-ethanoyl)-piperidin-2-yl-methyl)-benzofuran-3-carbonitrile, D42 and 4-(4-fluorophenyl)-1-methyl-1H-pyrazole carboxylic acid (61 mg, 0.3 mmol)

Mass spectrum (Electrospray LC/MS): Found 461 ($MH^+$). $C_{26}H_{25}FN_4O_3$ requires 460.

EXAMPLE 78

(RS)-1-[3-(4,5-Difluoro-1H-benzoimidazol-2-ylmethyl)-morpholin-4-yl]-1-[5-(4-fluoro-phenyl)-2-methyl-thiazol-4-yl]-methanone The title compound (93 mg, 36%) was prepared from (4-{1-[5-(4-Fluoro-phenyl)-2-methyl-thiazol-4-yl]-methanoyl}-morpholin-3-yl)-acetic acid, D45 according to the procedure described for Example 27.

Mass spectrum (Electrospray LC/MS): Found 473 ($MH^+$). $C_{23}H_{19}F_3N_4O_2S$ requires 472.

EXAMPLE 79

(RS)-1-[5-(4-Fluoro-phenyl)-2-methyl-thiazol-4-yl]-1-(2-furo[3,2-b]-pyridin-2-ylmethyl-piperidin-1-yl)methanone The title compound was prepared using the method of Example 4, from 5-(4-fluoro-phenyl)-2-methyl-thiazole-4-carboxylic acid (120 mg, 0.5 mmol) and (RS)-2-piperidin-2-ylmethyl-furo[3,2-b]pyridine, D47 (108 mg, 0.5 mmol), as a colourless solid (95 mg, 43%).

Mass spectrum (Electrospray LC/MS): Found 436 ($MH^+$). $C_{24}H_{22}FN_3O_2S$ requires 435.

EXAMPLE 80

(RS)-1-[4-(4-Fluoro-phenyl)-1-methyl-1H-pyrazole-3-yl]-(2-furo[3,2-b]pyridin-2-ylmethyl-piperidin-1-yl)methanone The title compound was prepared using the method of Example 4, from 4-(4-fluoro-phenyl)-1-methyl-1H-pyrazole-3-carboxylic acid (110 mg, 0.5 mmol) and (RS)-2-Piperidin-2-ylmethyl-furo[3,2-b]pyridine, D47 (108 mg, 0.5 mmol), as a colourless solid (130 mg, 62%).

Mass spectrum (Electrospray LC/MS): Found 419 ($MH^+$). $C_{24}H_{23}FN_4O_2$ requires 418.

EXAMPLE 81

(RS)-1-[2-(3-Bromo-benzofuran-2-ylmethyl)-piperidin-1-yl]-1-[5-(4-fluoro-phenyl)-2-methyl-thiazol-4-yl]-methanone To (RS)-2-(2-benzofuranylmethyl)-1-((5-(4-fluorophenyl)-2-methyl-thiazol-4-yl)-carbonyl)-piperidine, E1 (0.90 g, 2 mmol) in dry diethyl ether (10 ml) and dichloromethane (20 ml) cooled to −12° C. under argon, was added drop-wise a solution of bromine (0.36 g, 2 mmol) in dichloromethane (10 ml) over 0.5 h. The resulting solution was warmed to ambient temperature over 1.5 h, then stirred for a further 18 h. The reaction mixture was evaporated then re-evaporated from dichloromethane (3×). The resulting amorphous solid was chromatographed (silica gel with ethyl acetate-hexane mixtures) to afford the title compound as an amorphous solid (0.27 g, 25%).

Mass spectrum (Electrospray LC/MS) Found 513 (MH$^+$). $C_{25}H_{22}^{79}BrFN_2O_2S$ requires 512.

EXAMPLE 82

(RS)-2-(1-{1-[5-(4-Fluoro-phenyl)-2-methyl-thiazol-4-yl]-methanoyl}-piperidin-2-ylmethyl)-benzofuran-3-carbonitrile To (RS)-1-[2-(3-bromo-benzofuran-2-ylmethyl)-piperidin-1-yl]-1-[5-(4-fluoro-phenyl)-2-methyl-thiazol-4-yl]-methanone, E81 (270 mg, 0.53 mmol) in N-methyl-pyrrolidinone (8 ml) was added copper(I)cyanide (96 mg, 1.06 mmol) and the mixture stirred under argon at reflux for 6 h. The reaction mixture was cooled, poured into water (80 ml) and ethyl acetate (50 ml) and then filtered through kieselguhr. The filtrate was separated and the aqueous phase extracted with ethyl acetate (2×). The combined organics were washed with water (4×50 ml), dried and the solvent removed in vacuo. Chromatography (silica gel) afforded the title compound as a white amorphous solid (94 mg, 39%).

Mass spectrum (Electrospray LC/MS) Found 460 (MH$^+$). $C_{26}H_{22}FN_3O_2S$ requires 459.

EXAMPLE 83

(RS)-1-[2-(5-Fluorobenzofuran-2-ylmethyl)-4-methylpiperazin-1-yl]-1-[5-(4-fluorophenyl)-2-methylthiazol-4-yl]methanone.hydrochloride The title compound was prepared from (RS)-3-(5-fluorobenzofuran-2-ylmethyl)-1-methylpiperazine, D51 using the method of Example 1.

Mass spectrum (Electrospray LC/MS): Found 468 (MH$^+$). $C_{25}H_{23}F_2O_2S$ requires 467.

EXAMPLE 84

(RS)-1-(2-Benzofuran-2-ylmethyl-4-methyl-piperazin-1-yl)-1-[5-(4-fluoro-phenyl)-2-methyl-thiazol-4-yl)]-methanone The title compound (0.53 g, 32%) was obtained from (RS)-3-benzofuran-2-ylmethyl-1-methyl-piperazine, D56 (0.89 g, 3.8 mmol) using the method of Example 1.

Mass spectrum (Electrospray LC/MS): Found 450 (MH$^+$). $C_{25}H_{24}FN_3O_2S$ requires 449.

EXAMPLE 85

(RS)-1-(2-Benzofuran-2-ylmethyl-piperazin-1-yl)-1-[5-(4-fluorophenyl)-2-methyl-thiazol-4-yl]-methanone.hydrochloride To (RS)-1-(2-benzofuran-2-ylmethyl-4-methyl-piperazin-1-yl)-1-[5-(4-fluoro-phenyl)-2-methyl-thiazol-4-yl)]-methanone, E84 (0.45 g, 1 mmol) in 1,2-dichloroethane (10 ml) under argon at 0° C. was added N,N-diisopropylethylamine (0.52 ml, 3 mmol) followed by dropwise addition of 1-chloroethylchloroformate (0.77 ml, 6 mmol) over 1-2 min. After 5 min, the reaction mixture was warmed to ambient temperature over 0.5 h, and then heated at 65° C. for 4.5 h. Additional N,N-diisopropylethylamine (0.52 ml, 3 mmol) was added and heating continued for a further 2 h. The reaction was cooled and evaporated, and the residue refluxed in methanol (25 ml) for 2.5 h. The cooled reaction was evaporated and partitioned between dichloromethane (50 ml) and saturated aqueous sodium bicarbonate (25 ml), aqueous phase extracted with dichloromethane (2×25 ml). The combined organic extracts were dried ($Na_2SO_4$), evaporated and the residue chromatographed on silica gel eluting with methanol ethyl acetate mixtures to afford the free-base of the title compound (0.23 g, 52%). A sample was converted to the hydrochloride salt by dissolving in methanol/dichloromethane and treating with excess 1M HCl in diethyl ether. Removal of the solvent in vacuo afforded the title compound as an amorphous solid.

Mass spectrum (Electrospray LC/MS): Found 458 (MNa$^+$). $C_{24}H_{22}FN_3O_2S$ requires 435.

EXAMPLE 86

1-{(RS)-2-[(RS)-1-(5-Fluoro-benzofuranyl-2-yl)-1-hydroxy-methyl]-4-methyl-piperazin-1-yl}-1-[5-(4-fluoro-phenyl)-2-methyl-thiazol-4-yl]-methanone The title compound (0.043 g, 59%) was obtained from (RS)-1-(5-fluoro-benzofuran-2-yl)-1-((RS)-4-methyl-piperazin-2-yl)-methanol, D57 and 5-(4-(fluorophenyl)-2-methyl-thiazole-4-carbonyl chloride (0.043 g, 0.16 mmol) using the method of Example 1.

Mass spectrum (Electrospray LC/MS): Found 506 (MNa$^+$). $C_{25}H_{23}F_2N_3O_3S$ requires 483.

EXAMPLE 87

1-{(RS)-2-[(RS)-1-(5-Fluoro-benzofuranyl-2-yl)-1-hydroxy-methyl]-4-methyl-piperazin-1-yl}-1-(2-trifluoromethoxy-phenyl)-methanone The title compound (0.034 g, 50%) was obtained from (RS)-1-(5-fluoro-benzofuran-2-yl)-1-((RS)-4-methyl-piperizan-2-yl)-methanol, D57 and 2-(trifluoromethoxy)benzoyl chloride using the method of Example 1.

Mass spectrum (Electrospray LC/MS): Found 453 (MH$^+$). $C_{22}H_{20}F_4N_2O_4$ requires 452.

EXAMPLE 88

(RS)-1-[2-(1-{1-[5-(4-fluoro-phenyl)-2-methyl-thiazol-4-yl]-methanoyl}-piperidin-2-ylmethyl)-benzofuran-3-yl]-ethanone The title compound (120 mg, 41%) was obtained from (RS)-1-[2-(3-bromo-benzofuran-2-ylmethyl)-piperidin-1-yl]-1-[5-(4-fluoro-phenyl)-2-methyl-thiazol-4-yl]-methanone, E81 (320 mg, 0.62 mmol) using the method of Example 68.

Mass spectrum (Electrospray LC/MS): Found 477 (MH$^+$). $C_{27}H_{25}FN_2O_3S$ requires 476.

EXAMPLE 89a AND EXAMPLE 89b (R)-1-[2-(5,6-Difluoro-1H-benzoimidazol-2-ylmethyl)-piperidin-1-yl]-1-[5-(4-fluoro-phenyl)-2-methyl-thiazol-4-yl]-methanone and (S)-1-[2-(5,6-Difluoro-1H-benzoimidazol-2-ylmethyl)-piperidin-1-yl]-1-[5-(4-fluoro-phenyl)-2-methyl-thiazol-4-yl]-methanone (RS)-1-[2-(5,6-Difluoro-1H-benzoimidazol-2-ylmethyl)-piperidin-1-yl]-1-[5-(4-fluoro-phenyl)-2-methyl-thiazol-4-yl]-methanone E35 (380 mg) was separated to give the title compounds (stereochemistry not assigned) on a Chiralpak AD column (250 mm×19 mm i.d.; 10 micron particle size); Mobile Phase: n-hexane, HiPerSiolv: ethanol, 99.7% v/v-100% v/v, Analar: triethylamine, Analar (90:10:0.25 v/v/v): pre-mixed: isocratic procedure; injecting at 2.5 ml at concentration of 20 mg/ml racemate in ethanol, 99.7% v/v-100% v/v, Analar.

Faster eluting enantiomer (132 mg, >99.8% e.e.):
Mass spectrum (Electrospray LC/MS): Found 471 (MH$^+$). C$_{24}$H$_{21}$F$_3$N$_4$OS requires 470

Slower eluting enantiomer (173 mg, >99.8% e.e.):
Mass spectrum (Electrospray LC/MS): Found 471 (MH$^+$). C$_{24}$H$_{21}$F$_3$N$_4$OS requires 470

TABLE 5

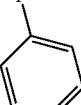

| Example | Ar$^2$ | Method | Mass Spectrum (Electrospray LC/MS) |
|---|---|---|---|
| 113 | 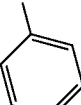 | E2 | Found MH$^+$453. C$_{24}$H$_{22}$F$_2$N$_4$OS requires 452. |
| 114 | 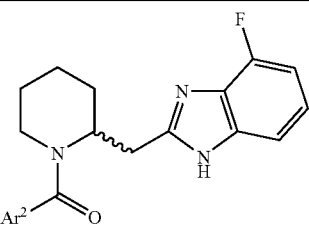 | E2 | Found MH$^+$436. C$_{24}$H$_{23}$F$_2$N$_5$O requires 435. |
| 115 | 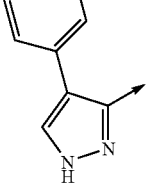 | E2 | Found MH$^+$422. C$_{23}$H$_{21}$F$_2$N$_5$O requires 421. |
| 116 | 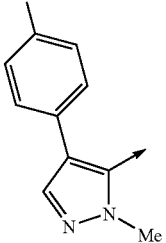 | E2 | Found MH$^+$436. C$_{24}$H$_{23}$F$_2$N$_5$O requires 435. |
| 117 | 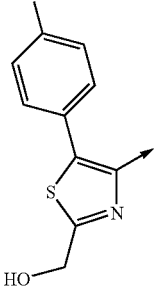 | E2 | Found MH$^+$382. C$_{22}$H$_{24}$FN$_3$O$_2$ requires 381. |
| 118 | | E4 | Found M-1 467. C$_{24}$H$_{22}$F$_2$N$_4$O$_2$S requires 468. (API LC/MS) |

The compounds of Examples 113-118 were prepared from the appropriate carboxylic acid and (RS)-4-fluoro-2-piperidin-2-ylmethyl-1H-benzoimidazole, D58 using a procedure similar to that described in Example 2 or Example 4.

EXAMPLE 119

(RS)-1-[5-(4-Fluoro-phenyl)-2-methyl-thiazol-4-yl]-1-{2-[4-(1-hydroxy-ethyl)-1H-benzoimidazol-2-ylmethyl]-piperidin-1-yl}-methanone Sodium borohydride (145 mg) was added portionwise over 2 min. to a cooled (0-10° C.) solution of (RS)-1-[2-(4-acetyl- 1H-benzimidazol-2-ylmethyl)-piperidin-1-yl]-1-[5-(4-fluorophenyl)-2-methylthiazol-4-yl]methanone, E68 (365 mg) in methanol (10 ml). After stirring for a further 2.5 h at room temperature, water (100 ml) was added and the mixture was extracted with dichloromethane (2×). The combined organics were dried (Na$_2$SO$_4$), evaporated and the residue chromatographed (silica gel, 0-100% ethyl acetate-hexane then 2-10% methanol-ethyl acetate) to afford the title compound as a solid (320 mg).

Mass spectrum (Electrospray LC/MS): Found 479 (MH$^+$). C$_{26}$H$_{27}$FN$_4$O$_2$S requires 478.

EXAMPLE 120

(RS)-1-(2-Benzofuran-2-ylmethyl-piperidin-1-yl)-1-[5-(4-chloro-phenyl)-2-methyl-thiazol-4-yl]-methanone The title compound (100 mg) was prepared from (RS)-2-(2-benzofuranylmethyl)piperidine, D3 (64 mg) and 5-(4-chloro-phenyl)-2-methyl-thiazole-4-carboxylic acid (76 mg) by a procedure similar to that described for Example 2.

Mass spectrum (API LC/MS): Found 451 (MH$^+$). C$_{25}$H$_{23}$$^{35}$ClN$_2$O$_2$S requires 450.

EXAMPLE 121

(RS)-1-[2-(3-Chloro-furo[3,2-b]pyridin-2-ylmethyl)-piperidin-1-yl]-1-[5-(4-fluoro-phenyl)-2-methyl-thiazol-4-yl]-methanone A solution of chlorine (28 mg) in dichloromethane (3 ml) was added to a cooled (−12° C.) solution (RS)-1-[5-(4-fluorophenyl)-2-methyl-thiazol-4-yl]-1-(2-furo[3,2-b]-pyridin-2-ylmethyl-piperidin-1-yl)methanone, E79 (170 mg) in dichloromethane (4 ml). After stirring at −12° C. for 0.5 h the reaction mixture was stirred at room temperature for 16 h then the solution was washed with saturated aqueous NaHCO$_3$, dried (Na$_2$SO$_4$) and the solvent removed in vacuo. Chromatography (silica gel, 0-100% ethyl acetate-hexane then 0-10% methanol-ethyl acetate) afforded the title compound (24 mg).

Mass spectrum (Electrospray LC/MS): Found 470 (MH$^+$). C$_{24}$H$_{21}$$^{35}$ClFN$_3$O$_2$S requires 469.

EXAMPLE 122

(RS)-1-[2-(5,6-Difluoro-1-methyl-1H-benzoimidazol-2-ylmethyl)-piperidin-1-yl]-1-[5-(4-fluoro-phenyl)-2-hydroxymethyl-thiazol-4-yl]-methanone The title compound (15 mg) was prepared from 5-(4-fluoro-phenyl)-2-hydroxymethyl-thiazole-4-carboxylic acid (84 mg) and (RS)-5,6-difluoro-1-methyl-2-piperidin-2-ylmethyl-1H-benzoimidazole, D61 (86 mg) by a procedure similar to that described for Example 4.

Mass spectrum (Electrospray LC/MS): Found 501 (MH$^+$). C$_{25}$H$_{23}$F$_3$N$_4$O$_2$S requires 500.

EXAMPLE 123

(RS)-1-[2-(5-Chloro-benzofuran-2-ylmethyl)-4-methyl-piperazin-1-yl]-1-[5-(4-fluoro-phenyl)-2-methyl-thiazol-4-yl]-methanone The title compound (135 mg) was prepared from 5-(4-fluoro-phenyl)-2-methyl-thiazole-4-carbonyl chloride (211 mg) and 3-(5-Chloro-benzofuran-2-ylmethyl)-1-methyl-piperazine, D63 (200 mg) by a procedure similar to that described for Example 1.

Mass spectrum (API$^+$LC/MS): Found 484 (MH$^+$). C$_{25}$H$_{23}$$^{35}$ClFN$_3$O$_2$S requires 483

EXAMPLE 124

(RS)-1-[2-(5-Chloro-benzofuran-2-ylmethyl)-piperazin-1-yl]-1-[5-(4-fluoro-phenyl)-2-methyl-thiazol-4-yl]-methanone The title compound was prepared from 1-[2-(5-chloro-benzofuran-2-ylmethyl)-4-methyl-piperazin-1-yl]-1-[5-(4-fluoro-phenyl)-2-methyl-thiazol-4-yl]-methanone, E123 (95 mg) by a procedure similar to that described for Example 85.

Purification by HPLC (Supercosil ABZ$^+$, 5-95% acetonitrile containing 0.1% trifluoroacetic acid-water containing 0.1% trifluoroacetic acid) afforded the title compound (5 mg) as the TFA salt.

Mass spectrum (Electrospray LC/MS): Found 470 (MH$^+$). C$_{24}$H$_{21}$$^{35}$ClFN$_3$O$_2$S requires 469.

EXAMPLE 125

(RS)-1-[2-(5,7-Dichloro-benzofuran-2-ylmethyl)-4-methyl-piperazin-1-yl]-1-[5-(4-fluoro-phenyl)-2-methyl-thiazol-4-yl]-methanone The title compound (80 mg) was prepared from 5-(4-fluoro-phenyl)-2-methyl-thiazole-4-carbonyl chloride (498 mg) and (RS)-3-(5,7-dichloro-benzofuran-2-ylmethyl)-1-methyl-piperazine, D65 (530 mg) by a procedure similar to that described for Example 1.

Mass spectrum (API$^+$LC/MS): Found 518 (MH$^+$). C$_{25}$H$_{22}$$^{35}$Cl$_2$FN$_3$O$_2$S requires 517.

EXAMPLE 126

(RS)-1-[2-(5,7-Dichloro-benzofuran-2-ylmethyl)-piperazin-1-yl]-1-[5-(4-fluoro-phenyl)-2-methyl-thiazol-4-yl]-methanone The title compound was prepared from (RS)-1-[2-(5,7-dichloro-benzofuran-2-ylmethyl)-4-methyl-piperazin-1-yl]-1-[5-(4-fluoro-phenyl)-2-methyl-thiazol-4-yl]-methanone E125 (72 mg) by a procedure similar to that described for Example 85. Purification by HPLC (Supercosil ABZ$^+$, 5-95% acetonitrile containing 0.1% trifluoroacetic acid-water containing 0.1% trifluoroacetic acid) afforded the title compound (6 mg) as the TFA salt.

Mass spectrum (Electrospray LC/MS): Found 504 (MH$^+$). C$_{24}$H$_{20}$$^{35}$Cl$_2$FN$_3$O$_2$S requires 503.

EXAMPLE 127

(RS)-1-[5-(4-Fluoro-phenyl)-2-methyl-thiazol-4-yl]-1-[2-(1H-indol-2-ylmethyl)-piperidin-1-yl]-methanone (RS)-1-[5-(4-Fluoro-phenyl)-2-methyl-thiazol-4-yl]-1-{2-[1-(2-trimethylsilanyl-ethoxymethyl)-1H-indol-2-ylmethyl]-piperidin-1-yl}-methanone (130 mg) was prepared from (RS)-2-piperidin-2-ylmethyl-1-(2-trimethylsilanyl-ethoxymethyl)-1H-indole, D68 (520 mg) and 5-(4-fluorophenyl)-2-methyl-thiazole-4-carbonyl chloride (512 mg) according to a procedure similar to that for Example 1. A stirring solution of the above amide (125 mg) in dry THF (5 ml) was treated with a solution of tetrabutylammonium fluoride (2.2 mmol) in THF (5 ml). Once tlc indicated the reaction had gone to completion, the reaction mixture was poured into water and the product extracted with ethyl acetate. The combined organics were washed with brine, dried ($Na_2SO_4$) and the solvent removed in vacuo. Chromatography (silica gel, 0-100% pentane-ethyl acetate followed by preparative tlc, 40% ethyl acetate-pentane) afforded the title compound as a white solid (2.5 mg).

Mass spectrum (Electrospray LC/MS): Found 434 ($MH^+$). $C_{25}H_{24}FN_3OS$ requires 433.

EXAMPLE 128

(RS)-5-[1-(2-Benzofuran-2-ylmethyl-piperidin-1-yl)-methanoyl]-4H-benzo[1,4]oxazin-3-one The title compound (65 mg) was prepared from (RS)-2-(2-benzofuranylmethyl)piperidine, D3 (65 mg) and 3-oxo-3,4-dihydro-2H-benzo[1,4]oxazine-5-carboxylic acid (39 mg) by a procedure similar to that for Example 2.

Mass spectrum (Electrospray LC/MS): Found 391 ($MH^+$). $C_{23}H_{22}N_2O_4$ requires 390.

EXAMPLE 129

(RS)-1-[2-(5-Bromo-benzofuran-2-ylmethyl)-piperidin-1-yl]-1-[5-(4-fluoro-phenyl)-2-methyl-thiazol-4-yl]-methanone The title compound (490 mg) was prepared from 5-(4-fluoro-phenyl)-2-methyl-thiazole-4-carbonyl chloride (488 mg) and (RS)-2-(5-bromo-benzofuran-2-ylmethyl)-piperidine, D70 (530 mg) by a procedure similar to that described for Example 1.

Mass spectrum (Electrospray LC/MS): Found 513 ($MH^+$). $C_{25}H_{22}{}^{79}BrFN_2O_2S$ requires 512.

EXAMPLE 130

(RS)-1-[2-(5-Cyano-benzofuran-2-ylmethyl)-piperidin-1-yl]-1-[5-(4-fluoro-phenyl)-2-methyl-thiazol-4-yl]-methanone The title compound (19 mg) was prepared from (RS)-1-[2-(5-bromo-benzofuran-2-ylmethyl)-piperidin-1-yl]-1-[5-(4-fluoro-phenyl)-2-methyl-thiazol-4-yl]-methanone, E129 (420 mg) and copper(I)cyanide according to a procedure similar to that described for Example 67.

Mass spectrum ($API^+$LC/MS): Found 460 ($MH^+$). $C_{26}H_{22}FN_3O_2S$ requires 459.

EXAMPLE 131

(RS)-1-[2-(4-Bromo-benzofuran-2-ylmethyl)-piperidin-1-yl]-1-[5-(4-fluoro-phenyl)-2-methyl-thiazol-4-yl]-methanone The title compound (0.45 g) was prepared from 5-(4-fluoro-phenyl)-2-methyl-thiazole-4-carbonyl chloride (0.89 g) and 2-(4-bromo-benzofuran-2-ylmethyl)-piperidine, D72 (0.88 g) by a procedure similar to that described for Example 1.

Mass spectrum (Electrospray LC/MS): Found 513 ($MH^+$). $C_{25}H_{22}{}^{79}BrFN_2O_2S$ requires 512.

EXAMPLE 132

(RS)-1-[2-(4-Cyano-benzofuran-2-ylmethyl)-piperidin-1-yl]-1-[5-(4-fluoro-phenyl)-2-methyl-thiazol-4-yl]-methanone The title compound (80 mg) was prepared from (RS)-1-[2-(4-bromo-benzofuran-2-ylmethyl)-piperidin-1-yl]1-[5-(4-fluoro-phenyl)-2-methyl-thiazol-4-yl]-methanone, E131 (400 mg) and copper(I)cyanide according to a procedure similar to that described for Example 67.

Mass spectrum (Electrospray LC/MS): Found 460 ($MH^+$). $C_{26}H_{22}FN_3O_2S$ requires 459.

EXAMPLE 133

(RS)-1-[5-(4-Fluoro-phenyl)-2-methyl-thiazol-4-yl]-1-[2-(3-methyl-benzofuran-2-ylmethyl)-piperidin-1-yl]-methanone The title compound (18 mg) was prepared from (RS)-2-(3-methyl-benzofuran-2-ylmethyl)-piperidine, D74 (92 mg) and 5-(4-fluoro-phenyl)-2-methyl-thiazole-4-carboxylic acid (190 mg) according to a procedure similar to that described for Example 4.

Mass spectrum (API LC/MS): Found 449 ($MH^+$). $C_{26}H_{25}FN_2O_2S$ requires 448.

EXAMPLE 134

(RS)-1-[2-(4-Fluoro-benzofuran-2-ylmethyl)-piperidin-1-yl]-1-[5-(4-fluoro-phenyl)-2-methyl-thiazol-4-yl]-methanone The title compound (60 mg) was prepared from (RS)-2-(4-fluoro-benzofuran-2-ylmethyl)-piperidine, D76 (157 mg) and 5-(4-fluoro-phenyl)-2-methyl-thiazole-4-carboxylic acid (160 mg) according to a procedure similar to that described for Example 4.

Mass spectrum (API LC/MS): Found 453 ($MH^+$). $C_{25}H_{22}F_2N_2O_2S$ requires 452.

EXAMPLE 135

(RS)-1-[2-(4-Fluoro-benzofuran-2-ylmethyl)-piperidin-1-yl]-1-[4-(4-fluoro-phenyl)-1-methyl-1H-pyrazol-3-yl]-methanone The title compound (45 mg) was prepared from (RS)-2-(4-fluoro-benzofuran-2-ylmethyl)-piperidine, D76 (157 mg) and 4-(4-fluoro-phenyl)-1-methyl-1H-pyrazole-3-carboxylic acid (160 mg) according to a procedure similar to that described for Example 4.

Mass spectrum (API LC/MS): Found 436 ($MH^+$). $C_{25}H_{23}F_2N_3O_2$ requires 435.

EXAMPLE 136

(RS)-1-[2-(4,6-Dichloro-benzofuran-2-ylmethyl)-4-methyl-piperazin-1-yl]-1-[5-(4-fluoro-phenyl)-2-methyl-thiazol-4-yl]-methanone The title compound (107 mg) was prepared from 5-(4-fluoro-phenyl)-2-methyl-thiazole-4-carbonyl chloride (241 mg) and 3-(4,6-dichloro-benzofuran-2-ylmethyl)-1-methyl-piperazine, D78 (263 mg) by a procedure similar to that described for Example 1.

EXAMPLE 137

(RS)-1-[2-(4,6-Dichloro-benzofuran-2-ylmethyl)-piperazin-1-yl]-1-[5-(4-fluoro-phenyl)-2-methyl-thiazol-4-yl]-methanone The title compound was prepared from (RS)-1-[2-(4,6-dichloro-benzofuran-2-ylmethyl)-4-methyl-piperazin-1-yl]-1-[5-(4-fluoro-phenyl)-2-methyl-thiazol-4-yl]-methanone, E136 (87 mg) by a procedure similar to that described for Example 85.

Purification by HPLC (Supercosil ABZ+, 5-95% acetonitrile containing 0.1% trifluoroacetic acid-water containing 0.1% trifluoroacetic acid) afforded the title compound (mg) as the TFA salt.

Mass spectrum (Electrospray LC/MS): Found 504 (MH+). $C_{24}H_{20}{}^{35}Cl_2FN_3O_2S$ requires 503.

Mass spectrum (Electrospray LC/MS): Found 518 (MH+). $C_{25}H_{22}{}^{35}Cl_2FN_3O_2S$ requires 517.

EXAMPLE 138

(RS)-1-(2-Benzofuran-2-ylmethyl-pyrrolidin-1-yl)-1-[5-(4-fluoro-phenyl)-2-methyl-thiazol-4-yl]-methanone The title compound (45 mg) was prepared from (RS)-2-benzofuran-2-ylmethyl-pyrrolidine D81 (114 mg) and 5-(4-fluoro-phenyl)-2-methyl-thiazole-4-carboxylic acid (147 mg) according to a procedure similar to that described for Example 4.

Mass spectrum (Electrospray LC/MS): Found 421 (MH+). $C_{24}H_{21}FN_2O_2S$ requires 420.

EXAMPLE 139

(RS)-1-(2-Benzofuran-2-ylmethyl-pyrrolidin-1-yl)-1-[4-(4-fluoro-phenyl)-1-methyl-1H-pyrazol-3-yl]-methanone The title compound (29 mg) was prepared from (RS)-2-benzofuran-2-ylmethyl-pyrrolidine D81 (114 mg) and 4-(4-fluoro-phenyl)-1-methyl-1H-pyrazole-3-carboxylic acid (137 mg) according to a procedure similar to that described for Example 4.

Mass spectrum (Electrospray LC/MS): Found 404 (MH+). $C_{24}H_{22}FN_3O_2$ requires 403.

EXAMPLE 140

(RS)-1-(2-Benzo[b]thiophen-2-ylmethyl-piperidin-1-yl)-1-[5-(4-fluoro-phenyl)-2-methyl-thiazol-4-yl]-methanone The title compound (40 mg) was prepared from 2-benzo[b]thiophen-2-ylmethyl-piperidine D83 (133 mg) and 5-(4-fluoro-phenyl)-2-methyl-thiazole-4-carboxylic acid (136 mg) according to a procedure similar to that described for Example 4.

Mass spectrum (Electrospray LC/MS): Found 451 (MH+). $C_{25}H_{23}FN_2OS_2$ requires 450.

EXAMPLE 141

(RS)-1-(2-Benzo[b]thiophen-2-ylmethyl-piperidin-1-yl)-1-[4-(4-fluoro-phenyl)-1-methyl-1H-pyrazol-3-yl]-methanone The title compound (6 mg) was prepared from 2-benzo[b]thiophen-2-ylmethyl-piperidine D83 (133 mg) and 4-(4-fluoro-phenyl)-1-methyl-1H-pyrazole-3-carboxylic acid (140 mg) according to a procedure similar to that described for Example 4.

Mass spectrum (Electrospray LC/MS): Found 434 (MH+). $C_{25}H_{24}FN_3OS$ requires 433.

EXAMPLE 142

(RS)-1-(2-Benzo[b]thiophen-2-ylmethyl-piperidin-1-yl)-1-quinolin-8-yl-methanone

The title compound (4 mg) was prepared from 2-benzo[b]thiophen-2-ylmethyl-piperidine D83 (133 mg) and 8-quinoline carboxylic acid (109 mg) according to a procedure similar to that described for Example 4.

Mass spectrum (Electrospray LC/MS): Found 387 (MH+). $C_{24}H_{22}N_2OS$ requires 386

EXAMPLE 143

(RS)-1-(2-Benzofuran-2-ylmethyl-piperidin-1-yl)-1-(2-methyl-5-phenyl-thiazol-4-yl)-methanone The title compound (90 mg) was prepared from (RS)-2-(2-benzofuranylmethyl)piperidine, D3 (100 mg) and 5-phenyl-2-methyl-thiazole-4-carbonyl chloride (122 mg) according to a procedure similar to that for Example 1.

Mass spectrum (Electrospray LC/MS): Found 417 (MH+). $C_{25}H_{24}N_2O_2S$ requires 416.

EXAMPLE 144

1-[(S)-2-(5,6-Difluoro-1H-benzoimidazol-2-ylmethyl)-pyrrolidin-1-yl]-1-[5-(4-fluoro-phenyl)-2-hydroxymethyl-thiazol-4-yl]-methanone The title compound (65 mg) was prepared from 5,6-difluoro-2-(S)-1-pyrrolidin-2-ylmethyl-1H-benzoimidazole, D27 (153 mg) and 5-(4-fluoro-phenyl)-2-hydroxymethyl-thiazole-4-carboxylic acid (205 mg) according to a procedure similar to that for Example 4.

Mass spectrum (Electrospray LC/MS): Found 473 (MH+). $C_{23}H_{19}F_3N_4O_2S$ requires 472.

EXAMPLE 145

(RS)-1-(2-Benzofuran-2-ylmethyl-piperidin-1-yl)-1-[2-(3-methyl-[1,2,4]oxadiazol-5-yl)-phenyl]-methanone The title compound (33 mg) was prepared from (RS)-2-(2-benzofuranylmethyl)piperidine, D3 (108 mg) and 2-(3-methyl-[1,2,4]oxadiazol-5-yl)-benzoic acid (102 mg) according to a procedure similar to that for Example 2.

Mass spectrum (Electrospray LC/MS): Found 402 (MH+). $C_{24}H_{23}N_3O_3$ requires 401.

EXAMPLE 146a AND EXAMPLE 146b (R)-1-[2-(4,6-Difluoro-1H-benzoimidazol-2-ylmethyl)-piperidin-1-yl]-1-[5-(4-fluoro-phenyl)-2-methyl-thiazol-4-yl]-methanone and (S)-1-[2-(4,6-Difluoro-1H-benzoimidazol-2-ylmethyl)-piperidin-1-yl]-1-[5-(4-fluoro-phenyl)-2-methyl-thiazol-4-yl]-methanone (enantiomers of Example 32)

(RS)-1-[2-(4,6-Difluoro-1H-benzoimidazol-2-ylmethyl)-piperidin-1-yl]-1-[5-(4-fluoro-phenyl)-2-methyl-thiazol-4-yl]-methanone, E32 was separated to give the title compounds (stereochemistry not assigned) using the following procedures:

Analytical separation: 10 uL of diluted sample (compound in methanol) was separated on a 4.6×250 mm, 10 micron, analytical ChiralCel OD column. A Berger Analytical SFC (Super Critical Fluid) instrument was used with system parameters as follows: mobile phase=90% $CO_2$:10% organic modifier, organic modifier=90% methanol:10% chloroform v/v, 3000 psi, 2 mL/min, 40 C λ=254 nm The enantiomers eluted at 6.4 min. and 8.1 min.

Preparative separation: Scale-up was preformed on a Prochrom Super C.20 instrument. The instrument parameters were as follows: 40 C, 21 MPa, 40 g/min CO2+4.5 ml/min organic modifier (as above), λ=300 nm, ChiralCel OD 20×250 mm, 10 micron column. 30 mg of racemate was introduced per cycle. Sample concentration=875 mg/13 ml solvent (sample solvent=5 ml chloroform and 8 mL methanol). Cycle time (run time)=17 minutes. The enantiomers eluted at 10.2 and 13.6 min. Elution times measured at peak maxima.

It is understood that the present invention covers all combinations of particular and preferred groups described herein above.

Determination of Orexin-1 Receptor Antagonist Activity

The orexin-1 receptor antagonist activity of the compounds of formula (I) was determined in accordance with the following experimental method.

Experimental Method

CHO-DG44 cells expressing the human orexin-1 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37 C in 5% $CO_2$.

Agonists were prepared as 1 mM stocks in water:DMSO (1:1). EC50 values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist IC50 values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 60 min at 37 C in 5% CO2. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37 C in 5% $CO_2$ for 30 minutes. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 seconds (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, *TiPS*, 1995, 16, 413-417) to generate a concentration effect value. Antagonist Kb values were calculated using the equation:

$$Kb=IC50/(1+([3/EC50])$$

where EC50 was the potency of human orexin-A determined in the assay (in nM terms) and IC50 is expressed in molar terms.

Compounds of Examples tested according to this method had pKb values>7.0 to 9.4 at the human cloned orexin-1 receptor.

The orexin-2 receptor antagonist activity of the compounds of formula (I) was determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37 C in 5% $CO_2$.

Agonists were prepared as 1 mM stocks in water:DMSO (1:1). EC50 values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist IC50 values (the concentration of compound needed to inhibit 50% of the agonist response) were determined against 10.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 60 min at 37 C in 5% $CO_2$. The loading solution containing dye was then aspirated and cells were washed with 4×150 µl Tyrode's buffer containing probenecid and 0.1% gelatin (Denley Cell Wash). The volume of buffer left in each well was 125 µl. Antagonist or buffer (25 µl) was added (Quadra) the cell plates gently shaken and incubated at 37 C in 5% $CO_2$ for 30 min. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, *TiPS*, 1995, 16, 413-417) to generate a concentration effect value. Antagonist Kb values were calculated using the equation:

$$Kb = IC50/(1+([3/EC50])$$

where EC50 was the potency of human orexin-A determined in the assay (in nM terms) and IC50 is expressed in molar terms.

Compounds of Examples tested according to this method had pKb values in the range 6.5-8.4 at the human cloned orexin-2 receptor.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

The invention claimed is:

1. A compound of formula (I):

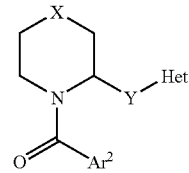

wherein
X represents $CH_2$;
Y represents $CH_2$, CH(OH), or $CH_2$CH(OH);
Het is an optionally substituted benzofuranyl;
$Ar^2$ represents an optionally substituted isoquinolinyl group;
wherein said optionally substituted Het or $Ar^2$ groups are optionally substituted by halogen, hydroxy, oxo, cyano, nitro, $(C_{1-4})$alkyl, $(C_{1-4})$alkoxy, hydroxy$(C_{1-4}$alkyl, hydroxy$(C_{1-4})$alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$alkyl, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$alkylsulfonyl$(C_{1-4})$alkyl, arylsulfonyl, arylsulfonyloxy, arylsulfonyl$(C_{1-4})$alkyl, $(C_{1-4})$alkylsulfonamido, $(C_{1-4})$alkylamido, $(C_{1-4})$alkylsulfonamido$(C_{1-4})$alkyl, $(C_{1-4})$alkylamido$(C_{1-4})$alkyl, arylsulfonamido, arylcarboxamido, arylsulfonamido$(C_{1-4})$alkyl, arylcarboxamido$(C_{1-4})$alkyl, aroyl, aroyl$(C_{1-4})$alkyl, aryl$(C_{1-4})$alkanoyl, $(C_{1-4})$acyl, aryl, aryl$(C_{1-4})$alkyl, $(C_{1-4})$alkylamino$(C_{1-4})$alkyl, or $R^aR^bN$—, $R^aOCO(CH_2)_r$, $R^aCON(R^a)(CH_2)_r$, $R^aR^bNCO(CH_2)_r$, $R^aR^bNSO_2(CH_2)_r$, $R^aSO_2NR^b(CH_2)_r$, $R^aR^bN(CH_2)_n$—, $R^aR^bN(CH_2)_nO$—, wherein r represents zero or an integer from 1 to 4, n represents an integer from 1 to 4, and each of $R^a$ and $R^b$ independently represents a hydrogen atom or a $(C_{1-4})$alkyl group, or a pharmaceutically acceptable salt thereof.

2. A compound according to claim 1 wherein $Ar^2$ is optionally substituted by

---

SEQUENCE LISTING

<160> NUMBER OF SEQ ID NOS: 1

<210> SEQ ID NO 1
<211> LENGTH: 35
<212> TYPE: PRT
<213> ORGANISM: Homo sapien

<400> SEQUENCE: 1

Glu Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu Asn His
        35

($C_{1-4}$)alkyl, hydroxy($C_{1-4}$)alkyl, $R^a R^b N$, ($C_{1-4}$)alkoxy, $R^a R^b N(CH_2)n$, ($C_{1-4}$)acyl, and ($C_{1-4}$)alkylamido.

3. A compound according to claim 1 wherein Y represents $CH_2$.

4. A compound:
(RS)-1-(2-Benzofuran-2-ylmethyl-piperidin-1-yl)-1-isoquinolin-8-yl-methanone;
(RS)-1-(2-Benzofuran-2-ylmethyl-piperidin-1-yl)-1-isoquinolin-5-yl-methanone;
or a pharmaceutically acceptable salt of any one thereof.

5. A pharmaceutical composition comprising a therapeutically effective amount of the compound according to claim 1, or a pharmaceutically acceptable salt thereof, and a pharmaceutically acceptable carrier.

6. A method of treating a disease or disorder where an antagonist of a human orexin receptor is required, which comprises administering to a subject in need thereof an effective amount of the compound according to claim 1, or a pharmaceutically acceptable salt thereof, wherein said disease or disorder is selected from obesity and obesity associated with Type II diabetes.

7. A method of treating insomnia which comprises administering to a subject in need thereof an effective amount of the compound according to claim 1, or a pharmaceutically acceptable salt thereof.

* * * * *